(12) United States Patent
Kleiner

(10) Patent No.: US 8,292,960 B2
(45) Date of Patent: *Oct. 23, 2012

(54) SPINAL FUSION CAGE WITH REMOVABLE PLANAR ELEMENTS

(75) Inventor: Jeffrey B. Kleiner, Denver, CO (US)

(73) Assignee: Kleiner Intellectual Property, LLC, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/473,366

(22) Filed: May 16, 2012

(65) Prior Publication Data

US 2012/0226358 A1 Sep. 6, 2012

Related U.S. Application Data

(63) Continuation of application No. 13/277,272, filed on Oct. 20, 2011, which is a continuation of application No. 12/367,487, filed on Feb. 6, 2009, now Pat. No. 8,088,163.

(60) Provisional application No. 61/026,608, filed on Feb. 6, 2008, provisional application No. 61/055,399, filed on May 22, 2008, provisional application No. 61/074,924, filed on Jun. 23, 2008.

(51) Int. Cl.
*A61F 2/44* (2006.01)
(52) U.S. Cl. ................... 623/17.11; 623/17.12
(58) Field of Classification Search ............... 623/17.11, 623/17.16
See application file for complete search history.

(56) References Cited

U.S. PATENT DOCUMENTS

| | | | |
|---|---|---|---|
| 3,697,011 A | 10/1972 | Christensen et al. |
| 3,741,496 A | 6/1973 | Beller |
| 3,836,092 A | 9/1974 | Hull |
| 3,855,638 A | 12/1974 | Pilliar |
| 4,039,156 A | 8/1977 | Abraham |
| 4,041,939 A | 8/1977 | Hall |
| 4,047,524 A | 9/1977 | Hall |
| 4,206,516 A | 6/1980 | Pilliar |
| 4,277,184 A | 7/1981 | Solomon |

(Continued)

FOREIGN PATENT DOCUMENTS

WO WO 99/08627 2/1999

(Continued)

OTHER PUBLICATIONS

U.S. Appl. No. 13/168,611, Kleiner.

(Continued)

*Primary Examiner* — Andrew Yang
*Assistant Examiner* — Olivia C Chang
(74) *Attorney, Agent, or Firm* — Sheridan Ross P.C.

(57) ABSTRACT

The present disclosure relates to a spinal fusion impactor tool that includes an attachment means for securing an implant device to the distal end of the tool, a means for adjusting the angle of the distal head relative to the handle to better position the implant for introduction into the implant site, means for remotely releasing the implant device at the distal end and a clamp device on the shaft of the tool to secure tabs, attachments and other devices. The impactor tool is preferably used in conjunction with implantation of an intervertebral fusion cage that is equipped with shims having tabs or other removing means, but may also be used to introduce, for example, an implant, graft, fusion device, wedge or distractor device into any joint space or bony region in preparation for implantation.

11 Claims, 23 Drawing Sheets

U.S. PATENT DOCUMENTS

| | | |
|---|---|---|
| 4,430,062 A | 2/1984 | Henrichsen et al. |
| 4,462,402 A | 7/1984 | Burgio et al. |
| 4,467,478 A | 8/1984 | Jurgutis |
| 4,501,269 A | 2/1985 | Bagby |
| 4,522,270 A | 6/1985 | Kishi |
| 4,570,623 A | 2/1986 | Ellison et al. |
| 4,580,978 A | 4/1986 | Motola et al. |
| 4,592,346 A | 6/1986 | Jurgutis |
| 4,743,256 A | 5/1988 | Brantigan |
| 4,877,399 A | 10/1989 | Frank et al. |
| 4,991,570 A | 2/1991 | Bullard |
| 5,037,422 A | 8/1991 | Hayhurst |
| 5,053,038 A | 10/1991 | Sheehan |
| 5,055,104 A | 10/1991 | Ray |
| 5,058,823 A | 10/1991 | Emura et al. |
| 5,282,744 A | 2/1994 | Meyer |
| 5,290,295 A | 3/1994 | Querals et al. |
| 5,311,640 A | 5/1994 | Holland |
| 5,312,407 A | 5/1994 | Carter |
| 5,312,417 A | 5/1994 | Wilk |
| 5,324,307 A | 6/1994 | Jarrett et al. |
| 5,329,834 A | 7/1994 | Wong |
| 5,333,812 A | 8/1994 | Sato |
| 5,354,292 A | 10/1994 | Braeuer et al. |
| 5,395,372 A | 3/1995 | Holt et al. |
| 5,431,658 A | 7/1995 | Moskovich |
| D364,462 S | 11/1995 | Michelson |
| 5,520,611 A | 5/1996 | Rao et al. |
| 5,527,312 A | 6/1996 | Ray |
| 5,541,191 A | 7/1996 | Skotnicki et al. |
| 5,549,607 A | 8/1996 | Olson et al. |
| 5,558,674 A | 9/1996 | Heggeness et al. |
| D374,283 S | 10/1996 | Michelson |
| 5,562,661 A | 10/1996 | Yoshimi et al. |
| 5,569,246 A | 10/1996 | Ojima et al. |
| 5,586,989 A | 12/1996 | Bray |
| 5,595,563 A | 1/1997 | Moisdon |
| 5,601,557 A | 2/1997 | Hayhurst |
| D378,409 S | 3/1997 | Michelson |
| 5,611,800 A | 3/1997 | Davis et al. |
| 5,634,925 A | 6/1997 | Urbanski |
| 5,653,763 A | 8/1997 | Errico et al. |
| 5,662,655 A | 9/1997 | Laboureau et al. |
| 5,665,122 A | 9/1997 | Kambin |
| 5,688,285 A | 11/1997 | Yamada |
| 5,697,932 A | 12/1997 | Smith et al. |
| 5,702,449 A | 12/1997 | McKay |
| 5,704,892 A | 1/1998 | Adair |
| 5,741,253 A | 4/1998 | Michelson |
| 5,762,629 A | 6/1998 | Kambin |
| 5,779,642 A | 7/1998 | Nightengale |
| 5,782,919 A | 7/1998 | Zdeblick et al. |
| 5,797,918 A | 8/1998 | McGuire et al. |
| 5,836,948 A | 11/1998 | Zucherman et al. |
| 5,836,958 A | 11/1998 | Ralph |
| 5,860,977 A | 1/1999 | Zucherman et al. |
| 5,865,746 A | 2/1999 | Murugesan et al. |
| 5,865,846 A | 2/1999 | Bryan et al. |
| 5,871,462 A | 2/1999 | Yoder et al. |
| 5,888,228 A | 3/1999 | Knothe et al. |
| 5,904,689 A | 5/1999 | Jonjic |
| 5,906,616 A | 5/1999 | Pavlov et al. |
| 5,925,051 A | 7/1999 | Mikhail |
| 5,944,658 A | 8/1999 | Koros et al. |
| 5,944,686 A | 8/1999 | Patterson et al. |
| 5,947,972 A | 9/1999 | Gage et al. |
| 5,976,146 A | 11/1999 | Ogawa et al. |
| 5,989,257 A | 11/1999 | Tidwell et al. |
| 5,997,895 A | 12/1999 | Narotam et al. |
| 6,004,191 A | 12/1999 | Schur et al. |
| 6,004,326 A | 12/1999 | Castro et al. |
| 6,013,028 A | 1/2000 | Jho et al. |
| 6,019,765 A | 2/2000 | Thornhill et al. |
| 6,030,356 A | 2/2000 | Carlson et al. |
| 6,030,388 A | 2/2000 | Yoshimi et al. |
| 6,030,390 A | 2/2000 | Mehdizadeh |
| 6,030,401 A | 2/2000 | Marino |
| 6,033,408 A | 3/2000 | Gage et al. |
| 6,033,438 A | 3/2000 | Bianchi et al. |
| 6,045,555 A | 4/2000 | Smith et al. |
| 6,090,143 A | 7/2000 | Meriwether et al. |
| 6,096,080 A | 8/2000 | Nicholson et al. |
| 6,113,602 A | 9/2000 | Sand |
| 6,120,503 A | 9/2000 | Michelson |
| 6,136,001 A | 10/2000 | Michelson |
| 6,142,998 A | 11/2000 | Smith et al. |
| 6,146,420 A | 11/2000 | McKay |
| 6,149,096 A | 11/2000 | Hartley |
| 6,152,871 A | 11/2000 | Foley et al. |
| 6,159,245 A | 12/2000 | Meriwether et al. |
| 6,180,085 B1 | 1/2001 | Achilefu |
| 6,209,886 B1 | 4/2001 | Estes et al. |
| 6,216,573 B1 | 4/2001 | Moutafis et al. |
| 6,224,599 B1 | 5/2001 | Baynham et al. |
| 6,235,805 B1 | 5/2001 | Chang et al. |
| 6,238,397 B1 | 5/2001 | Zucherman et al. |
| 6,241,733 B1 | 6/2001 | Nicholson et al. |
| 6,241,769 B1 | 6/2001 | Nicholson et al. |
| 6,245,108 B1 | 6/2001 | Biscup |
| 6,258,094 B1 | 7/2001 | Nicholson et al. |
| 6,261,293 B1 | 7/2001 | Nicholson et al. |
| 6,261,295 B1 | 7/2001 | Nicholson et al. |
| 6,261,296 B1 | 7/2001 | Aebi et al. |
| 6,290,724 B1 | 9/2001 | Marino |
| 6,299,613 B1 | 10/2001 | Ogilvie et al. |
| 6,309,395 B1 | 10/2001 | Smith et al. |
| 6,325,805 B1 | 12/2001 | Ogilvie et al. |
| 6,328,738 B1 | 12/2001 | Suddaby |
| 6,336,928 B1 | 1/2002 | Guerin et al. |
| 6,364,880 B1 | 4/2002 | Michelson |
| 6,375,635 B1 | 4/2002 | Moutafis et al. |
| 6,387,096 B1 | 5/2002 | Hyde, Jr. |
| 6,409,765 B1 | 6/2002 | Bianchi et al. |
| 6,436,101 B1 | 8/2002 | Hamada |
| 6,451,017 B1 | 9/2002 | Moutafis et al. |
| 6,454,806 B1 | 9/2002 | Cohen et al. |
| 6,467,556 B2 | 10/2002 | Alsruhe |
| 6,500,206 B1 | 12/2002 | Bryan |
| 6,511,493 B1 | 1/2003 | Moutafis et al. |
| 6,520,976 B1 | 2/2003 | Gage |
| 6,524,318 B1 | 2/2003 | Longhini et al. |
| 6,565,574 B2 | 5/2003 | Michelson |
| 6,569,201 B2 | 5/2003 | Moumene et al. |
| 6,616,669 B2 | 9/2003 | Ogilvie et al. |
| 6,620,356 B1 | 9/2003 | Wong et al. |
| 6,641,613 B2 | 11/2003 | Sennett |
| 6,648,915 B2 | 11/2003 | Sazy |
| 6,652,533 B2 | 11/2003 | O'Neil |
| 6,669,710 B2 | 12/2003 | Moutafis et al. |
| 6,673,113 B2 | 1/2004 | Ralph et al. |
| 6,679,887 B2 | 1/2004 | Nicholson et al. |
| 6,695,882 B2 | 2/2004 | Bianchi et al. |
| 6,699,288 B2 | 3/2004 | Moret |
| 6,709,438 B2 | 3/2004 | Dixon et al. |
| 6,719,760 B2 | 4/2004 | Dorchak et al. |
| 6,719,795 B1 | 4/2004 | Cornwall et al. |
| 6,730,125 B1 | 5/2004 | Lin |
| 6,743,257 B2 | 6/2004 | Castro |
| 6,764,491 B2 | 7/2004 | Frey et al. |
| 6,773,437 B2 | 8/2004 | Ogilvie et al. |
| 6,800,093 B2 | 10/2004 | Nicholson et al. |
| 6,824,565 B2 | 11/2004 | Muhanna et al. |
| 6,830,574 B2 | 12/2004 | Heckele et al. |
| 6,890,728 B2 | 5/2005 | Dolecek et al. |
| 6,899,712 B2 | 5/2005 | Moutafis et al. |
| 6,923,792 B2 | 8/2005 | Staid et al. |
| 6,929,646 B2 | 8/2005 | Gambale |
| 6,942,665 B2 | 9/2005 | Gambale |
| 6,960,182 B2 | 11/2005 | Moutafis et al. |
| 6,962,592 B2 | 11/2005 | Gatturna et al. |
| 6,969,523 B1 | 11/2005 | Mattern et al. |
| 6,974,480 B2 | 12/2005 | Messerli et al. |
| 6,994,728 B2 | 2/2006 | Zubok et al. |
| 7,004,946 B2 | 2/2006 | Parker et al. |
| 7,008,431 B2 | 3/2006 | Simonson |
| 7,014,640 B2 | 3/2006 | Kemppainen et al. |
| 7,025,742 B2 | 4/2006 | Rubenstein et al. |

| | | |
|---|---|---|
| 7,025,769 B1 | 4/2006 | Ferree |
| 7,033,317 B2 | 4/2006 | Pruitt |
| 7,041,136 B2 | 5/2006 | Goble et al. |
| 7,066,961 B2 | 6/2006 | Hichelson |
| 7,077,864 B2 | 7/2006 | Byrd, III et al. |
| 7,094,257 B2 | 8/2006 | Mujwid et al. |
| 7,122,017 B2 | 10/2006 | Moutafis et al. |
| 7,128,760 B2 | 10/2006 | Michelson |
| 7,135,043 B2 | 11/2006 | Nakahara et al. |
| 7,182,782 B2 | 2/2007 | Kirschman |
| 7,204,825 B2 | 4/2007 | Cimino et al. |
| 7,207,992 B2 | 4/2007 | Ritland |
| 7,211,112 B2 | 5/2007 | Baynham et al. |
| 7,214,186 B2 | 5/2007 | Ritland |
| 7,223,292 B2 | 5/2007 | Messerli et al. |
| 7,232,463 B2 | 6/2007 | Falahee |
| 7,238,203 B2 | 7/2007 | Bagga et al. |
| 7,255,703 B2 | 8/2007 | Mujwid et al. |
| 7,267,691 B2 | 9/2007 | Keller et al. |
| 7,273,498 B2 | 9/2007 | Bianchi et al. |
| 7,288,093 B2 | 10/2007 | Michelson |
| 7,316,070 B2 | 1/2008 | Green |
| 7,329,283 B2 | 2/2008 | Estes et al. |
| 7,337,538 B2 | 3/2008 | Moutafis et al. |
| 7,341,590 B2 | 3/2008 | Ferree |
| 7,341,591 B2 | 3/2008 | Grinberg |
| 7,357,284 B2 | 4/2008 | Jauvin |
| 7,357,804 B2 | 4/2008 | Binder, Jr. et al. |
| 7,361,178 B2 | 4/2008 | Hearn et al. |
| 7,364,657 B2 | 4/2008 | Mandrusov et al. |
| 7,371,239 B2 | 5/2008 | Dec et al. |
| 7,377,923 B2 | 5/2008 | Purcell et al. |
| 7,387,643 B2 | 6/2008 | Michelson |
| 7,399,041 B2 | 7/2008 | Prentner et al. |
| D574,495 S | 8/2008 | Petersen |
| 7,406,775 B2 | 8/2008 | Funk et al. |
| 7,410,334 B2 | 8/2008 | McGrew |
| 7,410,478 B2 | 8/2008 | Yang |
| 7,413,065 B2 | 8/2008 | Gauthier |
| 7,421,772 B2 | 9/2008 | Gao et al. |
| 7,429,270 B2 | 9/2008 | Baumgartner et al. |
| 7,430,945 B2 | 10/2008 | Gauthier et al. |
| 7,431,711 B2 | 10/2008 | Moutafis et al. |
| 7,442,208 B2 | 10/2008 | Mathieu et al. |
| 7,455,157 B2 | 11/2008 | Kimes et al. |
| 7,461,803 B2 | 12/2008 | Boerner |
| 7,473,255 B2 | 1/2009 | McGarity et al. |
| 7,476,226 B2 | 1/2009 | Weikel et al. |
| 7,478,577 B1 | 1/2009 | Wheeler |
| 7,481,766 B2 | 1/2009 | Lee et al. |
| 7,481,813 B1 | 1/2009 | Purcell |
| 7,485,145 B2 | 2/2009 | Purcell |
| D589,626 S | 3/2009 | Petersen |
| 7,501,073 B2 | 3/2009 | Wen et al. |
| 7,503,933 B2 | 3/2009 | Michelson |
| 7,503,934 B2 | 3/2009 | Eisermann et al. |
| 7,503,936 B2 | 3/2009 | Trieu |
| D590,943 S | 4/2009 | Petersen |
| D593,202 S | 5/2009 | Petersen |
| 7,531,003 B2 | 5/2009 | Reindel |
| 7,534,265 B1 | 5/2009 | Boyd |
| 7,534,270 B2 | 5/2009 | Ball |
| 7,553,320 B2 | 6/2009 | Molz, IV et al. |
| 7,578,820 B2 | 8/2009 | Moore et al. |
| 7,582,058 B1 | 9/2009 | Miles et al. |
| 7,582,107 B2 | 9/2009 | Trail et al. |
| 7,595,043 B2 | 9/2009 | Hedrick et al. |
| D603,502 S | 11/2009 | Petersen |
| 7,618,423 B1 | 11/2009 | Valentine et al. |
| 7,625,374 B2 | 12/2009 | Branch et al. |
| 7,632,276 B2 | 12/2009 | Fishbein |
| 7,655,027 B2 | 2/2010 | Michelson |
| 7,658,766 B2 | 2/2010 | Melkent et al. |
| 7,674,297 B2 | 3/2010 | Falahee |
| 7,677,418 B2 | 3/2010 | Henniges et al. |
| 7,686,805 B2 | 3/2010 | Michelson |
| 7,691,133 B2 | 4/2010 | Partin et al. |
| 7,693,562 B2 | 4/2010 | Marino et al. |
| 7,708,761 B2 | 5/2010 | Petersen |
| 7,717,685 B2 | 5/2010 | Moutafis et al. |
| 7,722,530 B2 | 5/2010 | Davison |
| 7,722,613 B2 | 5/2010 | Sutterlin et al. |
| 7,728,868 B2 | 6/2010 | Razzaque et al. |
| 7,730,563 B1 | 6/2010 | Sklar et al. |
| 7,734,327 B2 | 6/2010 | Colquhoun |
| 7,740,634 B2 | 6/2010 | Orbay et al. |
| 7,740,661 B2 | 6/2010 | Baratz et al. |
| 7,744,555 B2 | 6/2010 | DiMauro et al. |
| 7,744,637 B2 | 6/2010 | Johnson et al. |
| 7,744,973 B2 | 6/2010 | Schoenle et al. |
| 7,749,231 B2 | 7/2010 | Bonvallet et al. |
| 7,749,253 B2 | 7/2010 | Zucherman et al. |
| 7,749,269 B2 | 7/2010 | Peterman et al. |
| 7,749,273 B2 | 7/2010 | Cauthen et al. |
| 7,749,274 B2 | 7/2010 | Razian |
| 7,749,276 B2 | 7/2010 | Fitz |
| 7,749,279 B2 | 7/2010 | Twomey et al. |
| 7,749,555 B2 | 7/2010 | Zanella |
| 7,751,865 B2 | 7/2010 | Jascob et al. |
| 7,753,911 B2 | 7/2010 | Ray et al. |
| 7,753,914 B2 | 7/2010 | Ruhling et al. |
| 7,753,938 B2 | 7/2010 | Aschmann et al. |
| 7,753,940 B2 | 7/2010 | Veldman et al. |
| 7,753,962 B2 | 7/2010 | Melder |
| 7,758,501 B2 | 7/2010 | Frasier et al. |
| 7,758,616 B2 | 7/2010 | LeHuec et al. |
| 7,758,617 B2 | 7/2010 | Iott et al. |
| 7,758,644 B2 | 7/2010 | Trieu |
| 7,758,648 B2 | 7/2010 | Castleman et al. |
| 7,763,025 B2 | 7/2010 | Assell et al. |
| 7,763,035 B2 | 7/2010 | Melkent et al. |
| 7,763,055 B2 | 7/2010 | Foley |
| 7,763,078 B2 | 7/2010 | Peterman et al. |
| 7,763,080 B2 | 7/2010 | Southworth |
| D621,509 S | 8/2010 | Lovell |
| D622,395 S | 8/2010 | Iott et al. |
| D622,843 S | 8/2010 | Horton |
| D622,851 S | 8/2010 | Horton |
| 7,766,914 B2 | 8/2010 | McCormack et al. |
| 7,766,918 B2 | 8/2010 | Allard et al. |
| 7,766,930 B2 | 8/2010 | DiPoto et al. |
| 7,766,940 B2 | 8/2010 | Kwak et al. |
| 7,766,967 B2 | 8/2010 | Francis |
| 7,766,969 B2 | 8/2010 | Justin et al. |
| 7,769,422 B2 | 8/2010 | DiSilvestro et al. |
| 7,771,143 B2 | 8/2010 | Bharadwaj et al. |
| 7,771,475 B2 | 8/2010 | Michelson |
| 7,771,476 B2 | 8/2010 | Justis et al. |
| 7,771,479 B2 | 8/2010 | Humphreys et al. |
| 7,776,040 B2 | 8/2010 | Markworth et al. |
| 7,776,046 B2 | 8/2010 | Boyd et al. |
| 7,776,047 B2 | 8/2010 | Fanger et al. |
| 7,776,049 B1 | 8/2010 | Curran et al. |
| 7,776,075 B2 | 8/2010 | Bruneau et al. |
| 7,776,090 B2 | 8/2010 | Winslow et al. |
| 7,776,091 B2 | 8/2010 | Mastrorio et al. |
| 7,776,094 B2 | 8/2010 | McKinley et al. |
| 7,776,095 B2 | 8/2010 | Peterman et al. |
| 7,776,594 B2 | 8/2010 | Bays et al. |
| 7,780,707 B2 | 8/2010 | Johnson et al. |
| 7,794,396 B2 | 9/2010 | Gattani et al. |
| 7,794,501 B2 | 9/2010 | Edie et al. |
| 7,799,034 B2 | 9/2010 | Johnson et al. |
| 7,799,036 B2 | 9/2010 | Davison et al. |
| 7,799,053 B2 | 9/2010 | Haid et al. |
| 7,799,054 B2 | 9/2010 | Kwak et al. |
| 7,799,055 B2 | 9/2010 | Lim |
| 7,799,056 B2 | 9/2010 | Sankaran |
| 7,799,076 B2 | 9/2010 | Sybert et al. |
| 7,799,078 B2 | 9/2010 | Embry et al. |
| 7,799,083 B2 | 9/2010 | Smith et al. |
| 7,806,901 B2 | 10/2010 | Stad et al. |
| 7,811,327 B2 | 10/2010 | Hansell et al. |
| 7,811,329 B2 | 10/2010 | Ankney et al. |
| 7,815,681 B2 | 10/2010 | Ferguson |
| 7,819,801 B2 | 10/2010 | Miles et al. |
| D627,460 S | 11/2010 | Horton |
| 7,824,328 B2 | 11/2010 | Gattani et al. |

| | | | | | | |
|---|---|---|---|---|---|---|
| 7,824,332 B2 | 11/2010 | Fakhrai | | 2008/0147191 A1 | 6/2008 | Lopez et al. |
| 7,824,410 B2 | 11/2010 | Simonson | | 2008/0154375 A1 | 6/2008 | Serhan et al. |
| 7,828,804 B2 | 11/2010 | Li et al. | | 2008/0154377 A1 | 6/2008 | Voellmicke |
| 7,828,845 B2 | 11/2010 | Estes et al. | | 2008/0195058 A1 | 8/2008 | Moutafis et al. |
| 7,828,849 B2 | 11/2010 | Lim | | 2008/0249569 A1 | 10/2008 | Waugh et al. |
| 7,837,713 B2 | 11/2010 | Petersen | | 2008/0255564 A1 | 10/2008 | Michelson |
| 7,837,732 B2 | 11/2010 | Zucherman et al. | | 2008/0269904 A1 | 10/2008 | Voorhies |
| D629,896 S | 12/2010 | Horton | | 2008/0288071 A1 | 11/2008 | Biyani et al. |
| 7,846,210 B2 | 12/2010 | Perez-Cruet et al. | | 2009/0043312 A1 | 2/2009 | Koulisis |
| 7,850,733 B2 | 12/2010 | Baynham et al. | | 2009/0076440 A1 | 3/2009 | Moutafis et al. |
| 7,850,735 B2 | 12/2010 | Eisermann et al. | | 2009/0076556 A1 | 3/2009 | McGarity et al. |
| 7,850,736 B2 | 12/2010 | Heinz et al. | | 2009/0088765 A1 | 4/2009 | Butler et al. |
| 7,867,277 B1 | 1/2011 | Tohmeh | | 2009/0098184 A1 | 4/2009 | Govil et al. |
| 7,905,840 B2 | 3/2011 | Pimenta et al. | | 2009/0124860 A1 | 5/2009 | Miles et al. |
| 7,918,891 B1 | 4/2011 | Curran et al. | | 2009/0124980 A1 | 5/2009 | Chen |
| 7,927,361 B2 | 4/2011 | Oliver et al. | | 2009/0125066 A1 | 5/2009 | Krau et al. |
| 7,935,124 B2 | 5/2011 | Frey et al. | | 2009/0187194 A1 | 7/2009 | Hamada |
| 7,951,107 B2 | 5/2011 | Staid et al. | | 2009/0192350 A1 | 7/2009 | Meja |
| D642,268 S | 7/2011 | Qureshi | | 2009/0192403 A1 | 7/2009 | Gharib et al. |
| 7,985,256 B2 | 7/2011 | Grotz et al. | | 2009/0198245 A1 | 8/2009 | Phan |
| 8,088,163 B1 | 1/2012 | Kleiner | | 2009/0198249 A1 | 8/2009 | Ziegler |
| D656,610 S | 3/2012 | Kleiner | | 2009/0198337 A1 | 8/2009 | Phan |
| 2002/0049448 A1 | 4/2002 | Sand et al. | | 2009/0198338 A1 | 8/2009 | Phan |
| 2003/0040798 A1* | 2/2003 | Michelson ............. 623/17.11 | | 2009/0198339 A1 | 8/2009 | Kleiner et al. |
| 2003/0083748 A1 | 5/2003 | Lee et al. | | 2009/0203967 A1 | 8/2009 | Branch et al. |
| 2003/0149482 A1 | 8/2003 | Michelson | | 2009/0204148 A1 | 8/2009 | Lenke |
| 2004/0024466 A1 | 2/2004 | Heerklotz et al. | | 2009/0204159 A1 | 8/2009 | Justis et al. |
| 2004/0087956 A1 | 5/2004 | Weikel et al. | | 2009/0204220 A1 | 8/2009 | Trieu |
| 2004/0133217 A1 | 7/2004 | Watschke | | 2009/0222011 A1 | 9/2009 | Lehuec et al. |
| 2004/0143330 A1 | 7/2004 | Sazy | | 2009/0248163 A1 | 10/2009 | King et al. |
| 2004/0153158 A1 | 8/2004 | Errico et al. | | 2009/0259108 A1 | 10/2009 | Miles et al. |
| 2004/0167532 A1 | 8/2004 | Olson, Jr. et al. | | 2009/0264892 A1 | 10/2009 | Beyar et al. |
| 2004/0176853 A1 | 9/2004 | Sennett et al. | | 2009/0275995 A1 | 11/2009 | Truckai |
| 2004/0215201 A1 | 10/2004 | Liberman | | 2009/0299477 A1 | 12/2009 | Clayton et al. |
| 2004/0230211 A1 | 11/2004 | Moutafis et al. | | 2009/0306692 A1 | 12/2009 | Barrington et al. |
| 2005/0124993 A1 | 6/2005 | Chappuis | | 2010/0010367 A1 | 1/2010 | Foley et al. |
| 2005/0124994 A1 | 6/2005 | Berger et al. | | 2010/0010524 A1 | 1/2010 | Barrington et al. |
| 2005/0149035 A1 | 7/2005 | Pimenta et al. | | 2010/0016903 A1 | 1/2010 | Matityahu et al. |
| 2005/0149192 A1 | 7/2005 | Zucherman et al. | | 2010/0016972 A1 | 1/2010 | Jansen et al. |
| 2005/0159765 A1 | 7/2005 | Moutafis et al. | | 2010/0016973 A1 | 1/2010 | de Villiers et al. |
| 2005/0165405 A1 | 7/2005 | Tsou | | 2010/0030065 A1 | 2/2010 | Farr et al. |
| 2005/0216002 A1 | 9/2005 | Simonson | | 2010/0036226 A9 | 2/2010 | Marino et al. |
| 2005/0216018 A1 | 9/2005 | Sennett | | 2010/0036442 A1 | 2/2010 | Lauryssen et al. |
| 2005/0251257 A1 | 11/2005 | Mitchell et al. | | 2010/0042221 A1 | 2/2010 | Boyd |
| 2005/0283150 A1 | 12/2005 | Moutafis et al. | | 2010/0057208 A1 | 3/2010 | Dryer |
| 2006/0004367 A1 | 1/2006 | Alamin et al. | | 2010/0063516 A1 | 3/2010 | Parmer et al. |
| 2006/0100304 A1 | 5/2006 | Vresilovic et al. | | 2010/0063554 A1 | 3/2010 | Branch et al. |
| 2006/0111779 A1 | 5/2006 | Petersen | | 2010/0076335 A1 | 3/2010 | Gharib et al. |
| 2006/0111780 A1 | 5/2006 | Petersen | | 2010/0076445 A1 | 3/2010 | Pagano |
| 2006/0122597 A1 | 6/2006 | Jones et al. | | 2010/0076446 A1 | 3/2010 | Gorek |
| 2006/0155170 A1 | 7/2006 | Hanson et al. | | 2010/0082036 A1 | 4/2010 | Reiley et al. |
| 2006/0167461 A1 | 7/2006 | Hawkins et al. | | 2010/0087828 A1 | 4/2010 | Krueger et al. |
| 2006/0190081 A1 | 8/2006 | Kraus | | 2010/0087875 A1 | 4/2010 | McGahan et al. |
| 2006/0229550 A1 | 10/2006 | Staid et al. | | 2010/0100141 A1 | 4/2010 | de Villiers et al. |
| 2006/0247650 A1 | 11/2006 | Yerby et al. | | 2010/0105986 A1 | 4/2010 | Miles et al. |
| 2006/0264808 A1 | 11/2006 | Staid et al. | | 2010/0105987 A1 | 4/2010 | Miles et al. |
| 2006/0264964 A1 | 11/2006 | Scifert et al. | | 2010/0121365 A1 | 5/2010 | O'Sullivan et al. |
| 2007/0003598 A1 | 1/2007 | Trieu | | 2010/0121453 A1 | 5/2010 | Peterman |
| 2007/0043442 A1 | 2/2007 | Abernathie | | 2010/0125333 A1 | 5/2010 | Zdeblick et al. |
| 2007/0067034 A1 | 3/2007 | Chirico et al. | | 2010/0125338 A1 | 5/2010 | Fitz |
| 2007/0073110 A1 | 3/2007 | Larson et al. | | 2010/0131020 A1 | 5/2010 | Heinz et al. |
| 2007/0073294 A1 | 3/2007 | Chin et al. | | 2010/0137690 A1 | 6/2010 | Miles et al. |
| 2007/0088007 A1 | 4/2007 | Ng et al. | | 2010/0137923 A1 | 6/2010 | Greenhalgh et al. |
| 2007/0172790 A1 | 7/2007 | Doucette, Jr. et al. | | 2010/0145390 A1 | 6/2010 | McCarthy et al. |
| 2007/0185496 A1 | 8/2007 | Beckman et al. | | 2010/0145391 A1 | 6/2010 | Kleiner |
| 2007/0208423 A1 | 9/2007 | Messerli et al. | | 2010/0145452 A1 | 6/2010 | Blaylock et al. |
| 2007/0213596 A1 | 9/2007 | Hamada | | 2010/0145461 A1 | 6/2010 | Landry et al. |
| 2007/0213717 A1 | 9/2007 | Trieu | | 2010/0160923 A1 | 6/2010 | Sand et al. |
| 2007/0213718 A1 | 9/2007 | Trieu | | 2010/0160982 A1 | 6/2010 | Justis et al. |
| 2007/0213822 A1 | 9/2007 | Trieu | | 2010/0161062 A1 | 6/2010 | Foley et al. |
| 2007/0242869 A1 | 10/2007 | Luo et al. | | 2010/0161074 A1 | 6/2010 | McKay |
| 2007/0250166 A1 | 10/2007 | McKay | | 2010/0168755 A1 | 7/2010 | Reiley et al. |
| 2007/0270951 A1 | 11/2007 | Davis et al. | | 2010/0168862 A1 | 7/2010 | Edie et al. |
| 2007/0276406 A1 | 11/2007 | Mahoney et al. | | 2010/0174326 A1 | 7/2010 | Selover et al. |
| 2007/0288007 A1 | 12/2007 | Burkus et al. | | 2010/0185286 A1 | 7/2010 | Allard |
| 2008/0003255 A1 | 1/2008 | Kerr et al. | | 2010/0185287 A1 | 7/2010 | Allard |
| 2008/0009929 A1 | 1/2008 | Harris et al. | | 2010/0185288 A1 | 7/2010 | Carls |
| 2008/0033440 A1 | 2/2008 | Moskowitz et al. | | 2010/0191334 A1 | 7/2010 | Keller |
| 2008/0058606 A1 | 3/2008 | Miles et al. | | 2010/0191337 A1 | 7/2010 | Zamani et al. |

| | | |
|---|---|---|
| 2010/0198140 A1 | 8/2010 | Lawson |
| 2010/0199483 A1 | 8/2010 | Justis et al. |
| 2010/0204798 A1 | 8/2010 | Gerbec et al. |
| 2010/0217398 A1 | 8/2010 | Keller |
| 2010/0222784 A1 | 9/2010 | Schwab et al. |
| 2010/0222824 A1 | 9/2010 | Simonson |
| 2010/0228294 A1 | 9/2010 | LeHuec et al. |
| 2010/0228351 A1 | 9/2010 | Ankney et al. |
| 2010/0234848 A1 | 9/2010 | Sutterlin et al. |
| 2010/0234957 A1 | 9/2010 | Zdeblick et al. |
| 2010/0256767 A1 | 10/2010 | Melkent |
| 2010/0256768 A1 | 10/2010 | Lim et al. |
| 2010/0262241 A1 | 10/2010 | Eisermann et al. |
| 2010/0262245 A1 | 10/2010 | Alfaro et al. |
| 2010/0286778 A1 | 11/2010 | Eisermann et al. |
| 2010/0286784 A1 | 11/2010 | Curran et al. |
| 2010/0298938 A1 | 11/2010 | Humphreys et al. |
| 2010/0312103 A1 | 12/2010 | Gorek et al. |
| 2010/0312290 A1 | 12/2010 | McKinley et al. |
| 2010/0312347 A1 | 12/2010 | Arramon et al. |
| 2011/0015748 A1 | 1/2011 | Molz, IV |
| 2011/0071536 A1 | 3/2011 | Kleiner |
| 2011/0093005 A1 | 4/2011 | Strokosz et al. |
| 2011/0144755 A1 | 6/2011 | Baynham et al. |
| 2012/0035668 A1 | 2/2012 | Manninen et al. |
| 2012/0059477 A1 | 3/2012 | Kleiner |

FOREIGN PATENT DOCUMENTS

| | | |
|---|---|---|
| WO | WO 2005/037149 | 4/2005 |

OTHER PUBLICATIONS

U.S. Appl. No. 13/367,295, Kleiner.

U.S. Appl. No. 29/415,847, Kleiner.

Ray, C., "Facet Joint Disorders and Back Pain," published on Spine-Health, Dec. 10, 2002, available at www.spine-health.com/conditions/arthritis/facet-joint-disorders-and-back-pain, 1 page.

Staehler, R., "Spine Surgery for a Cervical Herniated Disc," published on Spine-Health, Jun. 12, 2002, available at www.spine-health.com/conditions/herniated-disc/spine-surgery-a-cervical-herniated-disc, 2 pages.

Staehler, R., "Summary of Cervical Herniated Disc Treatment Options," published on Spine-Health, Jun. 12, 2002, available at www.spine-health.com/conditions/herniated-disc/summary-cervical-herniated-disc-treatment-options, 1 page.

Ullrich, P.F., "Anterior Cervical Spinal Fusion Surgery," published on Spine-Health, Oct. 7, 2005, available at www.spine-health.com/treatment/back-surgery/anterior-cervical-spinal-fusion-surgery, 2 pages.

Ullrich, P.F., "Cervical Spinal Instrumentation," published on Spine-Health, Oct. 7, 2005, available at www.spine-health.com/treatment/back-surgery/cervical-spinal-instrumentation, 2 pages.

Wascher, T.M., "Anterior cervical decompression and spine fusion procedure," published on Spine-Health, Aug. 29, 2001, available at www.spine-health.com/treatment/spinal-fusion/anterior-cervical-decompression-and-spine-fusion-procedure, 2 pages.

"BAK® /Proximity™ (BP® ) Cage", Zimmer Website, as early as Oct. 23, 2007, available at http://www.zimmer.com/z/ctl/op/global/action/1/id/7930/template/MP/prcat/M6/prod/y, printed on Jun. 8, 2009, 1 page.

"BAK® Vista® Radiolucent Interbody Fusion System", Zimmer Website, as early as Oct. 25, 2005, available at http://www.zimmerindia.com/z/ctl/op/global/action/1/id/7809/template/MP/prcat/M6/prod/y, printed on Jun. 8, 2009, pp. 1-2.

"Facet Joint Syndrome," The Cleveland Clinic Foundation, copyright 1995-2008, printed Nov. 19, 2008, available at http://my.clevelandclinic.org/disorders/facet_joint_syndrome/hic_facet_joint_syndrome.aspx, 2 pages.

"Screws, Cages or Both", Spine Universe Website, as early as Aug. 18, 2002, available at http://www.spineuniverse.com/displayarticle.php/article1363.html, printed on Jun. 8, 2009, pp. 1-13.

"University of Maryland Spine Program: A Patient's Guide to Anterior Lumbar Interbody Fusion with Intervertebral Cages", University of Maryland Medical Center website, as early as 2003, available at http://www.umm.edu/spinecenter/education/anterior_lumbar_interbody_fusion_with_intervertebral_cages.htm, printed on Jun. 8, 2009, pp. 1-4.

"Vertebral column," from Wikipedia, the free encyclopedia, printed May 19, 2009, retrieved from http://en.wikipedia.org/wiki/Vertebral_column, 6 pages.

"Zygapophysial joint," from Wikipedia, the free encyclopedia, printed May 19, 2009, retrieved from http://en.wikipedia.org/wiki/Zygapophysial_joint, 2 pages.

International Search Report for International (PCT) Patent Application No. PCT/US2009/033488, mailed. Mar. 25, 2009, 2 pages.

Written Opinion for International (PCT) Patent Application No. PCT/US2009/033488, mailed. Mar. 25, 2009, 9 pages.

Official Action for U.S. Appl. No. 12/367,487, mailed Aug. 3, 2011 10 pages.

Notice of Allowance for U.S. Appl. No. 29/393,737, mailed Jan. 11, 2012 9 pages.

Notice of Allowance for U.S. Appl. No. 29/415,847, mailed Jul. 17, 2012 10 pages.

Notice of Allowance for U.S. Appl. No. 13/277,272, mailed Jun. 11, 2012 8 pages.

* cited by examiner

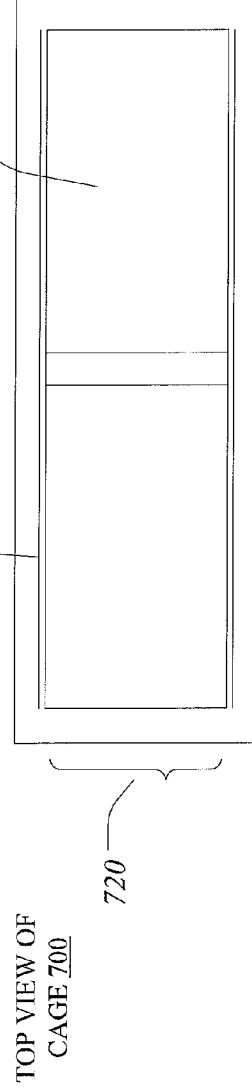
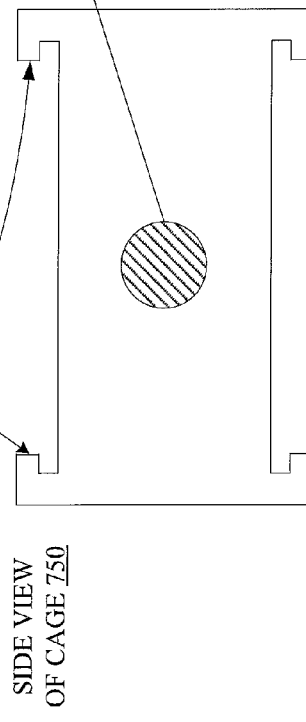
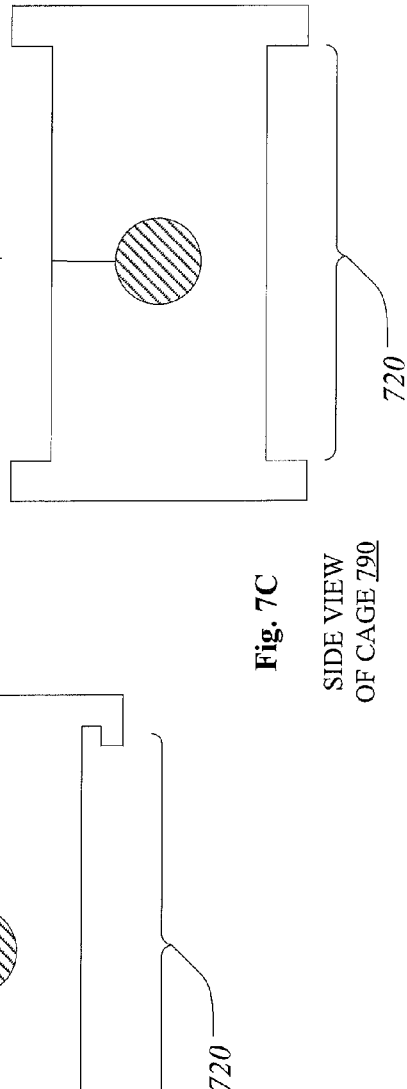
Fig. 7A
TOP VIEW OF CAGE 700
Fig. 7B
SIDE VIEW OF CAGE 750
Fig. 7C
SIDE VIEW OF CAGE 790

TOP VIEW OF TAB 800

SIDE VIEW OF TAB 850

TOP VIEW OF SHIM 1100

SHIM IS INTRODUCED INTO THE CAGE SLOT AFTER GRAFTING MATERIAL IS APPLIED. THE SHIMS ARE REMOVED AFTER THE CAGE IS SEATED.

SIDE VIEW OF SHIM 1150

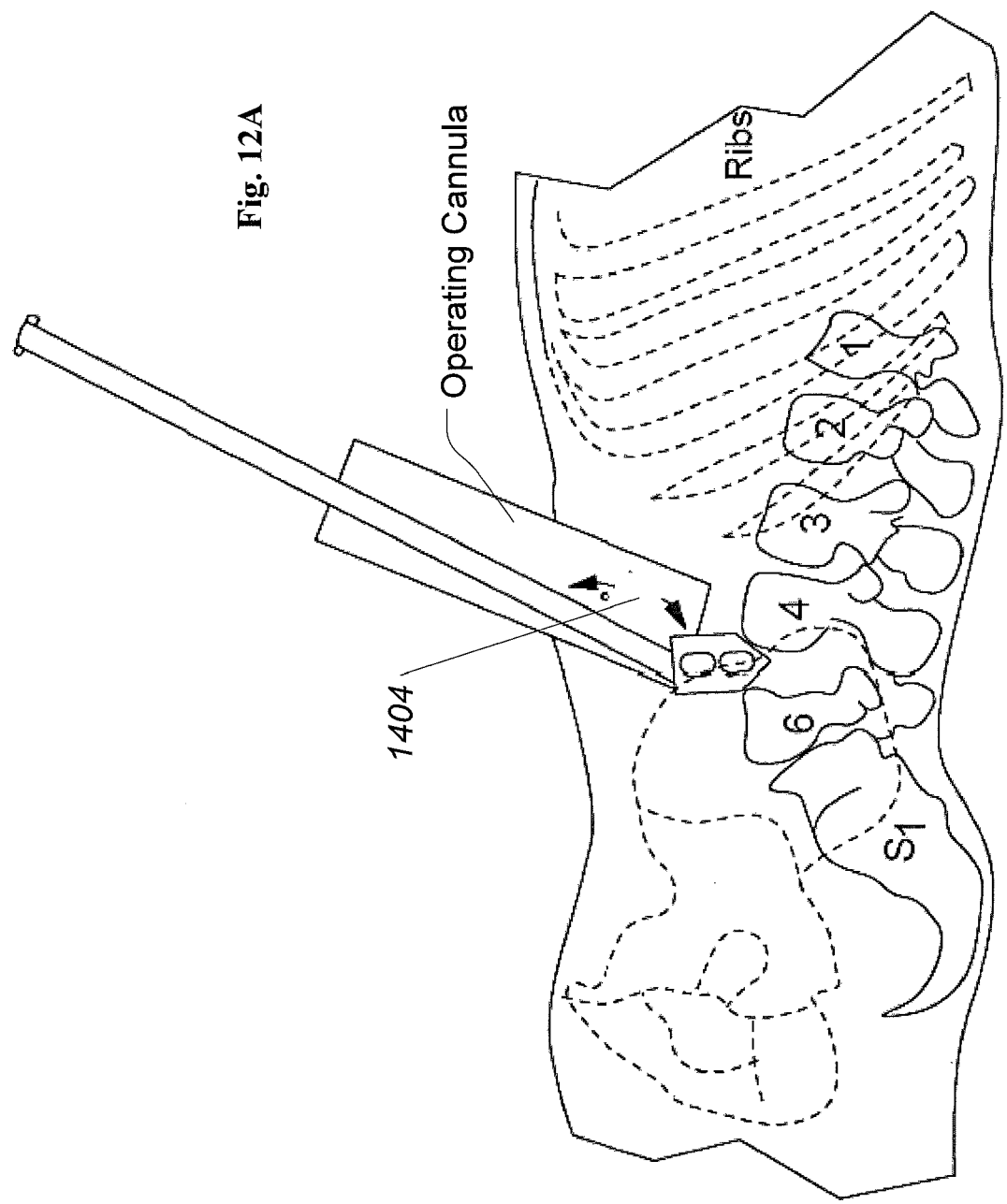

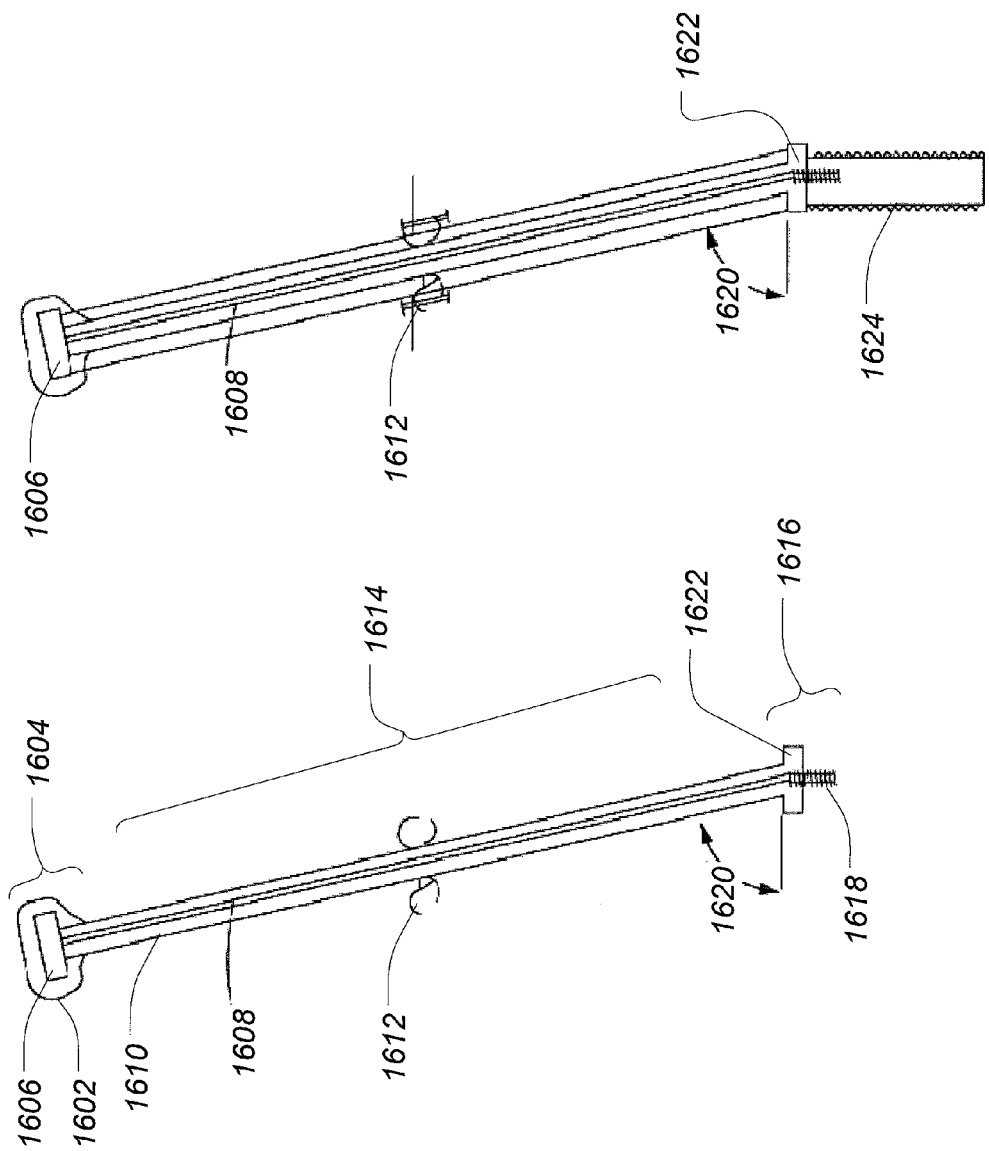

SPINAL FUSION CAGE WITH REMOVABLE PLANAR ELEMENTS

CROSS REFERENCE TO RELATED APPLICATIONS

This application is a continuation of U.S. patent application Ser. No. 13/277,272, filed Oct. 20, 2011, which is a continuation of U.S. patent application Ser. No. 12/367,487, filed on Feb. 6, 2009, which claims the benefit of priority from U.S. Provisional Patent Application Ser. Nos. 61/026,608 filed on Feb. 6, 2008, 61/055,399 filed on May 22, 2008 and 61/074,924 filed on Jun. 23, 2008, the entire disclosures of which are hereby incorporated by reference in their entireties.

FIELD OF THE INVENTION

The present disclosure relates to the field of medical devices and is generally directed toward an implantable intervertebral fusion cage that includes a removable means for retaining material inside of the cage during implantation as well as devices for properly aligning and implanting the intervertebral fusion cage into a patient, and methods of using the same.

BACKGROUND OF THE INVENTION

Spondylosyndesis, or spinal fusion, is a surgical technique used to combine two or more vertebrae into a single, rigid working unit. This is typically achieved by introducing a supplementary bone tissue, such as an autograft or allograft, into the intervertebral space between two target vertebrae, at the location that is typically occupied by an intervertebral disc. The supplementary bone tissue is then used in conjunction with the patient's natural osteoblastic processes in order to grow bone or osseous tissue between the two or more target vertebrae, which acts to fuse them together into the desired rigid unit. This procedure is used primarily to eliminate pain that is caused by abnormal motion of one or both of the target vertebrae; pain relief occurs by immobilizing the vertebrae themselves and preventing the abnormal motion. Alternatively, surgically implantable synthetic intervertebral fusion cages or devices may be used to perform spinal fusion procedures.

Surgically implantable intervertebral fusion cages are well known in the art and have been actively used to perform spinal fusion procedures for many years. Their use became popularized during the mid 1990's with the introduction of the BAK Device from the Zimmer Inc., a specific intervertebral fusion cage that has been implanted worldwide more than any other intervertebral fusion cage system. The BAK system is a fenestrated, threaded, cylindrical, titanium alloy device that is capable of being implanted into a patient as described above through an anterior or posterior approach, and is indicated for cervical and lumbar spinal surgery. The BAK system typifies a spinal fusion cage in that it is a highly fenestrated, hollow structure that will fit between two vertebrae at the location of the intervertebral disc.

When in use, a bone graft implant or synthetic fusion cage may be filled with an orthopedic matrix containing additional fusion-promoting material (FPM), for example including but not limited to calcium hydroxyapatite, bone morphogenic protein (BMP), demineralized bone matrix, collagen bone graft matrix (e.g. Formagraft®) and stem cell material (e.g. Osteocel®) or other fusion-promoting substance placed within the spaces of the implant. The implant is then implanted into a patient at the desired location along that patient's spine where it will serve to promote bone growth and, ultimately, fusion of the two target vertebrae. The fenestrations present in a typical intervertebral fusion cage allow the supplementary bone tissue to partially escape from the hollow interior of the cage and make sufficient contact with the target vertebrae, thereby promoting fusion of the target vertebrae through the fusion cage itself. Unfortunately, the fenestrations, which are essential for the proper functioning of the intervertebral fusion cages, also present a major problem during surgical implantation of the cage in that they are poor retainers of the FPM inside of the fusion cage during implantation because they cannot, and do not, retain the supplementary bone material inside of the fusion cage during implantation. The supplementary bone material typically used in conjunction with an intervertebral fusion cage may vary in viscosity, however one example of a FPM typically used in conjunction with an intervertebral fusion cage is a viscous liquid that does not move as freely as water, however it is sufficiently liquid in form so as to readily move from, or leak out of, the interior chamber of the fusion cage during implantation. Since this material is intended to promote the formation of bony tissue inside of a patient's body, a leak of this material out of the fusion cage during implantation can lead to the creation of bony structures or osseous tissue at a location away from the surgical site and in locations that can cause severe medical complications for the patient, such as heterotopic bone formation, nerve compression, failure to properly heal the fusion area between the two target vertebrae, and numerous other complications.

It would be advantageous to provide tools suitable for use with a surgically implantable intervertebral fusion cage that is adapted to and/or capable of retaining the FPM inside of the cage during implantation and/or thereafter, until such time as it is desirous for the FPM to come into contact with the target vertebrae, thereby preventing the material from flowing from, or moving out of, the interior of the fusion cage during implantation and thereby significantly reducing, if not eliminating, the risks noted above.

BRIEF SUMMARY OF THE INVENTION

Embodiments of the present disclosure provide a surgically implantable intervertebral fusion cage that is adapted to and/or capable of retaining material, and particularly supplementary bone material, and more particularly FPM, inside of the cage during implantation and/or thereafter, until such time as it is desirous for the supplementary bone material to come into contact with the target vertebrae, thereby preventing the material from flowing from, or moving out of, the interior of the fusion cage during implantation and thereby significantly reducing, if not eliminating, the risks associated with the known devices, noted above. The present disclosure provides for this type of fusion cage and tools for installing said cage, and therefore addresses and rectifies the problems associated with the prior art. Various embodiments of the present disclosure improve upon the known implantable intervertebral fusion cages and their use during surgical implantation. It is to be understood that the present disclosure includes a variety of different versions or embodiments, and this Brief Summary of the Invention is not meant to be limiting or all-inclusive. This Summary provides some general descriptions of some of the embodiments, but may also include some more specific descriptions of certain embodiments.

Other embodiments of the present invention provide a means of freely and readily removing the retaining means from the fusion cage after surgical implantation, and/or at any other desired time. In some embodiments, the present invention also includes methods of using and/or surgically implanting fusion cages of the present invention. Although well suited for use in human patients, and although much of the discussion of the present invention is directed toward use in humans, advantages offered by the present invention may be realized in the veterinary and scientific fields for the benefit and study of all types of animals and biological systems. Additionally, although the fusion cages of the present invention are particularly well-suited for implantation into the spinal column between two target vertebrae, and although much of the discussion of the present invention is directed toward their use in spinal applications, advantages offered by embodiments of the present invention may also be realized by implantation at other locations within a patient where the fusion of two or more bony structures may be desired. As one of skill in the art will appreciate, the present invention has applications in the general field of skeletal repair and treatment, with particular application to the treatment of spinal injuries and diseases. It should be appreciated, however that the principles of the present invention can also find application in other areas, specifically where there is a desire to constrain added fluid material to particular regions. For example, the present invention finds application in methods where the objective is to confine added material to predetermined areas of interest and to prohibit the undesired translocation of such material until an operation is complete and/or until a predetermined later time.

Embodiments of the present disclosure provide for an implantable intervertebral fusion cage that is capable of retaining material, and particularly supplementary bone material, within the interior chamber of the fusion cage during use, and particularly during surgical implantation, via the use of retaining means that serve to retain the supplementary bone material inside of the fusion cage. Other embodiments of the present disclosure provide a means of freely and readily removing the retaining means from the fusion cage after surgical implantation, and/or at any other desired time. In some embodiments, the present disclosure also includes methods of using and/or surgically implanting fusion cages of the present disclosure.

Certain embodiments of the present disclosure are directed toward a novel, implantable intervertebral fusion cage that includes at least one removable shield or shim that is capable of retaining a surgically useful material, such as a spinal fusion material, inside of the fusion cage during implantation and/or until the shield or shim is removed, and methods of using the same. Further embodiments of the present disclosure are directed toward a novel distraction wedge that is configured to prepare the desired site of surgical implantation to receive the fusion cage of the present disclosure. Additional embodiments of the present disclosure are directed toward a novel impactor/holder that is configured to properly align the fusion cage of the present disclosure at the desired site of surgical implantation and to implant the fusion cage therein. Additionally, the present disclosure provides for methods of surgically implanting a fusion cage into a patient, the methods including a novel means of preparing the patient for implantation.

Further embodiments of the present disclosure provide for a distraction wedge that is capable of creating an opening between two desired target structures, such as adjacent bones and/or vertebrae, at a desired surgical site, such opening being capable of receiving any fusion cage therein including, without limitation, the fusion cage of the present disclosure. In some embodiments, the distraction wedge has a head portion that is offset from the handle of the distraction wedge by an angle so that it may create the desired distraction or opening at the surgical site without the need for the distraction wedge to be aligned with the surgical site at a right angle.

Still other embodiments of the present disclosure provide for an impactor or holder that is capable of releasably securing embodiments of the spinal fusion cage to a distal end portion of the impactor or holder and delivering the fusion cage into a surgical site, while keeping the fusion cage secured to the distal end portion. The impactor or holder is also configured to release the fusion cage once it is in place at the desired surgical site. In some embodiments, the distal end portion of the impactor or holder is offset from the handle of the distracter or holder by an angle so that it may place the fusion cage into the desired surgical site without the need for the impactor or holder to be aligned with the surgical site at a right angle. In some embodiments, the impactor or holder is configured to deliver the fusion cage of the present disclosure into a desired surgical site and, after the fusion cage has been released from the distal end portion, to remove the retaining means from the fusion cage simultaneously with removal of the impactor or holder from the surgical pathway.

Still other embodiments of the present disclosure provide for a distraction wedge and/or an impactor or holder having an exterior shaft and a distally-located rotating hinge that is configured to allow the head portion of the distraction wedge and/or the distal end portion of the impactor or holder to rotate in at least one plane about an axis and thereby be offset from the handle of the distraction wedge and/or an impactor or holder, and from the exterior shaft, by any one of a number of angles. The rotating hinge thus allows the head portion of the distraction wedge and/or the distal end portion of the impactor or holder to be offset from the handle and from the exterior shaft by an angle so that they may be utilized as described herein without the need for the handle of the distraction wedge and/or an impactor or holder or for the exterior shaft to be aligned with the surgical site at a right angle. In some embodiments, the angle of the head portion of the distraction wedge and/or the distal end portion of the impactor or holder is determined by securing means located at the distal terminus of the external shaft, which are configured to lock the rotating hinge in place, and thereby set a desired angle of use for the head portion of the distraction wedge and/or the distal end portion of the impactor or holder. In further embodiments, the distally-located rotating hinge is configured to allow for rotation of the head portion of the distraction wedge and/or the distal end portion of the impactor or holder in three dimensions around a single fixed point, in a manner substantially similar to a wave platform shaker. In some embodiments, the retaining shims are capable of being removed from the fusion cage simultaneously with removal of the external shaft from the surgical pathway via securing means located along the exterior surface of the exterior shaft.

Although well suited for use in human patients, and although much of the discussion of the present disclosure is directed toward use in humans, advantages offered by the present disclosure may be realized in the veterinary and scientific fields for the benefit and study of all types of animals and biological systems. Additionally, although the fusion cages of the present disclosure are particularly well-suited for implantation into the spinal column between two target vertebrae, and although much of the discussion of the present disclosure is directed toward their use in spinal applications, advantages offered by embodiments of the present disclosure may also be realized by implantation at other locations within a patient where the fusion of two or more bony structures may be desired. As one of skill in the art will appreciate, the present disclosure has applications in the general field of skeletal repair and treatment, with particular application to the treatment of spinal injuries and diseases. It should be appreciated, however that the principles of the present disclosure can also find application in other areas, specifically where there is a desire to constrain added fluid material to particular regions. For example, the present disclosure finds application in methods where the objective is to confine added material to predetermined areas of interest and to prohibit the undesired translocation of such material until an operation is complete and/or until a predetermined later time.

As used herein, the term "shim" has a particular meaning within the art, but should also be understood to generally relate to any structure that acts as a barrier to the undesired translocation of material, and in particular, supplementary bone material and additional fusion-promoting material (FPM), whether it be synthetic or otherwise, for example including but not limited to calcium hydroxyapatite, bone morphogenic protein (BMP), demineralized bone matrix, collagen bone graft matrix (e.g. Formagraft®) and stem cell material (e.g. Osteocel®) or other fusion-promoting substance placed within the spaces of the implant, whether it be synthetic or otherwise. Shims can therefore be constructed of any suitable material, including resorbable material or non-absorbable material, dissolvable material, or other similar material and may have various desired physical attributes specifically adapted for particular applications, for example, being flexible, subject to having its physical properties modified by application of light, chemicals, porous, colored, radiopaque, etc. Moreover, the use of the term "cage" has a meaning understood in the art but may also be understood to generally relate to any geometrical structure, especially an enclosing structure, such as a box, rectangle, cylinder, or other physical configuration, that is adapted to constrain or confine material for desired periods of time within predetermined physical parameters.

In accordance with at least one embodiment of the present disclosure, an implantable intervertebral fusion cage is provided comprising a frame with at least one wall defining a hollow interior, the wall having at least one, and in some embodiments a plurality, of openings or fenestrations through it allowing for fluid communication between the hollow interior and the exterior of the cage, the wall further including at least one guiding structure located on an exterior surface of the wall that is configured to secure or hold one or more shields or shims in place along the exterior surface of the wall so as to cover the at least one, and In some embodiments a plurality, of openings. The guiding structure or ridge is configured so as to allow the shim to be freely removed from and replaced onto the exterior surface of the wall. When the shim is in place along the exterior of the cage and secured or held in place by the guiding structure, thereby at least partially covering the at least one opening, the shim substantially prevents or precludes fluid communication between the hollow interior and the exterior of the cage. When the shim is removed from the guiding structure and is no longer secured or held in place along the exterior surface of the wall, fluid communication is restored between the hollow interior and the exterior of the cage.

The intervertebral fusion cage of the present disclosure is typically geometrical in shape and/or design. In varying embodiments, the cage may be configured and/or shaped as a box, square, rectangle, tube, disc, rod, cylinder, cone, and/or cage and/or may also take on any one or more other shapes or configurations that may be useful in the fusion of two adjacent bony structures within a patient. In some embodiments, the shape of the cage is identical in size and shape to the head portion of a distraction wedge. Additionally, the intervertebral fusion cage of the present disclosure may be adapted to promote the fusion of the bony structures when situated between two bony structures of interest, or adjacent to them.

In accordance with other aspects of the present disclosure, an implantable intervertebral fusion cage is provided comprising a rectangular frame having a top wall, a bottom wall and four lateral walls, each lateral wall being connected to the top wall at a top edge and to the bottom wall at a bottom edge in such a way so as to form a hollow rectangular structure when the walls are interconnected. The top wall, bottom wall and the four lateral walls define a hollow interior of the cage when fully interconnected, and the top wall and the bottom wall each have at least one opening or fenestration through them allowing for fluid communication between the hollow interior and an exterior of the cage. The top wall and the bottom wall each further include at least one guiding structure located on the exterior surface of the top wall and the exterior surface of the bottom wall respectively, such guiding structures being configured to hold a first shim in place along the exterior surface of the top wall and a second shim in place along the exterior surface of the bottom wall. The guiding structures are configured to allow the first shim and the second shim to be freely removed from, and replaced onto, the exterior surface of the top wall and the exterior surface of the bottom wall, respectively. When the first shim is located along the exterior surface of the top wall and the second shim is in place along the exterior surface of the bottom wall of the cage, and held in place by a restraining means or preclusive barrier, which in one embodiment is the guiding structures, the first shim blocks the at least one opening or fenestration in the top wall of the case and the second shim blocks the at least one opening or fenestration in the bottom wall, thereby preventing fluid communication between the hollow interior and the exterior of the cage. When either the first shim or the second shim is, or both the first and second shims are, removed from the at least one guiding structure, fluid communication is at least partially restored between the hollow interior and the exterior of the cage. In some aspects of this embodiment of the present disclosure, the rectangular frame of the cage is square in shape.

In accordance with still other aspects of the present disclosure, an implantable intervertebral fusion cage is provided comprising a cylindrical, tubular or conical frame having a main wall, a first end wall and a second end wall, each end wall being interconnected to the main wall so as to form a closed cylinder, tube or cone when the walls are fully interconnected. The main wall, first end wall and second end wall, when fully interconnected, define a hollow interior of the cage. The main wall has at least one, and preferably a plurality, of openings allowing for fluid communication between the hollow interior and the exterior of the cage. The main wall further includes at least one guiding structure located on an exterior surface of the main wall that is configured to secure or hold a shim in place along the exterior surface. The at least one guiding structure is configured to allow the shim to be freely removed from, and replaced onto, the exterior surface of the main wall. When the shim is located along the exterior surface of the main wall and secured or held in place by the at least one guiding structure, the shim substantially covers or blocks the at least one opening and substantially prevents fluid communication between the hollow interior and the exterior of the cage. When the shim is removed from the at least one guiding structure, fluid communication is at least partially restored between the hollow interior and the exterior of the cage.

In accordance with still other aspects of the present disclosure, a method of surgically implanting an intervertebral fusion cage into a desired location within a patient is provided. In at least one embodiment of these aspects of the present disclosure, the method comprises obtaining a cage having: (i) at least one wall defining a hollow interior of the cage, the wall having at least one opening or fenestration in it that allows for fluid communication between the hollow interior and the exterior of the cage; (ii) at least one constraining structure, such as a guiding structure, on an exterior surface of the wall that is configured to reversibly hold at least one shim in place along the exterior surface of the wall, wherein the at least one guiding structure is configured to allow the at least one shim to be removed from, and replaced onto, the exterior surface of the wall; and (iii) at least one removable shim. The method further includes the surgeon or user preparing the cage for surgical implantation by filling the hollow interior with a material that is capable of fusing two vertebrae, or other bony structures, together and placing the at least one shim along the exterior surface of the cage such that the at least one shim is secured or held in place along the exterior surface by the at least one guiding structure and wherein the at least one shim substantially blocks the at least one opening or fenestration, thereby substantially preventing fluid communication between the hollow interior and the exterior of the cage and thereby retaining at least most of the material inside of the hollow interior. The method further includes locating an appropriate site inside of the patient for implantation of the cage and creating a surgical opening in the patient that is sufficient to accommodate the cage. After the opening is created, the method includes surgically implanting the cage into the patient in such a way that the fusion of the two vertebrae or other bony structures will occur upon exposure to the material. Thereafter, the at least one shim is removed from contact with the guiding structure and thus the exterior surface of the wall, restoring fluid communication between the hollow interior and the exterior of the cage and allowing the material to move from the hollow interior to the exterior of the cage. Once these tasks are completed, the method is concluded by closing the opening in the patient.

In accordance with still other embodiments of the present disclosure, a device is described that is directed to a spinal surgery graft containment device designed to contain the location of graft material in situ, or a method employing the same, including but not limited to a device or method that employs generally planar elements disposed on either side of a fusion implant having one or more apertures therein that can receive graft material.

In accordance with still other aspects of the present disclosure, a method of surgically implanting an intervertebral fusion cage into a desired location within a patient is provided. In at least one embodiment of these aspects of the present disclosure, the method comprises obtaining a cage having: (i) at least one wall defining a hollow interior of the cage, the wall having at least one opening or fenestration in it that allows for fluid communication between the hollow interior and the exterior of the cage; (ii) at least one constraining structure, such as a guiding structure, on an exterior surface of the wall that is configured to reversibly hold at least one shim in place along the exterior surface of the wall, wherein the at least one guiding structure is configured to allow the at least one shim to be removed from, and replaced onto, the exterior surface of the wall; (iii) at least one removable shim; and (iv) means for receiving a securing element capable of securing the cage to a distal end portion of an impactor or holder. The method also includes the surgeon or user preparing the cage for surgical implantation by filling the hollow interior with a material that is capable of fusing two vertebrae, or other bony structures, together and placing the at least one shim along the exterior surface of the cage such that the at least one shim is secured or held in place along the exterior surface by the at least one guiding structure and wherein the at least one shim substantially blocks the at least one opening or fenestration, thereby substantially preventing fluid communication between the hollow interior and the exterior of the cage and thereby retaining at least most of the material inside of the hollow interior. The method further includes locating an appropriate site inside of the patient for implantation of the cage, positioning the patient so as to obtain the desired amount of exposure of the desired surgical site, and creating a surgical opening in the patient that exposes the desired surgical site and that is sufficient to accommodate the cage. Once the opening is created, the method further includes generating a sufficient amount of distraction, or an opening of desired size and shape, at the surgical site by inserting a distraction wedge into the patient, contacting the distraction wedge with the tissue to be opened, and moving the distraction wedge into the tissue to be opened until the desired shape and depth of distraction, or opening, is created in the tissue to be opened. Thereafter, the method further includes surgically implanting the cage into the patient in such a way that the fusion of the two vertebrae or other bony structures will occur upon exposure to the material by securing the cage to a distal end portion of an impactor or holder, moving the cage and impactor or holder into the surgical opening and contacting the cage with the site of surgical implantation, and moving the cage into the surgical site. Thereafter, the cage is selectively released from the distal end portion of the impactor or holder and the impactor is removed from the surgical opening. In some embodiments of this method, the at least one shim is removed from contact with the guiding structure and thus the exterior surface of the wall, restoring fluid communication between the hollow interior and the exterior of the cage and allowing the material to move from the hollow interior to the exterior of the cage, simultaneously with the removal of the impactor or holder from the surgical opening. In other embodiments, the shim is removed after the impactor is removed from the surgical opening. Once these tasks are completed, the method is concluded by closing the opening in the patient.

Further aspects of the present disclosure include methods of preparing a patient for surgical implantation of a fusion cage, including the intervertebral fusion cage of the present disclosure. In some embodiments and referring specifically now to FIG. 12A, the patient is placed on his or her back, so that the surgical site has anterior exposure, providing access to the implant site through the abdomen. In yet another embodiment, the patient is placed on his or her front or abdomen, so that the implant site has posterior exposure, providing access to the implant site through the More preferably and referring specifically now to FIG. 12B, and in other embodiments, the patient is laterally positioned, or placed on his or her side, so that the portion of the intervertebral space into which a fusion cage is to be implanted is closer in proximity to the health care provider than if the patient were to be placed on his or her other side. The patient is then maximally bent laterally so that the side that is closer in proximity to the health care provider is maximally arched, with the other side being minimally arched. In this position, the health care provider uses a lateral or flank approach to access the implant site. In this way, the intervertebral space of interest is presented in as open a configuration as possible, thereby creating better access to the area of interest and decreasing the chance of creating surgical complications that can occur when the intervertebral space is not maximally presented as described above. This lateral or flank approach combined with certain aspects of the tool of the present disclosure, including the adjustability of the head portion of the tool allows a user or health care provider to gain access to and treat multiple vertebrae, implant sites, and surgical sites that were traditionally inaccessible with a lateral approach.

In one aspect of the present disclosure, a tool is provided for delivering or placing an intervertebral cage, graft, distraction wedge or other device into an implant or surgical site. The tool has a generally syringe-shaped handle and body, with, on the handle, a means for communicating with the distal end of the body. In one embodiment, the means for communication comprises a component manipulated by a surgeon's thumb during an operation. Such means may comprise a track ball, a rotating member, a lever, an electronically controlled signal, a button, or another structural feature that provides desired movement at the opposite end of the tool. In one such embodiment, a thumbscrew or thumbwheel is at the proximal end of the handle, and a hollow, cylindrical body is attached to the handle whereby the thumbscrew can rotatably communicate with the distal end of the body via a cable, shaft or other rotating means. The tool has a hinge on the distal end of the body that rotates in at least one axis that is substantially perpendicular to the axis of the cylindrical body, and that interconnects the body to the head of the tool. The hinge on the distal end provides articulation of the head with respect to the body of the tool. It should be understood that the hinge may be any rotating member that allows rotation in at least one plane between two parts.

The cylindrical body has at least one fastener, at a point between the proximal handle and the distal rotating member, that is capable of securing a tab, tether or other apparatus to the body of the tool. The fastener may be, for example, a clamp, a clip, a cam-lock or other similar device. In yet another aspect of the present disclosure, this fastener may be affixed, or it may be drawn towards the proximal handle, or it may be wound in order to draw in the tab, tether or other apparatus. Devices that may draw in the tab, tether or other apparatus are well known in the art. Incorporated by reference herein in their entireties are the following U.S. Patents and publications generally directed to reels and cam-locking devices that may be used to draw in the tab, tether or other apparatus of the present disclosure: U.S. Pat. No. 6,149,096 to Hartley, U.S. Pat. No. 4,039,156 to Abraham, U.S. Pat. No. 3,741,496 to Beller, U.S. Pat. No. 3,836,092 to Hull, U.S. Pat. No. 5,058,823 to Emura, U.S. Pat. No. 5,333,812 to Sato and U.S. Pat. No. 3,697,011 to Christensen.

The hinge on the distal end is capable of selectively locking (e.g., by a pin) the head into a particular position, e.g. so that a desired angle is created between the head and the body of the tool. The means for communication itself can be locked to alternatively achieve this objective. In one embodiment, when the rotating member is in an unlocked mode, the member is free to rotate in at least one plane. The selective locking mechanism can be remotely accessed by a user of the tool at the proximal end of the handle by, for example, an external shaft that communicates with the locking mechanism of the rotating member on the distal end of the body.

The head of the tool has a reversible fastening device (e.g., a threaded member) that is in rotatable communication with the means for communicating, for example, a thumbscrew, via the cable, shaft or other rotating means in the body. In one embodiment, the fastening device is used, by way of the thumbscrew, to secure components such as an intervertebral cage, graft or distraction wedge, that have corresponding and complementary fastening locations, to the head of the tool. Once the component is secured to the head of the tool, a tab, tether or other apparatus may be secured to the body of the tool using the at least one fastener. This assembly (See, e.g., FIG. 15) is now generally prepared for implantation or insertion into an implant site.

This tool (e.g. as pictured in FIGS. 14A and 14B) is preferably used with an implant device or graft that may need to be positioned into a joint space and thereafter released. Preferably, the tool is used to position the cage comprising removable veneers as described herein. This tool provides articulation of the head, and therefore the implant or graft, which allows a user to better position the implant or graft into the surgical site. This tool is also preferably used to attach tools to the head (e.g., a distraction wedge), whose angle with the body and handle may need to be periodically adjusted during a procedure. In particular, this tool is more preferably used with an intervertebral fusion device that has at least one shim or veneer with a tab or tether. The shim or veneer is used to cover a hole, aperture or fenestration that may be present in a wall of the fusion device. The tool is able to fasten to the fusion device, and the securing means is able to secure the tabs or tethers of the shims of the fusion device to the fastener on the body of the tool. In particular, a shim or veneer can be operatively associated with the tool as follows:

In use, once the fusion device is implanted into the desired implantation site, the user is able to engage the reversible fastening device via the means for communication, e.g. the thumbscrew, to release the fusion cage, and remove the tool from the surgical site, which will simultaneously remove the shim or veneer via the tab or tether. Prior art tools and cages are not designed to permit the insertion, as well as disengagement, of shims, veneers or the like from a surgical site upon completion of a fusion operation. In another more preferable use of the tool, the fastener on the cylindrical body is first used to retract, draw or wind the tab, tether or other apparatus to remove the shim or veneer to which the tab, tether or other apparatus is attached. Once the shim or veneer to which the tab, tether or other apparatus is attached is removed from the fusion device, the fusion device is selectively released by the user. The user may then remove the tool from the implant or surgical site, with the result being that only the implant device or graft remains in the patient, and the tool along with the shim or veneer and the associated tab, tether or apparatus is removed from the surgical site. Thus, using the present tool, a surgeon is able to ensure that the fusion device remains in its intended location within the patient as the shim or veneer is drawn from the surgical site and that any force imparted by the shim or veneer as it is being drawn does not cause an undue shift of the fusion device. Certain aspects of the present invention are thus directed to the use of a tool that facilitates the desired positioning of a cage, particularly one that comprises removable portions, such as veneers or shims, in such a manner that the desired position of the cage is not substantially altered when the removable portions are removed from the operation site. Prior art tools are mainly designed for the implantation and positioning of cages, but are not designed or suited for the selective removal of particular portions of new cages, such as the one described herein. Further, means for selective removal of particular portions of new cages, as described herein, are affixed to the body of the tool to provide reliable and consistent removal of the particular portions.

Yet another aspect of the present disclosure is that the impaction/distractor system can be variably angled to allow for a variety of insertion angles. A ratcheting adapter can be fitted to allow for this application. Furthermore, the present invention can be used in veterinary conditions, in the thoracic spine or can be used for insertion of a laterally based disk replacement.

Yet another aspect of the present disclosure is that it can be used as an intervention for the approach to the traumatically damaged spine, spinal deformity or reconstruction for tumor destruction. Angled cages can be applied to correct deformity at the disk space or replace vertebrae that require removal.

Incorporated by reference in their entireties are the following U.S. Patents and publications directed generally to methods and apparatus related to spinal procedures, thus providing written description support for various aspects of the present disclosure. The U.S. Patents and publications fully incorporated herein by reference are as follows: U.S. Pat. No. 7,481,766 to Lee et al., U.S. Pat. No. 7,442,208 to Mathieu et al., U.S. Pat. No. 7,429,270 to Baumgartner et al., U.S. Pat. No. 7,371,239 to Dec et al., U.S. Pat. No. 7,361,178 to Hearn et al., U.S. Pat. No. 7,357,804 to Binder et al., U.S. Pat. No. 7,238,203 to Bagga et al., U.S. Pat. No. 7,223,292 to Messerli et al., U.S. Pat. No. 6,974,480 to Messerli et al., U.S. Pat. No. 6,730,125 to Lin, U.S. Pat. No. 6,673,113 to Ralph et al., U.S. Pat. No. 6,500,206 to Bryan, U.S. Pat. No. 6,454,806 to Cohen et al., U.S. Pat. No. 6,245,108 to Biscup, U.S. Pat. No. 6,146,420 to McKay, U.S. Pat. No. 5,782,919 to Zdeblick et al., U.S. Pat. No. 5,541,191 to Lahille et al., U.S. Pat. No. 5,055,104 to Ray, U.S. Pat. No. 5,688,285 to Yamada, U.S. Pat. No. 5,290,295 to Querals, U.S. Patent Publication 2008/0033440 to Moskowitz et al., U.S. Patent Publication 2007/088007 to Burkus et al., U.S. Patent Publication 2007/0208423 to Messerli et al., U.S. Patent Publication 2004/0034430 to Falahee, and U.S. Patent Publication 2004/0153158 to Errico et al. and U.S. application Ser. No. 11/093,409 filed Mar. 29, 2005.

Though the description of the disclosure includes descriptions of one or more embodiments and certain variations and modifications, other variations and modifications are to be understood as being within the scope of the invention, e.g., as may be within the skill and knowledge of those in the art, after understanding the present disclosure. The inventor intends to obtain rights which include alternative embodiments to the extent permitted, including alternate, interchangeable and/or equivalent structures, functions, ranges or steps to those explicitly described and/or claimed, whether or not such alternate, interchangeable and/or equivalent structures, functions, ranges or steps are explicitly disclosed herein, and without intending to publicly dedicate any patentable subject matter.

Various embodiments of the present disclosure are set forth in the attached figures and in the Detailed Description as provided herein and as embodied and/or exemplified by the claims. It should be understood, however, that this Summary does not contain all of the aspects and embodiments of the present invention, is not meant to be limiting or restrictive in any manner, and that the invention as disclosed herein is and will be understood by those of ordinary skill in the art to encompass obvious improvements and modifications thereto and those improvements and modification that are within the skill and knowledge of those in the art.

Additional advantages of the present invention will become readily apparent from the following discussion, particularly when taken together with the accompanying drawings.

BRIEF DESCRIPTION OF THE DRAWINGS

Many advantages of the present invention will be apparent to those skilled in the art with a reading of this specification in conjunction with the attached drawings, wherein:

FIGS. 7A, 7B and 7C show two views of an embodiment of a cage having two guiding structures on a top external surface and two guiding structures on a bottom external surface of the cage according to at least some embodiments of the present disclosure;

FIG. 12A is a side view of a posteriorly positioned patient according to at least some embodiments of the present disclosure, in the depicted scene, a distraction wedge according to at least some embodiments of the present disclosure is shown in place between vertebrae L4 and L5;

FIGS. 13A and 13B show two views of an impactor or holder according to at least some embodiments of the present disclosure.

Figure 1A:
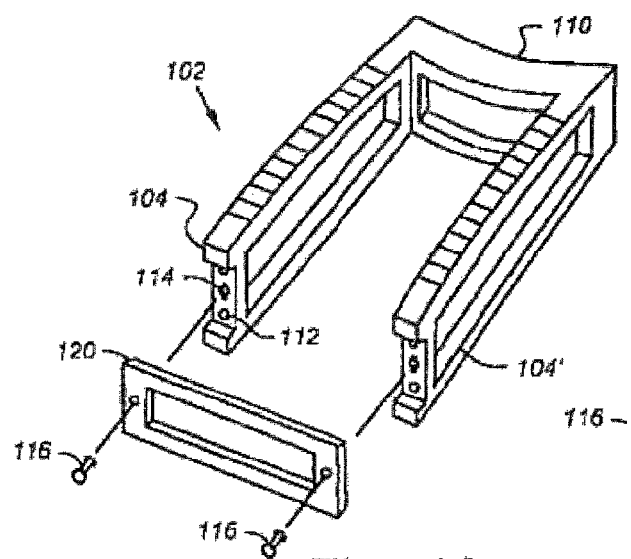
FIG. 1A shows a known rectangular intervertebral fusion cage present in the prior art.
Figure 1B:
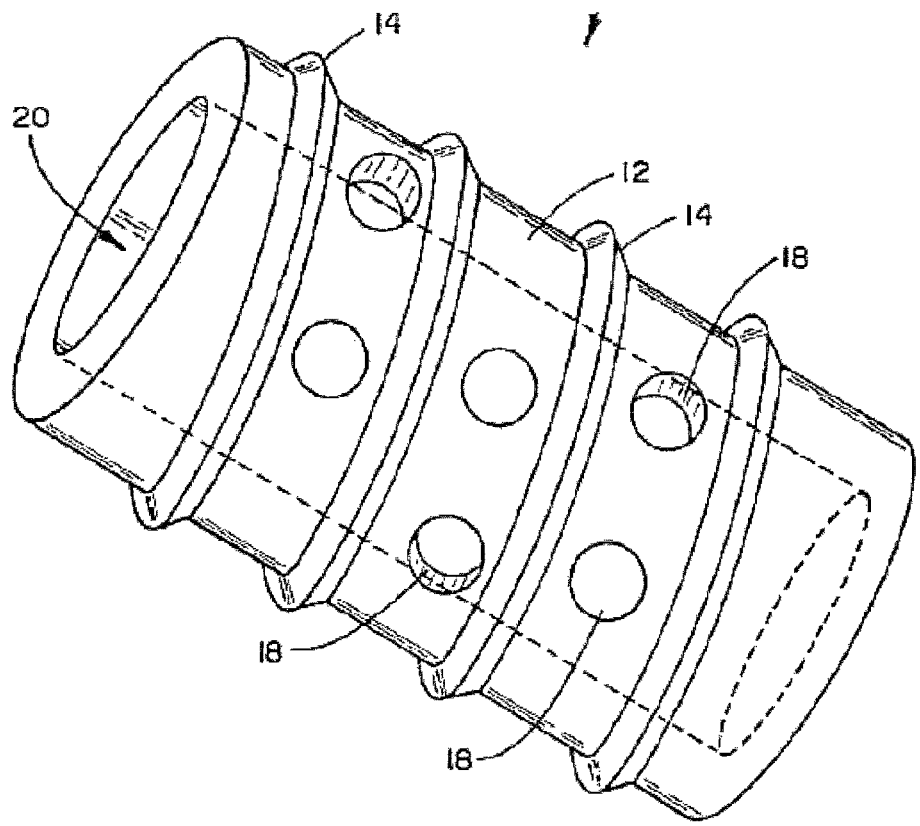
FIG. 1B shows a known cylindrical intervertebral fusion cage present in the prior art.

The drawings are not necessarily to scale and the drawings may include exaggerated features for purposes of clarity.

DETAILED DESCRIPTION

This Detailed Description is being provided with simultaneous reference to all of the attached figures. The present disclosure provides for an implantable intervertebral fusion cage that is capable of retaining material, and particularly supplementary bone material and more particularly FPM, within an interior chamber of the fusion cage during use and/or during surgical implantation via the use of retaining means that serve to hold the supplementary bone material or FPM inside of a hollow chamber of the fusion cage. The present disclosure also provides for at least one means of removing the retaining means from the implantable fusion cage upon implantation of the cage, or at any other desired time. The present disclosure therefore improves upon all of the known surgically implantable intervertebral fusion cages present in the prior art by including at least one shield or shim that is held along at least one exterior surface of an intervertebral fusion cage and that serves to at least partially, preferably at least substantially, and even more preferably completely, block the movement of material from the hollow interior chamber of the cage to the exterior of the cage until such time as it is desirous for such movement to occur. The at least one shim is freely removable and may be put into place and removed from the cage numerous times with no loss of function. The at least one shim is held in place along the exterior of the intervertebral fusion cage by at least one guiding structure, located along an external surface of the cage, that overlaps with at least a portion of at least one edge of the shim so as to secure the shim in place on the external surface and prevent the shim from moving or migrating during use and/or implantation of the cage. The contact of the at least one guiding structure with the at least one shim is therefore sufficient to hold the shim in place during use and/or implantation of the cage and to prevent fluid communication between the interior and the exterior of the cage, but is also operable to allow the shim to be freely removed from, and/or replaced onto, the cage. It is intended in some embodiments that the shim of the present disclosure be freely removable from the guiding structure by the user or health care provider implanting the cage, but that the at least one shim be held in place by the at least one guiding structure sufficiently tightly so as to prevent any unintended movement or shifting during surgical implantation of the cage and therefore prevent fluid communication between the hollow interior chamber and the exterior of the cage. One having skill in the art will appreciate that the shim may be a film, a laminate, a veneer, a wedge, a section, a segment, a shim, a plug, a coating, a surface, a plate and a cover that is operable to engage at least one exterior surface of an intervertebral fusion cage, and operable to at least partially, preferably at least substantially, and more preferably completely, block the movement of material from the hollow interior of the cage to the exterior of the cage. For ease of explanation, and without meaning to unduly restrict the invention, throughout this description the use of a singular term, such as shim, veneer, etc. will be generally understood to refer to one of the several embodiments of the invention.

Information relevant to the current state of the art as it applies to surgically implantable intervertebral fusion cages, including useful written, enabling descriptions of how to make and use various components, can be found in the following U.S. Patents and U.S. Patent Publications, the entire contents of which are incorporated herein by this reference: U.S. Pat. No. 5,653,763 to Errico et al.; U.S. Pat. No. 5,665,122 to Kambin; U.S. Pat. No. 5,888,228 to Knothe et al.; U.S. Pat. No. 6,090,143 to Meriwether et al.; U.S. Pat. No. 6,159,245 to Meriwether et al.; U.S. Pat. No. 6,648,915 to Sazy; U.S. Pat. No. 6,699,288 to Moret; U.S. Pat. No. 7,094,257 to Mujwid et al.; U.S. Pat. No. 7,135,043 to Nakahara et al.; U.S. Pat. No. 7,232,463 to Falahee; U.S. Patent Application Publication No. 2003/0083748 to Lee et al.; U.S. Patent Application Publication No. 2004/0143330 to Sazy; U.S. Patent Application Publication No. 2004/0162618 to Mujwid et al.; U.S. Patent Application Publication No. 2005/0149192 to Zucherman et al.; U.S. Patent Application Publication No. 2005/0149193 to Zucherman et al.; U.S. Patent Application Publication No. 2005/0283236 to Razian; and U.S. Patent Application Publication No. 2007/0270951 to Davis et al.

In accordance with at least some aspects of at least one embodiment of the present disclosure, a surgically implantable intervertebral fusion cage is provided. The fusion cage includes a frame with at least one wall defining a hollow interior within the frame, the at least one wall having sufficient structural stability so as to withstand surgical implantation in a patient and to withstand the physical stresses that it will encounter after implantation as the patient moves. Although not required in the present disclosure, in some embodiments, the walls that comprise the cage will be generally planar elements. Generally planar is meant to mean relating to, or lying in a plane. A plane is a three-dimensional surface where, for any two points, a straight line joining the two points will lie wholly inside the surface. One having skill in the art will appreciate that the generally planar elements may be any structure or device that is capable of spanning two lines in space, and may be made of a material and configured to be structurally capable of resisting deformation substantial plastic deformation under forces including stress, strain and compression. A shim of certain embodiments of the invention may have one or more planar elements, especially when a corresponding cage structure has more than one surface to be contacted with a shim While it is not required for purposes of the present disclosure, in some embodiments the cage will have a plurality of walls defining the hollow interior such that the cage may take the shape of a rectangle, square, box, tube, cylinder, cone, polygon, or other shape suitable for implantation into a patient. The at least one wall has at least one, and in some embodiments a plurality, of openings, apertures or fenestrations through it that provide open access to the hollow interior of the fusion cage and that allow for fluid communication between the hollow interior of the cage and the exterior of the cage. These openings, apertures and/or fenestrations serve the purpose of allowing a supplementary bone material, such as a bone grafting material, or FPM, which is inserted into the hollow interior prior to surgical implantation, to leave the hollow interior of the cage, make contact with the desired vertebrae or other bony structures, and promote the fusion of the two vertebrae or other bony structures. Further, one having skill in the art will appreciate that as used herein, an opening, aperture and/or fenestration through the wall may be a perforation, a slot, a gap, a hole, a cavity, a notch or other breach in the wall that enables fluid communication between the hollow interior of the cage and the exterior of the cage. Further, the openings, apertures and/or fenestrations need not necessarily permit an unobstructed straight path from a point in the hollow interior of the cage to a point in the exterior of the cage (e.g., the wall may be comprised of a plurality of layers, wherein each layer has at least one opening aperture and/or fenestration, and the openings, apertures and/or fenestrations are offset and non-overlapping).

The at least one wall further includes at least one guiding structure located on an exterior surface of the at least one wall such that the at least one guiding structure is located on an exterior surface of the cage relative to the hollow interior. The at least one guiding structure functions to hold at least one shim to the exterior surface of the cage and is preferably configured so as to hold the shim against the exterior surface of the cage sufficiently tightly so as to at least substantially block the fluid communication between the hollow interior of the cage and the exterior of the cage while the shim is in place. The at least one guiding structure is also configured so as to allow the shim to be removed at any time it is desirous for the user to do so, such as after surgical implantation. In some embodiments, when the shim is held in place along the exterior surface by the at least one guiding structure, the shim serves to at least partially, and preferably completely, cover or block the at least one opening or fenestration in the wall, thus preventing fluid communication between the hollow interior and the exterior of the cage and thereby preventing the movement of material out of the hollow interior. Therefore, when the shim is removed from contact with the guiding structure and the exterior surface of the cage, fluid communication is restored between the hollow interior and the exterior of the cage and material will be free to move from the hollow interior to the exterior of the cage.

In another embodiment of the present disclosure, the at least one wall may be comprised of a plurality of generally parallel, planar walls, each wall in the plurality having at least one opening, aperture and/or fenestration. The resulting structure would have at least one interior wall and at least one exterior wall creating a substantially planar space between the two walls. The substantially planar space may be configured to hold at least one shim against one of the exterior surface of the inner wall and the interior surface of the outer wall. The substantially planar space and the shim are preferably configured so as to hold the shim against one of the inner and outer wall sufficiently tightly so as to at least substantially block the fluid communication between the hollow interior of the cage and the exterior of the cage while the shim is in place. As in the foregoing paragraph, the substantially planar space and the shim are configured so as to allow the shim to be removed at any time it is desirous for the user to do so, such as after surgical implantation.

In accordance with at least some aspects of at least one embodiment of the present disclosure, a surgically implantable intervertebral fusion cage is provided, the cage having a hollow frame that is substantially rectangular or square in shape. For purposes of illustration, and without wishing to be held to any one embodiment, the following U.S. Patents and U.S. Patent Publications are incorporated herein by this reference in order to provide an illustrative and enabling disclosure and general description of an intervertebral fusion cage that is substantially rectangular or square in shape: U.S. Pat. No. 5,653,763 to Errico et al.; U.S. Pat. No. 5,665,122 to Kambin; U.S. Pat. No. 5,888,228 to Knothe et al.; U.S. Pat. No. 6,090,143 to Meriwether et al.; U.S. Pat. No. 6,159,245 to Meriwether et al.; U.S. Pat. No. 6,699,288 to Moret; U.S. Pat. No. 7,094,257 to Mujwid et al.; U.S. Pat. No. 7,135,043 to Nakahara et al.; U.S. Pat. No. 7,232,463 to Falahee; U.S. Patent Application Publication No. 2003/0083748 to Lee et al.; U.S. Patent Application Publication No. 2004/0162618 to Mujwid et al.; and U.S. Patent Application Publication No. 2005/0283236 to Razian. Each of the foregoing discloses cages that have the same basic square or rectangular construction and, for the sake of simplicity, will be collectively referred to herein as having a top wall, a bottom wall and four lateral walls which collectively form the shape of a rectangle or square in that each lateral wall is connected to a single edge of the top wall at a top edge of the lateral wall and the bottom edge of the lateral wall is connected to a single edge of the bottom wall in such a way that the top wall, bottom wall and four lateral walls, when fully interconnected, create a shape that is substantially rectangular or square-shaped and also define a hollow interior to the cage. In some embodiments, additional walls may be present, for example within the interior chamber of the cage in order to create at least two separate hollow interior chambers within the cage and the guiding structures and shims of the present disclosure will operate identically with these embodiments with no loss of function whatsoever.

The intervertebral fusion cage has a height ranging from about 8 mm to about 18 mm, a width ranging from about 10 mm to about 12 mm, and a length ranging from about 18 mm to about 55 mm. Thus, both the top and bottom walls preferably have a length that ranges from about 18 mm to about 40 mm and a width ranging from about 10 mm to about 12 mm, and each of the lateral walls have a length that ranges from about 18 mm to about 40 mm and a width ranging from about 8 mm to about 18 mm. When fully constructed, the substantially rectangular or square shaped cages have a flat profile such that they are longer and wider than they are tall, making the largest points of contact of the cage with the target vertebrae the exterior surface of the top wall and the exterior surface of the bottom wall. The lateral walls may also make contact with the target vertebrae, though it is preferable that the major points of contact with the target vertebrae will occur via the exterior surface of the top wall and the exterior surface of the bottom wall.

Both the top wall and the bottom wall have at least one opening or fenestration, and preferably a plurality of openings or fenestrations, that provide a location, or locations, where material, that is placed or stored inside of the hollow interior, may freely move from the hollow interior to the exterior of the cage. The at least one opening or fenestration, and preferably a plurality of openings or fenestrations, thus allow for fluid communication between the hollow interior of the cage and the outside of the cage. The purpose of these openings or fenestrations is to provide a means by which a portion of a material, such as supplementary bone material or bone grafting material, that is placed inside of the hollow interior of the cage prior to implantation, may escape from the hollow interior and make contact with the target vertebrae, at the top of the cage and at the bottom of the cage, while retaining a portion of the material inside of the hollow interior. In this way, the material makes contact with one of the target vertebrae at the exterior surface of the top wall of the cage and makes contact with another of the target vertebrae at the exterior surface of the bottom wall of the cage, while at the same time there is sufficient material remaining inside of the hollow interior so as to promote the fusion of the target vertebrae by the generation of bony or osseous tissue through and around the fusion cage.

Figure 3B:
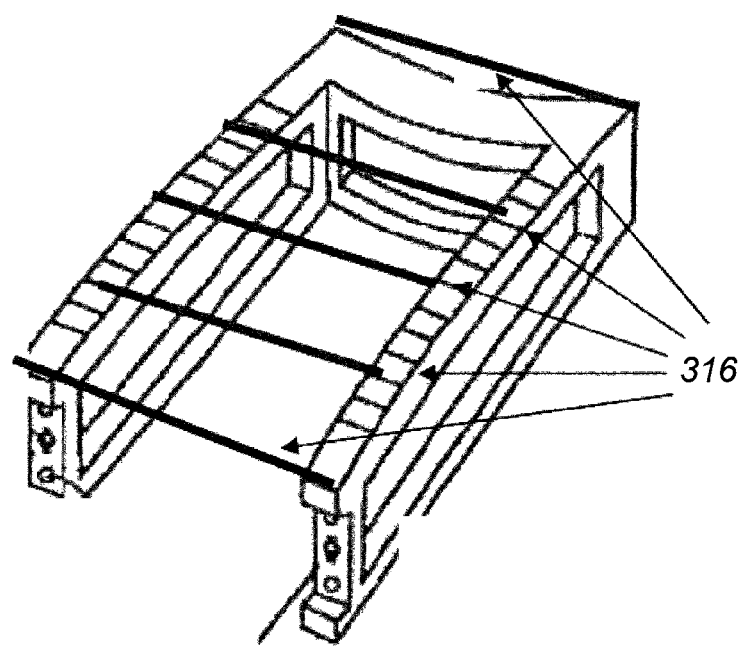
Figure 4:
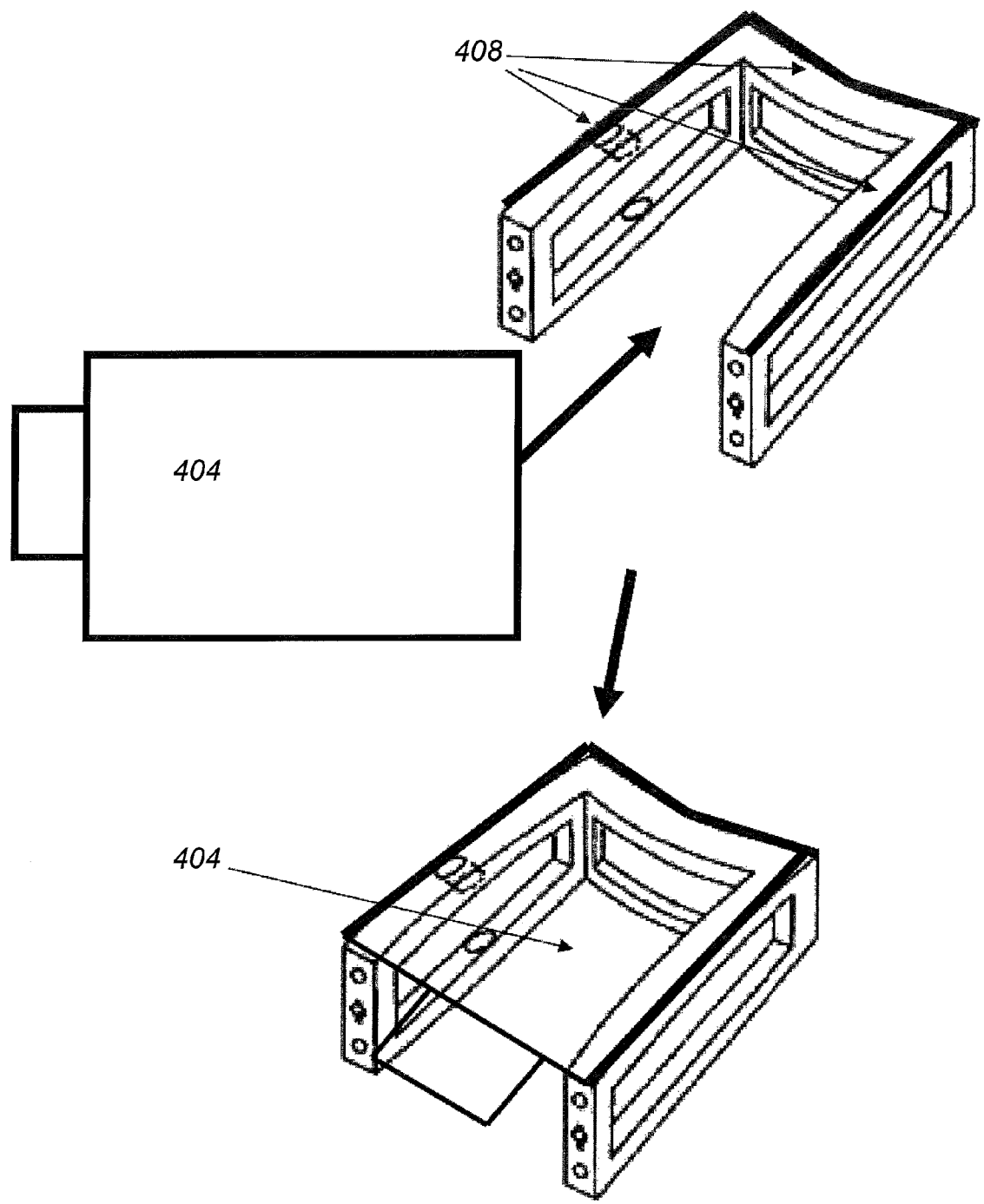
FIG. 4 shows an intervertebral cage according to at least some embodiments of the present disclosure with a removable shim being placed along an external surface of the cage.
Figure 9:
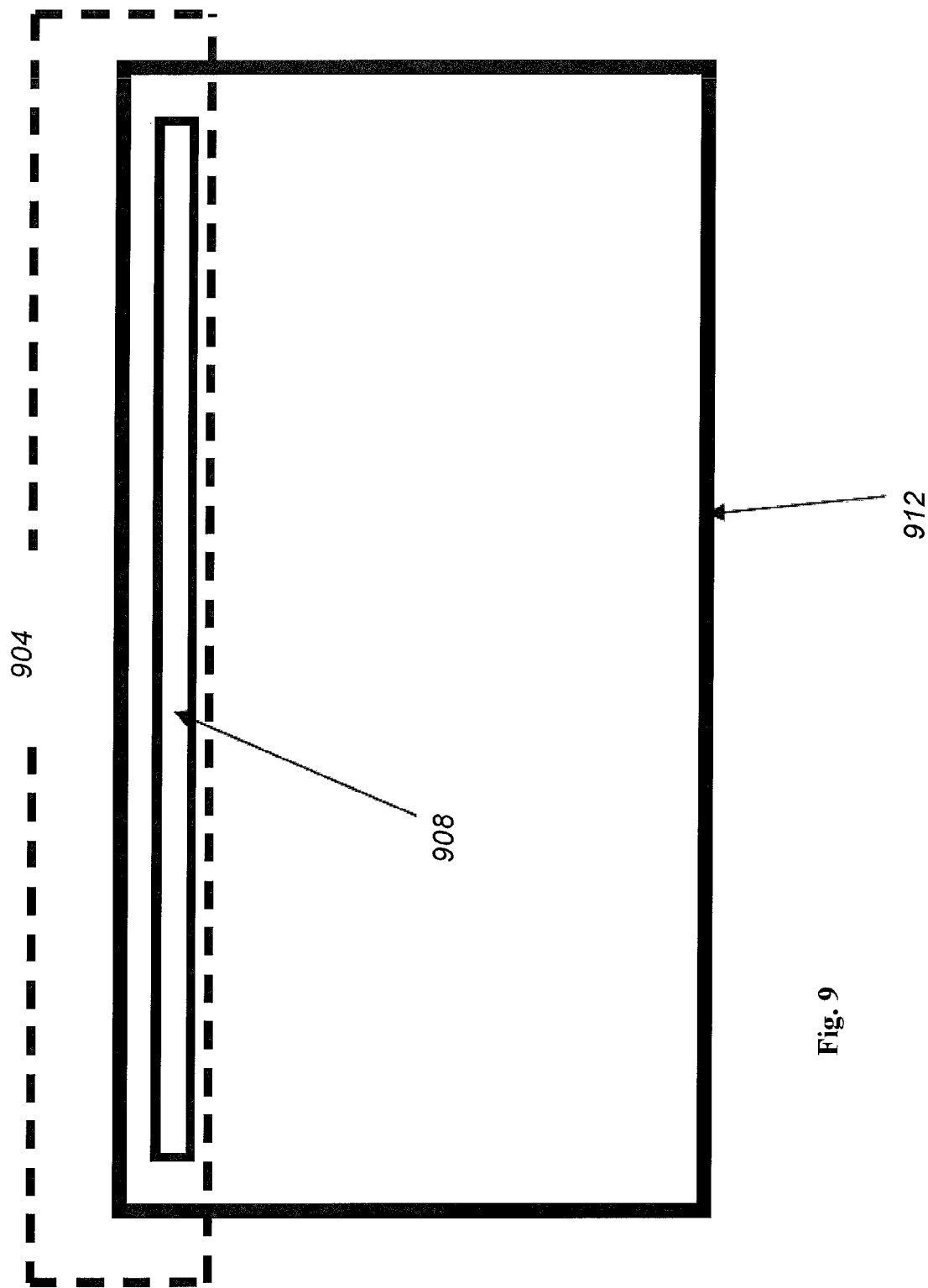
FIG. 9 is an end view of the cage of FIG. 3B according to at least some embodiments of the present disclosure.

Additionally, at least one of the exterior surface of the top wall or the exterior surface of the bottom wall has at least one, and in some embodiments two, three, or more, guiding structures located on it, which is configured to hold a shield or shim in place along the exterior surface of the wall in question. In some embodiments, the guiding structure is present on three, and even more preferably two, of the edges of the exterior surface such that the shield or shim is held in place by the guiding structure along at least two, and in some embodiments three, sides of the exterior surface of the wall in question. In some embodiments, the external surface has a plurality of guiding structures located on it and there may be two guiding structures along two opposing edges of the external surface such that the shim is held in place along two opposing edges of the external surface, or there may be three separate guiding structures located along the same edges of the exterior surface as previously described for the continuous guiding structure, such that the shim is held in place along three sides by three separate guiding structures. Referring now specifically to FIG. 4, a shim 404 is shown that is held in place by three guiding structures 408 along the exterior surface of a wall. In still other embodiments and referring specifically to FIG. 3B, there are a plurality of guiding structures 316 holding the shim in place, some located along the edges of the external surface as previously described and at least one located in a belt-like fashion across the external surface and spanning the distance from one wall to an opposing wall (e.g., from the top wall to the bottom wall) such that the shim is positioned between the belt-like guiding structure and the exterior surface of the wall, and is held in place along the exterior surface by the belt-like guiding structure accordingly. Referring specifically now to FIG. 9, a side aspect view of a cage is shown illustrating a belt ridge and the slot created by the ridge through which the shim is held in place. In those embodiments using belt-like guiding structures, it is preferable for a plurality of belt-like guiding structures 316 to be present.

In some embodiments, it is preferable for at least one guiding structure to be located along both the exterior surface of the top wall and the exterior surface of the bottom wall so that a first shim may be held in place by at least one guiding structure along the external surface of the top wall and a second shim may be held in place by at least one guiding structure along the external surface of the bottom wall. As mentioned above, the top and bottom walls have the at least one, and preferably a plurality of, openings or fenestrations through them that allow for the movement of material out of the hollow interior and toward the target vertebrae. Therefore, when a first shim is held in place by at least one guiding structure along the exterior surface of the top wall and a second shim is held in place by at least one guiding structure along the exterior surface of the bottom wall, the first shim and the second shim at least partially block or cover, and preferably completely block or cover, the at least one opening or fenestration located along and through the top and bottom walls. When the at least one opening or fenestration is covered or blocked in this manner, the shims serve to prevent the movement of material, such as supplementary bone material or bone grafting material, from the hollow interior to the exterior of the cage. The shims thus serve to prevent or block the fluid communication that would otherwise exist between the hollow interior and the exterior of the cage. Therefore, when either the first shim or the second shim is, or both the first and second shims are, removed from contact with the guiding structures located along the external surfaces of the top wall and the bottom wall, fluid communication is restored between the hollow interior and the exterior of the cage and the material may move from the hollow interior through the at least one opening or fenestration to the outside of the cage.

It is also preferable for the at least one guiding structure to be configured to hold or retain the shim(s) in place along the external surface in question sufficiently tightly so as to prevent the movement of material from the hollow interior to the outside of the cage. It is thus another aspect of the present disclosure for the at least one guiding structure to hold the shim(s) in place along, and in direct contact with, the external surface of the wall in question so that the shim(s) lies flat, without any wrinkles or gaps, and such that the shim(s) is held in contact with the external surface so as to prevent the movement of a substantial amount of a free flowing fluid, such as water, from the hollow interior to the outside of the cage, and to completely prevent the movement of a more viscous material, such as a supplementary bone material or bone grafting material, from the hollow interior to the outside of the cage. It is also an aspect of the present disclosure for the at least one guiding structure to be configured to allow the shim(s) to be freely removable from the external surface of the wall in question and replaceable onto the external surface of the wall in question numerous times with no loss of function whatsoever. It is therefore preferable for the at least one guiding structure to be configured so as to allow the shim(s) to move into and out of place along the external surface a plurality of times and to still hold the shim(s) in place sufficiently snugly to at least substantially prevent the movement of a viscous material from the hollow interior to the outside of the cage.

Figure 2A:
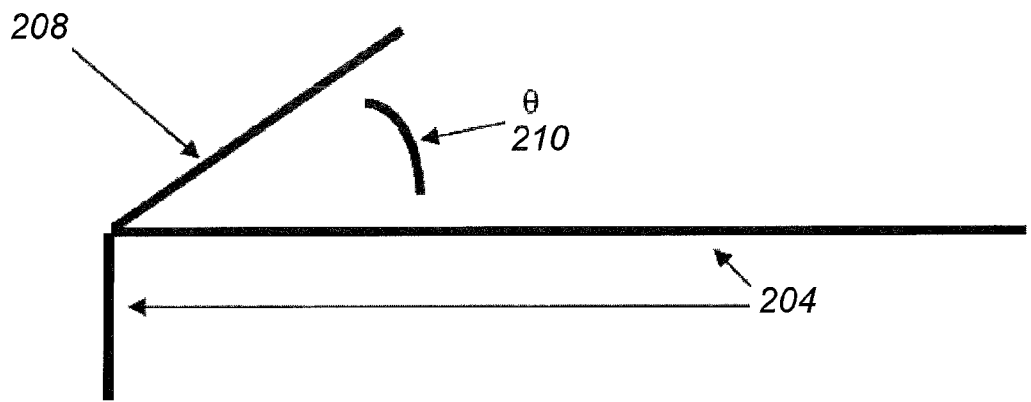
FIGS. 2A and 2B show two embodiments of a guiding structure according to at least some embodiments of the present disclosure.

The at least one guiding structure may be configured in any number of manners that will allow the guiding structure to hold the shim snugly to the external surface and to allow for the free removal and replacement of the shim numerous times with no loss in function. In some embodiments and referring specifically to FIG. 2A, the guiding structure 208 is a single projection that extends outward from the external surface of the wall in question at an angle θ210 such that the shim slides under the guiding structure and is held in place until such time as the shim is removed from under the guiding structure 208. In these embodiments, the guiding structure 208 extends outward from the external surface at an angle that may be configured to fit a specific shim, and/or at an angle θ210 ranging from about zero degrees to about 45 degrees, or more preferably from about 15 degrees to about 35 degrees. In these embodiments, the shim is held in place under the guiding structure 208 strictly by the angle 210 of the guiding structure, which makes contact with the shim along the underside of the guiding structure and holds the shim snugly to the external surface or cage wall 204.

Figure 2B:
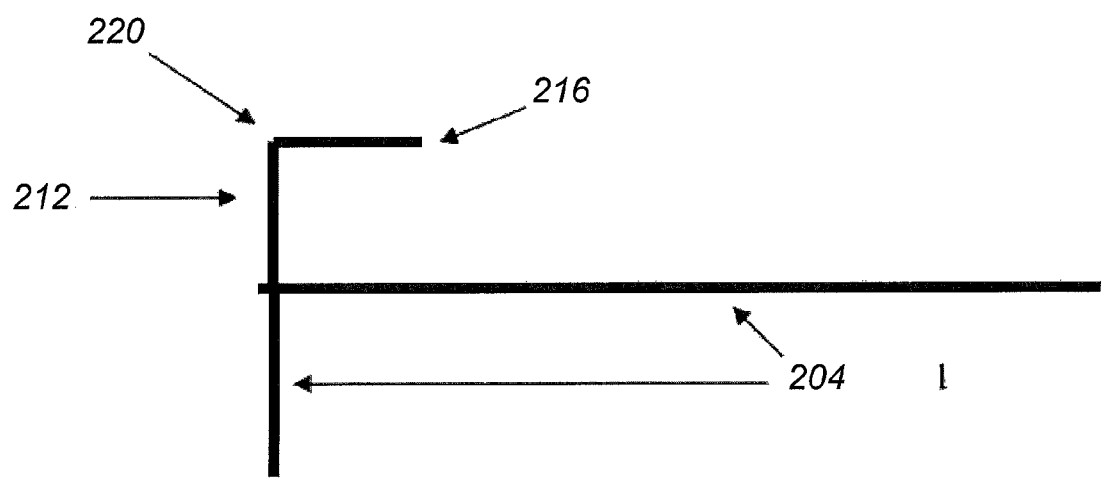
Figure 5A:
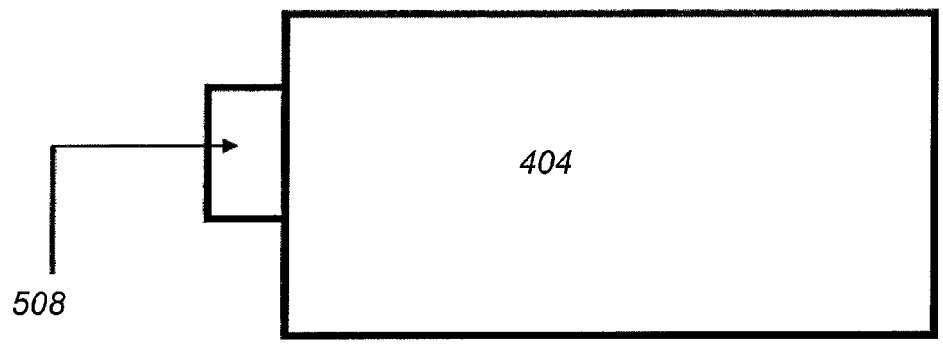
FIG. 5A shows an embodiment of the removable shim according to at least some embodiments of the present disclosure.
Figure 5B:
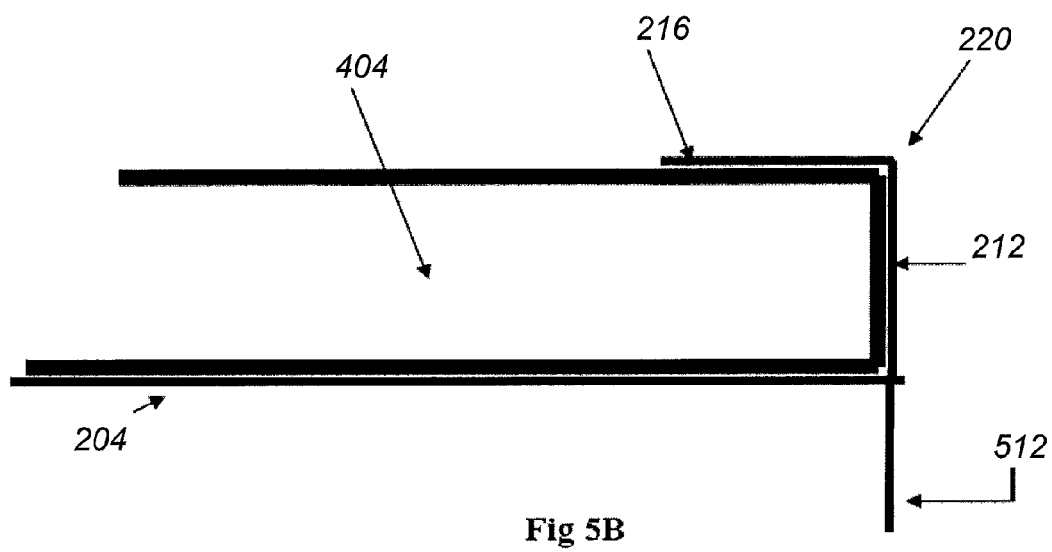
FIG. 5B shows a close up of a removable shim in contact with an external surface of a cage and held in place by a guiding structure according to at least some embodiments of the present disclosure.

In other embodiments and referring specifically to FIGS. 2B and 5B, the guiding structure is comprised of a projection of the following general configuration:

In these embodiments, the bottom portion 212 of the guiding structure 220 shown above projects straight up and outward from the cage wall 204 or external surface 512 of the cage, and the upper portion, or overhang 216, extends perpendicularly to the bottom portion 212 and projects toward the center of the external surface in such a way so that the shim slides under the overhang 216 of the guiding structure 220 and is held in place by the guiding structure by making contact with the bottom portion 212, overhang 216 and external surface 204 of the cage. The overhang portion 216 of this embodiment may vary in angle, though it is preferable that the overhang portion 216 be at a 90 degree angle from the bottom portion 212.

Figure 3A:
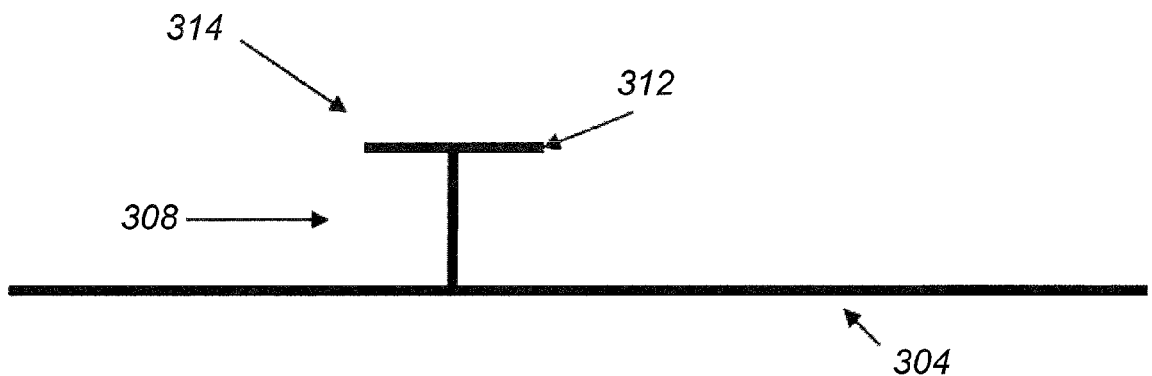
FIGS. 3A and 3B show two additional embodiments of a guiding structure according to at least some embodiments of the present disclosure.

In still other embodiments and referring specifically to FIG. 3A, the guiding structure 314 may be configured to secure a shim on two sides. The guiding structure of these embodiments has the following general configuration:

T

In these embodiments, the bottom portion 308 of the guiding structure 314 shown above projects straight up and outward from the external surface 304 and the upper portion, or crossbar 312, projects outward from the bottom portion in two directions, so that a shim can slide under either side of the crossbar 312 of the guiding structure 314 and be held in place by the crossbar 312. It is preferable for the crossbar 312 portion of these embodiments to be at a 90 degree angle, or perpendicular, from the bottom portion 308. These embodiments of the guiding structure are particularly useful with cages of a round or cylindrical configuration, as described below, though they may also be used in any of the embodiments of the present disclosure disclosed herein.

The shim may be configured to be used with any number of cage configurations, shapes and sizes. For example, and without wishing to be limited to any one embodiment, the shim may be of a generally rectangular or square configuration and thus operable with the rectangular or square embodiments of the cage of the present disclosure described above. Additionally, the shim may be shaped in a cylindrical, tubular, conical, circular, arced or rounded manner so as to be operable with the cylindrical or rounded embodiments of the cage of the present disclosure described below. For purposes of the present disclosure, the shim may be of any shape and/or size desired including, without limitation, square, rectangular, triangular, round, circular, tubular, cylindrical, polygonal, conical, and any other shape that may be of use with an implantable intervertebral fusion cage of the present disclosure. It is yet another embodiment of the present disclosure that the shim comprise multiple sides or multiple members—for example, the shim may have a top member and at least one side member, wherein the at least one side member is operable to contact or otherwise reversibly engage the openings or fenestrations of the cage and serve to substantially block fluid communication between the hollow interior and the exterior of the cage. In yet another embodiment, the shim may be comprised of a plurality of members that are interconnected by a connecting member including, for example, a wire, a cable and another member. One having ordinary skill in the art will appreciate that a shim that is configured to lie in more than one plane (i.e., have more than one member or have a curvature) may additionally be configured to reversibly self-adhere, attach, engage, slide, assemble or clamp onto the cage of the present disclosure. This self-adhering or clamping aspect may be achieved by mechanical means (e.g., by frictional force, compressive force), electrical means (e.g., piezo-electric device), or magnetic force. This self-adhering or clamping aspect may obviate the need for a ridge on the fusion cage. See FIG. 7C. In accordance with aspects of the present invention, one having ordinary skill in the art will appreciate that a shim that is configured to lie in more than one plane may be configured with members that operably engage more than one side a fusion cage, and thereby substantially block fluid communication between the hollow interior and the exterior of more than one side of the fusion cage. A shim that is configured to lie in more than one plane and reversibly self-adhere or clamp to a fusion cage may also be configured to be selectively released from the fusion cage by, for example, a mechanical force (e.g., a stress or strain force), magnetic force or electrical means. In accordance with other aspects of the present disclosure, the selective release or removal of the shim from the fusion cage will restore fluid communication between the hollow interior and the exterior of the fusion cage.

Figure 6:
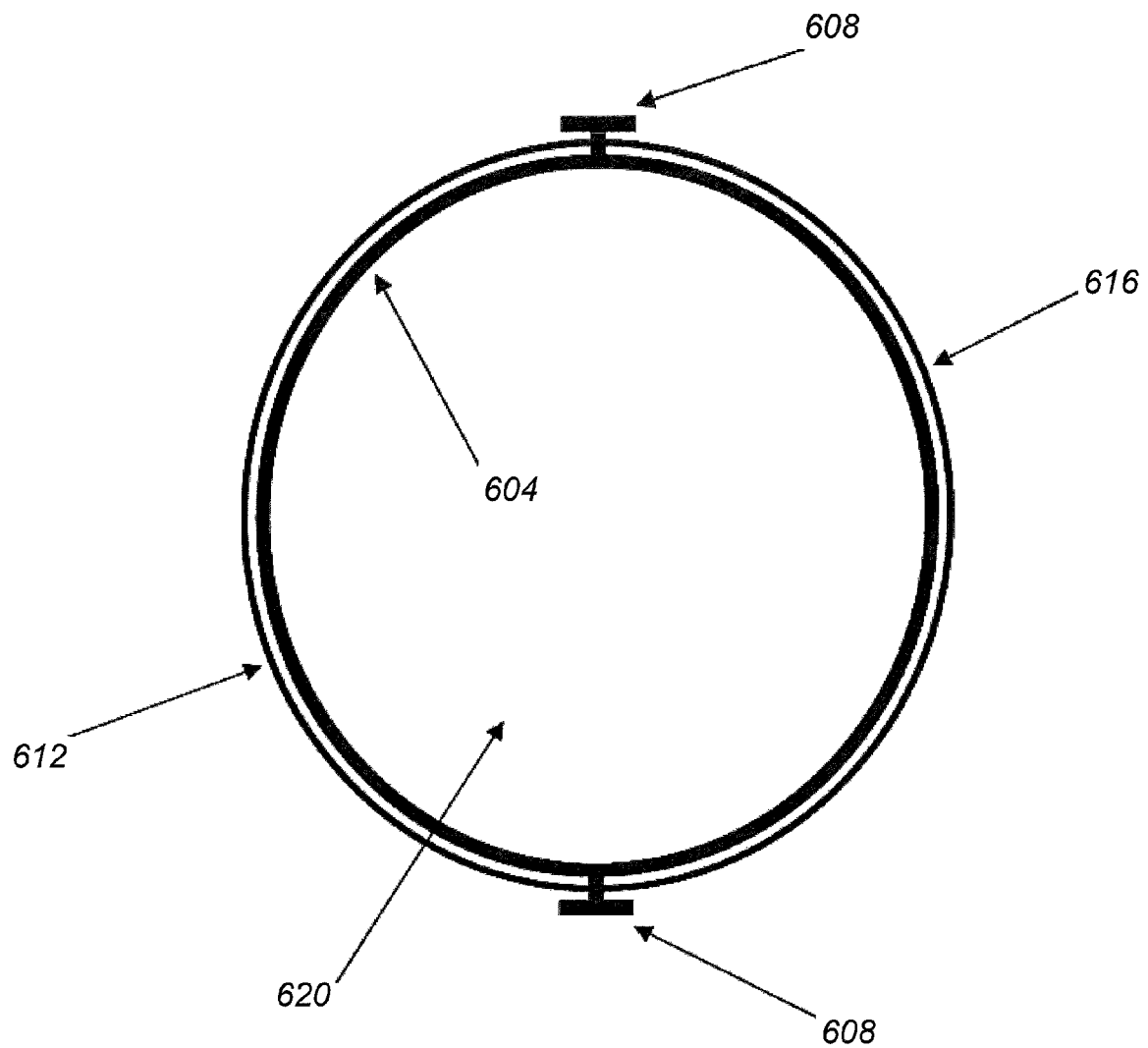
FIG. 6 shows an end view of a tubular or cylindrical cage with two removable shims in contact with an external surface of the cage and held in place by two guiding structures according to at least some embodiments of the present disclosure.

In certain embodiments, more than one side or portion of a cage is contacted by one or more shims. For example, without intending to be limiting, FIG. 6 shows an embodiment of a cage (e.g., round) where two shims are employed to cover desired surfaces of the cage, thus preventing liquid from escaping the cage. As otherwise described herein, the shims employed may be of any suitable geometry or combination. For example, a single circular shim could be used; one or more shims could be used in combination to achieve the desired preclusion of leakage of fluid from within a cage structure. Both insertion as well as removal of more than one shim, substantially simultaneously, may be achieved, thus reducing the number of operations required to provide a loaded cage structure. The end portions of one or more shims could be configured to render easy manipulations of the one or more shims by a tool.

Figure 8A:
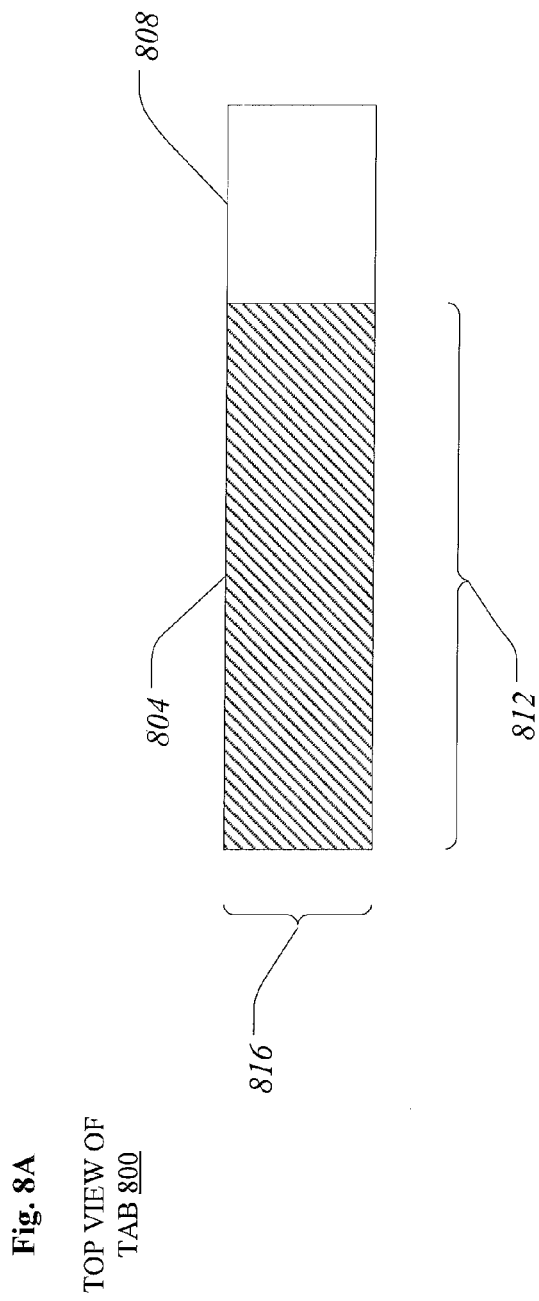
FIGS. 8A and 8B show two views of an embodiment of a shim according to at least some embodiments of the present disclosure.
Figure 8B:
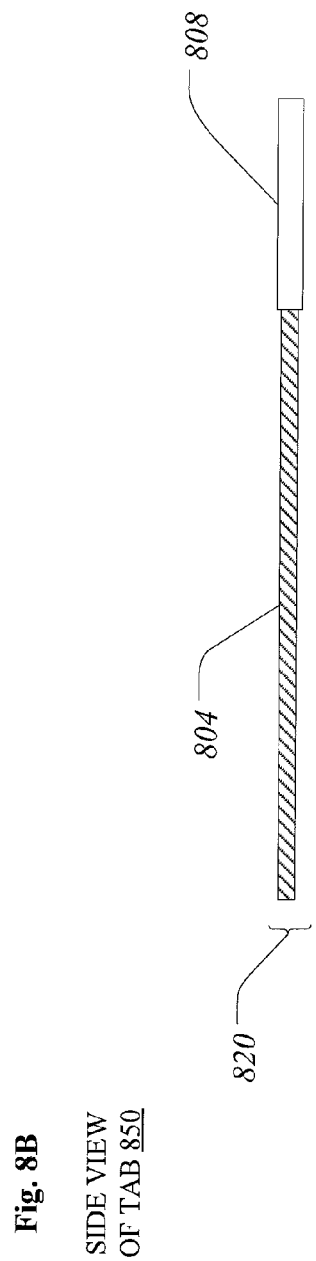

With specific reference now to FIGS. 5A, 8A and 8B, the shim 404, 804 preferably includes a projection or tab 508, 808 located at one end that projects beyond the outer perimeter of the cage and which serves to facilitate removal of the shim 404, 804. This projection or tab may vary in size to accommodate numerous surgical processes and its width may vary from relatively thin to the width 816 of the shim itself and its length may vary from relatively short to quite long. For example, and without wishing to be limited to any one embodiment, a user may grasp the projection or tab at the desired time of removal and pull it in order to remove the shim 804 from being in contact with the guiding structure(s). Alternatively, the projection or tab 808 may be configured to attach to a surgical tool such that the surgical tool may be used as the means of removing the shim. Optionally, the shim may also include an opening or hole through which a line or thread may be tied, or a surgical instrument may be inserted, in order to facilitate removal of the shim 804 from the cage. With specific reference now to FIGS. 8A and 8B, a shim is shown with a tab in one embodiment of the present disclosure. FIG. 8A shows a top aspect view of the shim 804 with the associated tab 808. One having skill in the art will appreciate that the tab may be of a material and dimensions (thickness, width, and length) different than that of the shim. The shim is shown to have a width 816 and a length 812. FIG. 8B shows a side aspect view of the shim 804 with the associated tab 808. The shim is shown to have a thickness 820. In one embodiment of the present disclosure, the thickness 820 of the shim is preferably between 0.4 mm and 0.75 mm inclusive. In some embodiments, this opening or hole is present in the projection or tab 808.

The guiding structure of the present disclosure may be present along the external surface in any number of manners. For example, in some embodiments the guiding structure is cast or machined with the cage as an extension of the external surface of the cage itself, thereby making the guiding structure a physical, continuous extension of the cage body. In other embodiments, the guiding structure is ground out of the exterior surface of the cage wall. In these embodiments, the guiding structure may be ground out at the time the cage is ground out of a portion of a larger material, or the guiding structure may be ground out in advance of implantation in order to provide a customized guiding structure. In still other embodiments, the guiding structure may be a separate piece that is attached to, or secured onto, the external surface of the cage prior to implantation. The guiding structure of these embodiments may be secured onto the external surface any one or more of many standard means by which two structures may be operably connected together, such as with the use of adhesives, welding, bands, straps, threading, a clamp, a snap-fit assembly, a bolted or screwed connection, a push-on/turn-on self-locking fastener, a press fit, rivets, and/or other, similar means. In other embodiments of the present disclosure, the ridge may be present on the internal surface of the cage.

In accordance with at least some aspects of at least one embodiment of the present disclosure, a surgically implantable intervertebral fusion cage is provided, the cage having a hollow frame that is substantially tubular, cylindrical or conical in shape. For purposes of illustration, and without wishing to be held to any one embodiment, the following U.S. Patents and U.S. Patent Publications are incorporated herein by this reference in order to provide an illustrative and enabling disclosure and general description of an intervertebral fusion cage that is substantially tubular, cylindrical or conical in shape: U.S. Pat. No. 5,653,763 to Errico et al.; U.S. Pat. No. 5,665,122 to Kambin; U.S. Pat. No. 5,888,228 to Knothe et al.; U.S. Pat. No. 6,648,915 to Sazy; U.S. Patent Application Publication No. 2004/0143330 to Sazy; U.S. Patent Application Publication No. 2005/0149192 to Zucherman et al.; and U.S. Patent Application Publication No. 2005/0149193 to Zucherman et al. Each of the foregoing known cages have the same basic tubular, cylindrical or conical construction and, for the sake of simplicity, will be referred to herein as having a main wall that is tubular, cylindrical, or conical in shape and/or configuration, a first end wall and a second end wall, each end wall being interconnected with the main wall so as to form a closed tube, cylinder, or cone in that the main wall is connected to the first end wall and to the second end wall in such a way that the main wall, first end wall and second end wall, when fully interconnected, define a hollow interior to the cage that is tubular, cylindrical or conical in shape and/or configuration. In some embodiments, the intervertebral fusion cage of the present embodiment has a diameter ranging from about 8 mm to about 18 mm and a length ranging from about 18 mm to about 55 mm. Thus, both the first and wall and the second end wall preferably have a diameter that ranges from about 8 mm to about 18 mm and the main wall has a length that ranges from about 18 mm to about 40 mm. When fully constructed, the tubular, cylindrical or conical shaped cages have an elongated appearance such that they are longer than they are tall, making the largest points of contact of the cage with the target vertebrae two arcs along the external surface of the main wall, one at the top of the surgical site that makes contact with one of the target vertebrae and one at the bottom of the surgical site that makes contact with a second target vertebra. The first end wall and the second end wall may also make contact with the target vertebrae, though it is preferable that the major points of contact with the target vertebrae will occur via the exterior surface of the main wall.

The main wall has at least one opening or fenestration, and preferably a plurality of openings or fenestrations, located along its length that provide a location, or locations, where material that is placed or stored inside of the hollow interior may freely move from the hollow interior to the exterior of the cage. The at least one opening or fenestration thus allows for fluid communication between the hollow interior 620 of the cage and the outside of the cage in a similar manner as described above. See, e.g., FIG. 6.

Additionally, the exterior surface of the main wall has at least one guiding structure located on it, which is configured to hold a shield or shim in place along the exterior surface of the main wall. In some embodiments, a single, T-shaped guiding structure runs the entire length of the exterior surface such that a single shield or shim can be wrapped around the full exterior circumference of the main wall and be held in place by making contact with both sides of the T-shaped guiding structure. As stated above, all embodiments of the guiding structure may be used to secure one or more shims to the external surface of a cage of these embodiments, though the embodiment of the guiding structure that is particularly useful for a cage of this shape and/or configuration is preferably the T-shaped guiding structure shown and described above. In other embodiments and with specific reference now to FIG. 6, the external surface has at least one guiding structure, and may also have a plurality of guiding structures, located on it and there may be two guiding structures 608 running the length of two opposing sides of the external surface such that two shims, a first shim 612 and a second shim 616, are held in place along two opposing sides of the external surface 604. In one embodiment, there are a plurality of guiding structures holding the shim in place, at least one running the length of the external surface as previously described and at least one located in a belt-like fashion around the entire perimeter of the external surface such that the shim slides under the at least one belt-like guiding structure, makes contact with the other at least one guiding structure, and is held in place accordingly. One having ordinary skill in the art will appreciate that in one embodiment where the fusion cage has only a single guiding structure running the length or part of the external surface, an arcuate shim may be configured whereby at least one edge of the shim makes contact with the guiding structure. In yet another embodiment and as described above, the fusion cage may not have any guiding structure on its external surface, and a shim may be configured to engage the fusion cage in a complementary fashion.

As mentioned above, the main wall has at least one, and preferably a plurality of, openings or fenestrations through it that allow for the movement of material out of the hollow interior and toward the target vertebrae. Therefore, when a shim is held in place by a guiding structure along the exterior surface of the main wall, the shim at least partially blocks or covers, and preferably completely blocks or covers, the at least one opening or fenestration located along and through the main wall. When the at least one opening or fenestration, and preferably the plurality of openings or fenestrations, are covered or blocked in this manner, the shim serves to prevent the movement of material as previously described. Additionally, when the shim is removed from contact with the guiding structure(s) located along the external surface of the main wall, fluid communication is restored as previously described.

The surgically implantable intervertebral fusion cages of the present disclosure, inclusive of the guiding structures of the present disclosure, may be made of any kind of material suitable for surgical implantation that is also sufficiently rigid so as to provide the required support between the target vertebrae, such as steel or medical grade plastic. In some embodiments, the guiding structure is an integral part of the cage and the two structures are cast or machined as a single, continuous unit. The cages and the guiding structures may be made of: surgical stainless steel of the general alloy type of iron, carbon, chromium (12-20%), molybdenum (0.2-3%), and nickel (8-12%); martensitic steel; 316L or 316LVM austenitic steel; and/or 316 surgical steel. It is desirable for the cages and guiding structures of the present disclosure to be quite rigid and strong in construction so as to prevent any deforming during use and/or after surgical implantation, which can cause a loss of function.

Referring now to FIGS. 7A and 7B, several of the embodiments of the fusion cage of the present disclosure include a securing site 712 that is configured to be contacted with at least a portion of an impactor or holder, a width 720, a length 724, a least one opening or fenestration 708, and at least one ridge 704. In these embodiments, the securing site 712 is configured so that the impactor or holder secures the fusion cage to a distal end portion of the impactor or holder and keeps the fusion cage so secured until such time as the user desires to remove the impactor or holder from the securing site 712 of the fusion cage. Therefore, the securing site 712 is configured so that the fusion cage can be releasably secured to the distal end portion of the impactor or holder. In some embodiments, the securing site 712 is a cavity or indentation located in an exterior portion of a single wall of the fusion cage that does not proceed through the entirety of the wall and thus does not provide a location where material may move from the interior of the fusion cage to the exterior of the cage. The securing site 712 may be located in any wall of the fusion cage of the present disclosure, though it is preferable for the securing site to be located in a lateral wall or an end wall of the fusion cage so as not to interfere with the openings or fenestrations 708 of the cage and to facilitate surgical implantation of the cage. It is also preferable for the securing site to be configured to be complimentary in size and shape to the distal tip 1618, 1818 of an internal member of the impactor or holder, to facilitate securing of the fusion cage to the distal end 1616, 1816 portion of the impactor or holder. The securing site 712 may be of any shape and configuration that is typically used to securely hold two objects together. By way of example, and without wishing to be limited to any one embodiment, the shape and configuration of the securing site may be any one or more of many standard shapes and configurations typically used to operably connect two structures together, such as threading, a clamp, a snap-fit assembly, a bolted or screwed connection, a push-on/turn-on self-locking fastener, a press fit and/or other, similar shapes and configurations. In some embodiments, the securing site 712 is threaded. The use of the securing site 712, in conjunction with the distal tip 1618 of the internal member of the impactor or holder, is described below. Referring specifically now to FIG. 7C, a side view of a cage is shown without a ridge 704. As described above, this fusion cage may be suitable for use with a shim that is self-adhering or attaching to the fusion cage.

Figure 10A:
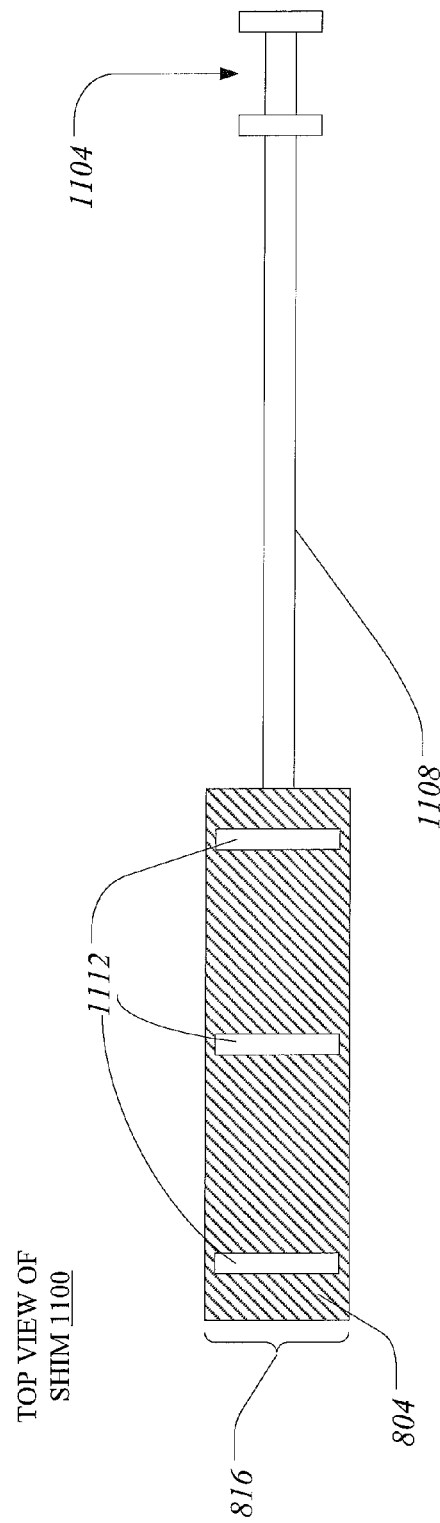
FIGS. 10A and 10B show two views of an embodiment of embodiment of a shim according to at least some embodiments of the present disclosure.

The shims of the present disclosure may be made of any kind of material suitable for surgical implantation that is rigid enough to completely prevent the movement of viscous materials from the hollow interior when the shim is in place along the exterior surface, but that is also sufficiently flexible so as to be readily removable and replaceable without being damaged or undergoing substantial plastic deformation. Suitable materials include, for example, plastic, poly(tetrafluoroethene) or poly(tetrafluoroethylene), or plastastic, though the shims may also be made of polyamide, polyethylene, polypropylene, polyphenylene sulfide, polyurethane, poly(tetrafluoroethylene), polyvinyl chloride, or polyvinylidene fluoride. In some embodiments, the shim includes at least one portion that is radiopaque, or that prevents the penetration of x-rays or similar forms of radiation. In some embodiments, the shim includes at least one portion that is a radio transmitter. In a more preferable embodiment, each shim has a plurality of radio transmitters 1112 that may be used in concert by a radio receiving device to determine the orientation and position of the shim, and therefore the fusion cage to which the shim is attached. See, FIG. 10A. In some embodiments each shim has a plurality of radiopaque portions 1112. See, FIG. 10A. These embodiments may be useful in conjunction with x-rays in order to determine whether the fusion cage of the present disclosure, having at least one such shim in place along an external surface, is being or has been properly oriented and/or inserted into the surgical site. The radiopaque portion may be an integral part of the shim itself, or may be an additional component that is put into contact with a portion of the shim. Any suitable radiopaque material may be used for the shims of these embodiments, including, without limitation, radiopaque thermoplastic compounds, such as LATI-GRAY by LATI Industria Termoplastici S.p.A., lead, ceramic, radiopaque polyolefin compounds, poly(methyl methacrylate), transition metals such as those present in Groups IIIB through IIB of the Periodic Table of the Elements, salts of such transition metals, nontransition metals such as those found in Periods 3 through 7 of Groups IA and IIA of the Periodic Table of the Elements, and salts of such nontransition metals. In some embodiments, the shims may be made of an absorbable or resorbable biologic material or may be made of a permeable mesh. Furthermore, the shims may be belt-like and recessed beneath a PEEK isthmus. The shims may also be semi-metallic so that they are radio-opaque and may, in and of themselves, be made of a material that incorporates in the fusion as a bone or fusion stimulant.

The size and shape of the projection or tab may vary between embodiments of the shim and the scope of the present disclosure is intended to include a projection or tab of any shape and/or size. In some embodiments, the projection or tab extends a short distance beyond the external face of the fusion cage when the shim is in place and is generally of a rectangular, square or polygonal shape. See, e.g., FIGS. 4 and 5A. In these embodiments, the projection or tab may be used to remove the shim from contact with the at least one guiding structure, and therefore from contact with the external surface of the fusion cage, by grasping the projection or tab and pulling the shim away from the fusion cage. Alternatively, the projection or tab of these embodiments may include a hole through it so that a surgical instrument may be inserted into the hole and used to remove the shim, or so that surgical thread or similar material may be placed through the hole, properly secured and then used to remove the shim.

Figure 10B:
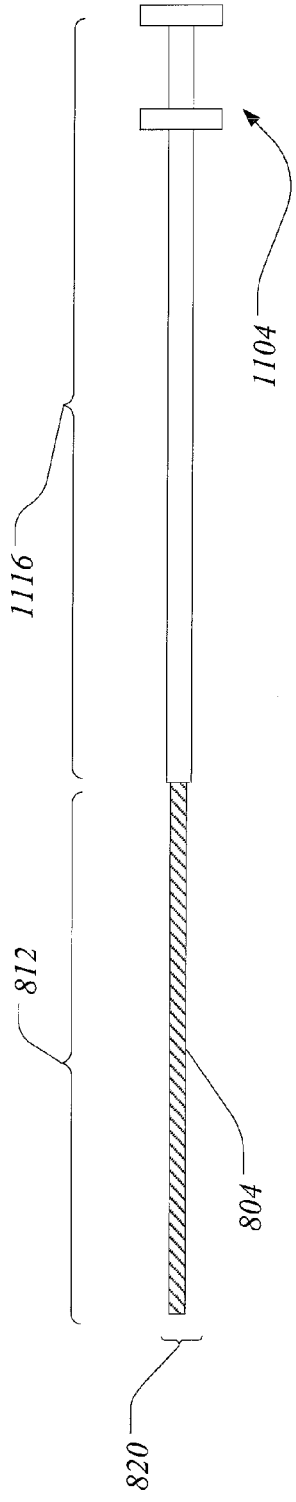

In other embodiments, the projection or tab is long and thin, extending beyond the external face of the fusion cage a greater distance when the shim is in place, and is generally of a rectangular or rounded shape. See, e.g., FIGS. 10A and 10B. In these embodiments, the projection or tab 1108 may be of sufficient length 1116 to remain outside of the patient after proper insertion of the fusion cage into the patient, thereby allowing the user to grasp the projection or tab 1108 after insertion of the fusion cage and pull on it, removing the shim 804 from the cage. Alternatively, the projection or tab 1108 of these embodiments may also include features, such as guiding structures 1104 or crests, at the distal end of the projection or tab that are used to secure the distal end of the projection or tab to a clamp or similar structure located along the handle of a surgical instrument such as an impactor or holder. See, e.g., FIG. 10A. By securing the distal end of the projection or tab to a surgical instrument, the user may pull on and remove the shim 804 from the external surface of the fusion cage by merely removing the surgical instrument from the surgical site. The shim 804 will be removed simultaneously with the surgical instrument. The projection or tab 1108 of these embodiments is preferably approximately 4 cm to approximately 10 cm in length 1116, more preferably approximately 6 cm to approximately 9 cm in length, and is even more preferably approximately 8 cm in length. See, e.g., FIG. 10B.

Figures 11A, 11B:
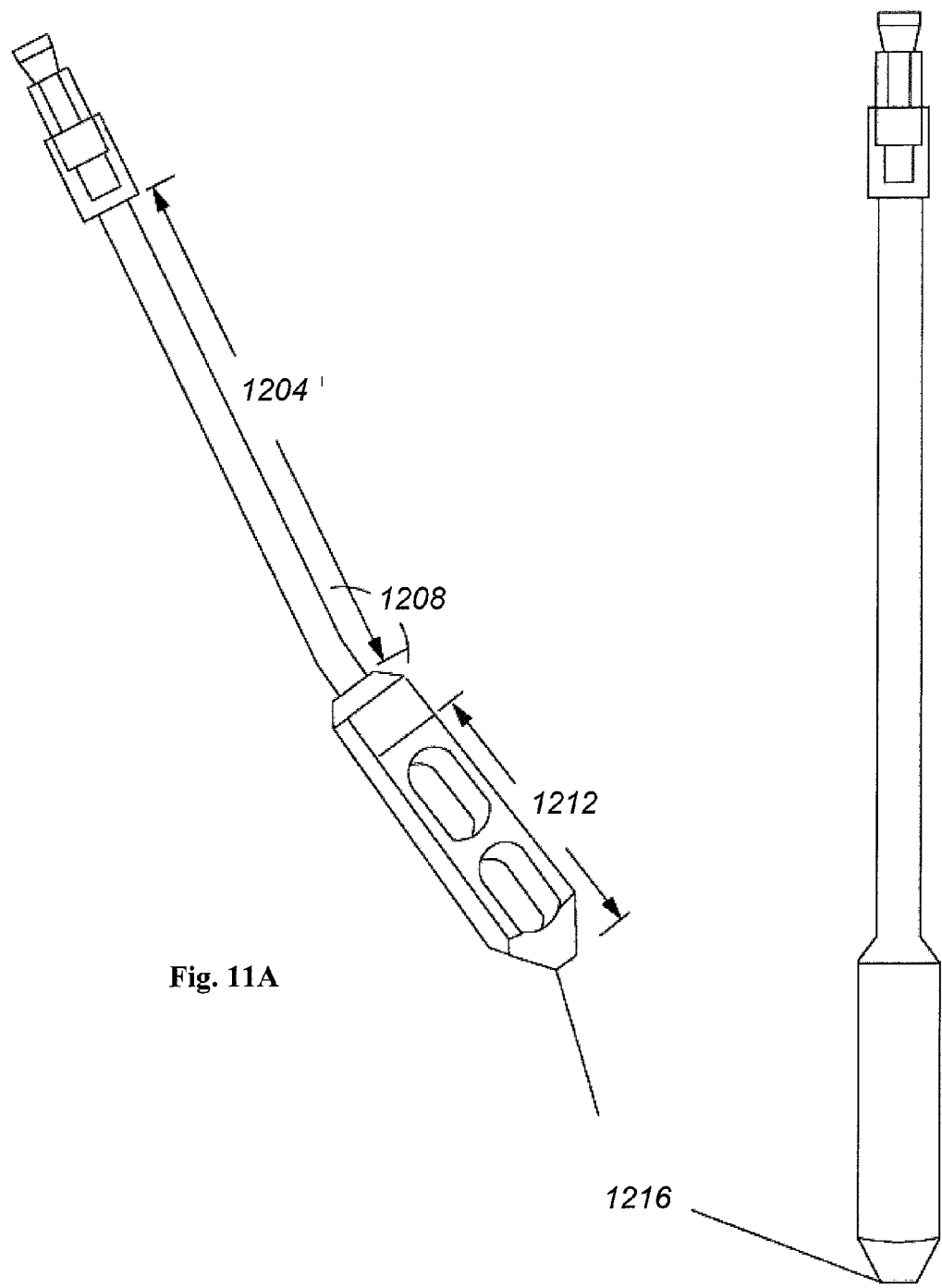
FIGS. 11A and 11B show two views of a distraction wedge according to at least some embodiments of the present disclosure.
Figure 12B:
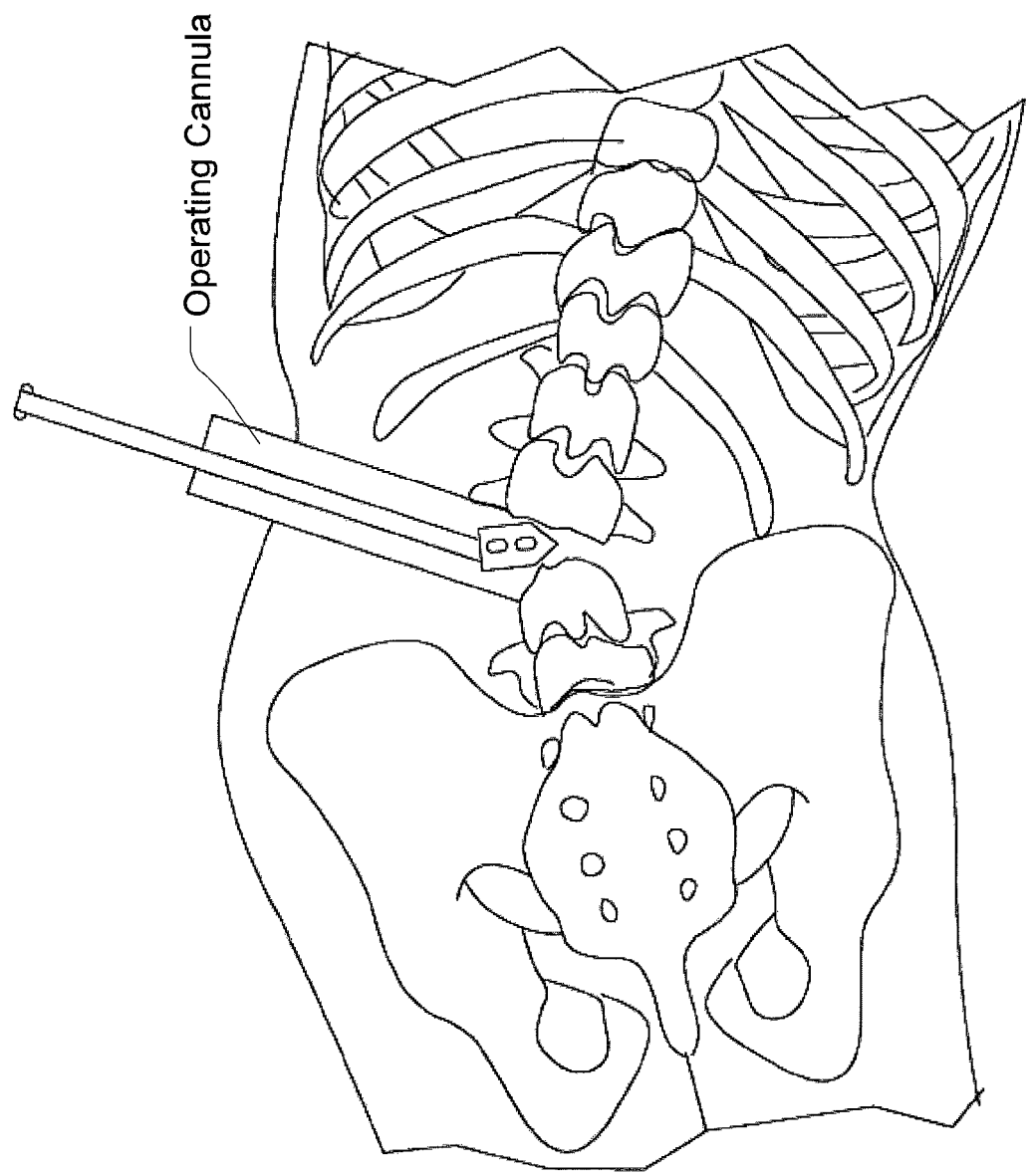
FIG. 12B is a side view of a laterally positioned patient who is maximally bent laterally according to at least some embodiments of the present disclosure, in the depicted scene, a distraction wedge according to at least some embodiments of the present disclosure is shown in place between vertebrae as shown.

In accordance with at least some aspects of at least one embodiment of the present disclosure, a distraction wedge is provided, the distraction wedge having an elongated handle that is substantially cylindrical in shape and a head at a proximal end of the distraction wedge that is configured to generate an opening in tissue that is of the size and shape of the head portion of the distraction wedge, the head portion being offset from the handle portion by an angle such that the head and the handle are not located in the same plane. See, e.g., FIG. 11A. Referring specifically to FIGS. 11A and 12, the distraction spacer is configured at an angle 1208, 1404 so that it may enter the disk space when the operating cannula is not at a right angle to the disk space. For purposes of illustration, and without wishing to be held to any one embodiment, the following U.S. Patents are incorporated herein by this reference in order to provide an illustrative and enabling disclosure and general description of a distraction wedge without a head portion being offset from the handle portion by an angle: U.S. Pat. No. 5,836,948 to Zucherman et al.; U.S. Pat. No. 5,860,977 to Zucherman et al.; U.S. Pat. No. 5,944,658 to Koros et al.; U.S. Pat. No. 6,238,397 to Zucherman et al.; U.S. Pat. No. 6,224,599 to Baynham et al.; U.S. Pat. No. 6,261,296 to Aebi et al.; and U.S. Design Pat. No. D374283 to Michelson. Each of the foregoing discloses a distractor or distraction wedge having a head portion that is in the same plane as the handle portion and, for the sake of simplicity, will be collectively referred to herein as having a head portion and a handle portion. None of the cited references teaches or discloses the head portion being offset from the handle portion by an angle.

The handle of the distraction wedge is generally cylindrical in shape and has a length ranging from about 140 cm to about 170 cm, and preferably from about 160 cm to about 165 cm, and has a diameter ranging from about 4 mm to about 5 mm. The distal end of the handle may optionally include features for attachment to other surgical instruments, though this is not necessary for purposes of the present invention. The proximal, or head, end of the distraction wedge comprises a head portion having a length ranging from about 15 mm to about 50 mm, a width ranging from about 40 mm to about 55 mm, and a height or thickness ranging from about 6 mm to about 16 mm. Thus, in some embodiments, the head portion is generally rectangular in shape. The head portion includes a proximal tip located at the proximal terminus of the head portion. In some embodiments, the proximal tip is pointed such that the height or thickness of the head portion and/or the width of the head portion is gradually reduced from the head portion to the proximal tip, culminating in a pointed edge. See, e.g., FIGS. 11A and 11B. The pointed edge is the initial portion of the distraction wedge to make contact with the target tissue, and thus facilitates dissection of the target tissue by displacing the tissue as it is moved forward into the tissue. The pointed tip thus makes it easier for the user to move the distraction wedge into the target tissue. The head portion of the distraction wedge is offset from the handle portion by an angle ranging from approximately 5 to 45 degrees, and preferably from about 15 to 25 degrees. See, e.g., FIGS. 11A and 11B.

In some embodiments and referring now to FIG. 11A, the head portion of the distraction wedge includes at least one recess or window located on a width face of the head. The at least one recess or window is present only on a single side of the distraction wedge and does not pass through the entire head portion of the distraction wedge. The at least one recess or window may be of any size or shape and the present disclosure is intended to include recesses and/or windows of any size and shape that are capable of fitting on the head portion of the distraction wedge. In some embodiments, the at least one recess or window is generally square or rectangular in shape. The at least one recess or window may be used in conjunction with x-rays or similar forms of radiation to view the distraction wedge during use to determine whether it has been properly positioned in the surgical site.

The distraction wedges of the present disclosure may be made of any kind of material suitable for surgical use, such as aluminum, iron, titanium, steel, medical grade plastic, surgical stainless steel of the general alloy type of iron, carbon, chromium (12-20%), molybdenum (0.2-3%), and nickel (8-12%); martensitic steel; 316L or 316LVM austenitic steel; and/or 316 surgical steel.

In accordance with at least some aspects of at least one embodiment of the present disclosure and referring now to FIG. 13A, an impactor or holder is provided, the impactor or holder having an elongated, hollow handle 1610 that is substantially cylindrical in shape, a distal end portion having an annular projection or lip 1622, at least one clamp 1612 located on the external surface of the handle portion at a distance from the distal end portion, and an internal member 1608 located inside of the hollow handle 1610 that comprises a distal end 1616, a shaft 1614, and a proximal end 1604, and that is configured to rotate about its longitudinal axis upon prompting by the user, the distal end 1616 portion being offset from the handle portion by an angle 1620 such that the distal end 1616 and the handle 1604 are not coaxial.

For purposes of illustration, and without wishing to be held to any one embodiment, the following U.S. Patents are incorporated herein by this reference in order to provide an illustrative and enabling disclosure and general description of a hollow impactor or holder without a head portion being offset from the handle portion by an angle: U.S. Pat. No. 6,004,326 to Castro et al.; and U.S. Pat. No. 7,004,946 to Parker et al. Both of the foregoing discloses an impactor or holder having a head portion that is in the same plane as the handle portion and, for the sake of simplicity, will be collectively referred to herein as having a head portion and a handle portion. Neither reference teaches or discloses the head portion being offset from the handle portion by an angle.

Referring once again to FIG. 13A, the hollow handle 1610 of the impactor or holder is generally cylindrical in shape and has a length ranging from about 140 cm to about 170 cm, and preferably from about 160 cm to about 165 cm, an outer diameter ranging from about 5 mm to about 6 mm, and an inner diameter ranging from about 2 mm to about 3 mm. The distal end 1616 portion has an annular projection or lip 1622 that is also offset from the handle portion by an angle 1620. Referring now to FIG. 13B, the annular projection or lip 1622 serves as a point of contact for a fusion cage 1624, such that when a fusion cage 1624 is being held in place by the impactor or holder, it contacts the annular projection or lip 1622. FIG. 13B illustrates the impactor or holder assembled to the fusion cage 1624. In some embodiments, when a fusion cage 1624 is held in place by the impactor or holder, the fusion cage is tightly contacted with the entire distal face of the annular projection or lip 1622. In these embodiments, the annular projection or lip 1622 prevents the fusion cage 1624 from moving during placement into the patient. One having ordinary skill will appreciate that in an alternate embodiment, instead of a fusion cage 1624, a pointed distraction tool as illustrated in FIGS. 11A and 11B may be assembled to the distal end 1616 of the impactor or holder. One having ordinary skill in the art will also appreciate that the annular lip 1622 may have features on the side that engages with the fusion cage 1624 to have a stabilizing effect to stabilize the fusion cage 1624 and prevent unwanted rotation or movement of the fusion cage 1624 during its assembly to the distal end 1616 and during its release from the distal end 1616. Such a feature may include, for example, a tab, a pin, a ridge, a dowel or an indexing pin. It will be appreciated that the fusion cage 1624 will have a corresponding, and complementary feature that engages or is engaged by the feature on the annular lip 1622 including, for example, an aperture, an indexing notch, a registration tab or notch, a slot or a groove.

In some embodiments, the impactor or holder includes an internal member 1608 that is configured to rotate about its longitudinal axis when prompted by the user of the impactor or holder. In these embodiments, the internal member is also configured to releasably secure embodiments of the spinal fusion cage to a distal end 1616 portion of the impactor or holder and to keep the fusion cage 1624 secured to the distal end portion during surgical implantation of the spinal fusion cage 1624, and to release the fusion cage 1624 once it is in place at the desired surgical site when prompted by the user. The internal member 1608 may be a wire, rod or cable that is sized to fit within the inner diameter of the hollow handle 1610 of the impactor or holder and to rotate freely therein, without interference from the inner walls of the impactor or holder. The internal member 1608 may have, at its proximal end 1604, a means by which the user may releasably secure the spinal fusion cage to the distal end 1616 of the impactor or holder. In some embodiments, this means is a thumbwheel or thumbscrew 1606 that is secured to the distal end 1616 of the internal member such that, when the thumb screw 1606 is rotated by the user, the internal member 1608 rotates about its longitudinal axis. In these embodiments, it is preferable for the thumb screw 1606 to be configured so that it may rotate in both directions. As shown in the figure, it is yet another aspect of the present disclosure that a shield 1602 may be configured to encompass the thumb screw 1604 while at the same time providing operational access to the thumb screw 1604. The shield 1602 may be a stiff band or projection that is attached to the handle 1610 and projects above the thumb screw 1606. The shield 1602 provides a location whereby the user of the impactor or holder may apply a force such as by thumping, percussing or striking the shield 1602 of the impactor or holder using, for example, a hammer or other firm device. One having ordinary skill in the art will appreciate that the force imparted to the shield 1602 is transmitted to the handle 1610, and in turn transmitted through the projection or lip 1622 to the a device secured on the distal end 1616 of the impactor or holder tool. Also in these embodiments, the distal tip 1618 of the internal member is configured to be complimentary in size and shape to the securing site 712 of the spinal fusion cage, to facilitate securing of the fusion cage to the distal end 1616 portion of the impactor or holder. The distal tip of the internal member is thus configured so that, when the thumb screw is rotated in a first direction, the distal tip 1618 of the internal member is tightened into the securing site 712, thus securing the fusion cage in contact with the annular lip 1622 of the impactor or holder. Similarly, the distal tip 1618 of the internal member is thus configured so that, when the thumb screw 1606 is rotated in a second direction, the distal tip 1618 of the internal member is released from the securing site, thus releasing the fusion cage from contact with the annular lip of the impactor or holder. In these embodiments, it is preferable for the distal tip 1618 of the internal member to be threaded so that when the internal member 1608 is rotated in the first direction by the means for rotating, the distal tip 1618 is moved into the securing site (which is preferably threaded in a complimentary manner) and so that when the internal member 1608 is rotated in the second direction, the distal tip 1618 is moved out of the securing site. Preferably, when the distal tip is moved into the securing site, the threading serves to secure the fusion cage to the annular lip 1622 of the impactor or holder. It is therefore useful for the user to move the distal tip 1618 of the internal member 1608 into the securing site by an amount that will be sufficient to engage enough threading to hold the fusion cage to the impactor or holder via the securing site.

In alternate embodiments, the internal member may be configured as a spring that is configured to move in a longitudinal direction within the length of the impactor or holder. In these embodiments, the means by which the user may releasably secure the spinal fusion cage to the distal end of the impactor or holder may be a plunger, configured to be pressed by the user. Similarly, the distal tip of the internal member may be configured so that it serves to hold the fusion cage to the annular lip of the impactor or holder via means that can be secured by a spring, or plunger, type motion. These means for securing may include, without limitation, a clamp, a snap-fit assembly, a push-on/turn-on self-locking fastener, and/or a press fit assembly.

In some embodiments, the impactor or holder includes at least one structure 1612 located along its outer diameter at some distance from the annular lip or projection that is configured to engage and secure a portion of a projection or tab of a shim. In these embodiments, the structure 1612 can be configured such that it secures a terminal end of an extended projection or tab 508, 808 of a shim, which has been secured against an external face of a fusion cage, and holds that terminal end of the shim in place along the external length of at least a portion of the impactor or holder while the fusion cage is in contact with the annular lip of the impactor or holder. See, e.g., FIG. 13B. In some embodiments, a plurality of such structures is present on the impactor or holder. Preferably, the number of these structures will equal the number of shims in use with the fusion cage. In use, these structures can serve to remove the shim from the fusion cage simultaneously with the removal of the impactor or holder from the surgical site, as the terminal ends of the shim(s) will be secured in place at the structures so that, when the fusion cage has been delivered and the impactor or holder is removed from the surgical site, the terminal end of the shims will remain held in place along the external length of at least a portion of the impacter or holder. The motion of removing the fusion cage from the surgical site thus also serves to remove the shims from contact with the external surface of the fusion cage. In some embodiments, these structures are C-clamp like structures that are capable of securely holding the terminal end of a projection or tab during surgical implantation of the fusion cage. See, e.g., FIGS. 13A and 13B.

The impactor or holder of the present disclosure may be made of any kind of material suitable for surgical use, such as aluminum, iron, titanium, steel, medical grade plastic, surgical stainless steel of the general alloy type of iron, carbon, chromium (12-20%), molybdenum (0.2-3%), and nickel (8-12%); martensitic steel; 316L or 316LVM austenitic steel; and/or 316 surgical steel. The internal member of the impactor or holder of the present disclosure may be a wire, rod or cable, each of which may be made of any kind of material suitable for surgical use, such as aluminum, iron, titanium, steel, medical grade plastic, surgical stainless steel of the general alloy type of iron, carbon, chromium (12-20%), molybdenum (0.2-3%), and nickel (8-12%); martensitic steel; 316L or 316LVM austenitic steel; and/or 316 surgical steel. The structure(s) configured to engage and secure a portion of a projection or tab of a shim may be made of the same materials as listed above, and may also be made of medical grade plastic.

In accordance with at least some aspects of at least one embodiment of the present disclosure, a method of surgically implanting an intervertebral fusion cage into a patient is provided. The method comprises obtaining a surgically implantable intervertebral fusion cage having at least one wall, at least one guiding structure located on an exterior surface of the at least one wall, and at least one removable shield or shim. The at least one wall defines a hollow interior to the cage and has at least one opening or fenestration in it that allows for fluid communication between the hollow interior and an exterior of the cage. The guiding structure is operable to hold the at least one shim in contact with the exterior surface and is configured to allow the at least one shim to be freely removed from, and replaced onto, the exterior surface of the wall.

The method further includes preparing the cage for surgical implantation by filling the hollow interior with a material capable of fusing two bony structures, preferably two vertebrae, and more preferably two adjacent vertebrae, together and contacting the at least one shim with the exterior surface of the cage by positioning the shim under at least a portion of the at least one guiding structure such that the at least one shim is contacted with and held in place along the exterior surface by the at least one guiding structure by way of such contact. In some embodiments, when the at least one shim is contacted with the at least one guiding structure, the shim at least partially covers or blocks the at least one opening or fenestration, preventing fluid communication between the hollow interior and the exterior of the cage, and preventing the material from leaving the hollow interior.

After the cage has been prepared for implantation, the method includes locating an appropriate surgical site in a patient for implantation of the cage. The surgical site may be an intervertebral location, including the space typically filled by an intervertebral disc, but may also be any location in a patient where two bony structures are to be fused together. A surgical opening is created in the patient that will accommodate the cage. This opening may be made dorsally, ventrally, laterally or at any other location along the patient that is medically efficacious to grant the user access to the surgical site. The cage is then surgically implanted into the patient and positioned in the surgical site between the desired bony structures, and preferably between the two adjacent vertebrae of interest, in such a way that will serve to utilize the material in connection with the patient's own systems to promote the fusion of the two bony structures by way of, and through, the cage. Thereafter, the at least one shim is removed from contact with the guiding structure and the exterior surface of the cage, thereby restoring fluid communication between the hollow interior and the exterior of the cage and allowing the material to move from the hollow interior to the exterior of the cage. Once these tasks are completed, the method is concluded by closing the surgical opening in the patient.

In accordance with still other aspects of the present disclosure, a further method of surgically implanting an intervertebral fusion cage into a desired location within a patient is provided. In at least one embodiment of these aspects of the present disclosure, the method includes obtaining a cage having: (i) at least one wall defining a hollow interior of the cage, the wall having at least one opening or fenestration in it that allows for fluid communication between the hollow interior and the exterior of the cage; (ii) at least one constraining structure, such as a guiding structure, on an exterior surface of the wall that is configured to reversibly hold at least one shim in place along the exterior surface of the wall, wherein the at least one guiding structure is configured to allow the at least one shim to be removed from, and replaced onto, the exterior surface of the wall; (iii) at least one removable shim; and (iv) means for receiving a securing element capable of securing the cage to a distal end portion of an impactor or holder. The method further includes preparing the cage for surgical implantation by filling the hollow interior with a material that is capable of fusing two vertebrae, or other bony structures, together and placing the at least one shim in contact with the exterior surface of the cage such that the at least one shim is secured or held in place along the exterior surface by the at least one guiding structure and wherein the at least one shim substantially blocks the at least one opening or fenestration, thereby substantially preventing fluid communication between the hollow interior and the exterior of the cage and thereby retaining at least most of the material inside of the hollow interior. The method further includes locating an appropriate site inside of the patient for implantation of the cage, positioning the patient (e.g., laterally, posteriorly or anteriorly) so as to obtain the desired amount of exposure of the desired surgical site, and creating a surgical opening in the patient that exposes the desired surgical site and that is sufficient to accommodate the cage. The surgical site may be an intervertebral location, including the space typically filled by an intervertebral disc, but may also be any location in a patient where two bony structures are to be fused together.

Once the opening is created, the method further includes generating a sufficient amount of distraction, or an opening of desired size and shape, at the surgical site by inserting a distraction wedge into the patient, contacting the distraction wedge with the tissue to be opened, and moving the distraction wedge into the tissue to be opened until the desired shape and depth of distraction, or opening, is created in the tissue to be opened. Thereafter, the method further includes surgically implanting the cage into the patient in such a way that the fusion of the two vertebrae or other bony structures will occur upon exposure to the material, by securing the cage to a distal end portion of an impactor or holder, moving the cage and impactor or holder into the surgical opening, contacting the cage with the site of surgical implantation, and moving the cage into the surgical site. Thereafter, the cage is selectively released from the distal end portion of the impactor or holder and the impactor is removed from the surgical opening. The method is concluded by closing the opening in the patient.

In some embodiments of this method, during the preparation of the fusion cage for implantation, the projection or tab of the at least one shim is placed in contact with a structure located along the outer diameter of the impactor or holder and secured along the outer diameter by the structure. In these embodiments, the method further includes removing the at least one shim from contact with the guiding structure, and thus the exterior surface of the wall, simultaneously with the removal of the impactor or holder from the surgical opening, thereby restoring fluid communication between the hollow interior and the exterior of the cage and allowing the material to move from the hollow interior to the exterior of the cage. In other embodiments of this method, the at least one shim is removed after the impactor is removed from the surgical opening via a pulling force exerted on the projection or tab of the at least one shim.

In some embodiments, the step of positioning the patient includes laterally positioning the patient, or placing the patient on his or her side, so that the portion of the intervertebral space into which a fusion cage is to be implanted is closer in proximity to the health care provider than if the patient were to be placed on his or her other side. In these embodiments, the step of positioning further includes maximally bending the patient laterally so that the side that is closer in proximity to the health care provider is maximally arched, with the patient's other side being minimally arched, rendering the surgical site of interest in as open a configuration as possible. In further embodiments, the patient is maximally bent laterally so as to maximize the distance between the patient's lower-most rib and the patient's iliac crest.

Figures 14A, 14B:
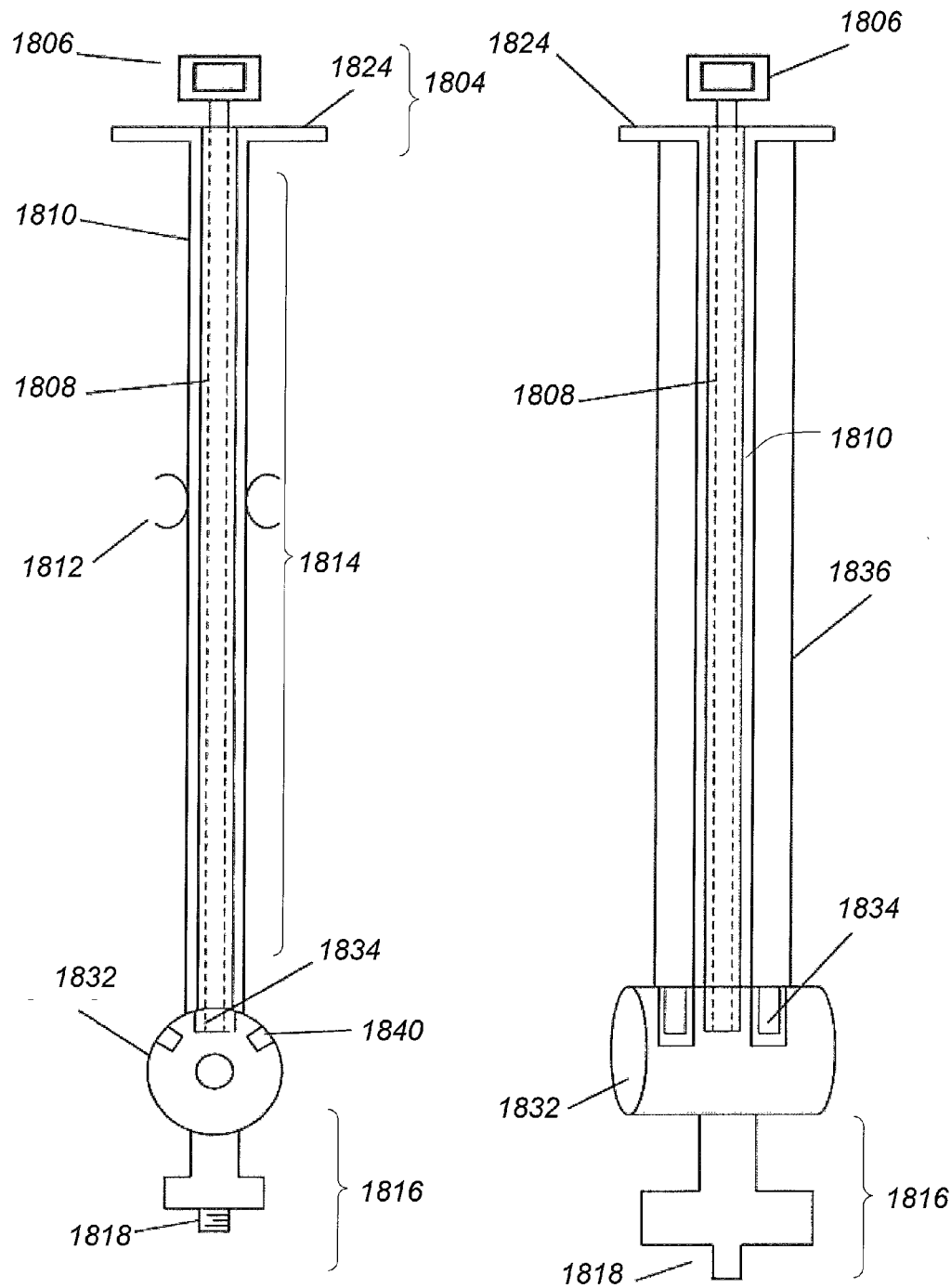
FIGS. 14A and 14B show two views of an impactor or holder having an exterior shaft and a distally-located rotating hinge according to at least some embodiments of the present disclosure.

In some embodiments of the present disclosure and referring specifically now to FIGS. 14A and 14B, a distraction wedge and/or an impactor or holder having a handle 1810 and a distally-located rotating hinge 1832 is provided, wherein the handle 1804 has an input means 1806 for communicating with the distal end of the body. The input means 1806 may comprise, for example, a trackball, a rotating member, a lever, an electronically controlled signal, a button, or another structural feature that provides desired movement at the opposite end of the tool. In one embodiment, the input means 1806 is a thumbscrew that is in communication with the shaft 1808, which may be a rotating member including, for example, a cable, a shaft or other rotating means. The shaft 1808 is in communication with the distal tip 1818, providing thereby, communication between the input means 1806 and the distal tip 1818. The rotating hinge 1832 is configured to allow the head portion of the distraction wedge and/or the distal end 1816 portion of the impactor or holder to rotate in at least one plane about an axis and thereby be offset from the handle 1810 of the distraction wedge and/or an impactor or holder, and from the external shaft 1836, by an angle, and wherein the exterior shaft 1810 is configured to change the angle of the rotating hinge 1832 and to lock the rotating hinge 1832 in place at a desired angle. The rotating hinge 1832 is also configured to provide communication between the input means 1806 and the distal tip 1818. One having skill in the art will appreciate the devices or methods that may be used to provide the aforementioned communication. These methods may include, for example, a cable, a universal joint, a constant velocity joint.

One having ordinary skill in the art will appreciate that in certain embodiments, the rotating hinge 1832 may be one or more of an electronically, hydraulically or pneumatically actuated device, whereby one or more of the angle of rotation, the movement and the locking of the rotating hinge may be controlled electronically, hydraulically or pneumatically. If the rotating hinge 1832 is controlled by electronic means, the control may be performed by a remote user through an electronic signal or radio signal. One having ordinary skill in the art will further appreciate that in certain embodiments, the input means 1806 may be in communication with the distal tip 1818 by remote or indirect means including an electronic signal, a radio signal. As such, the input means 1806 may accept a mechanical input (e.g., a twisting motion) or an electronic signal to correspondingly engage or cause an effect on the distal tip 1818.

In these embodiments, the distraction wedge and/or the impactor or holder are as previously described and have the added features of the external shaft 1836 and the rotating hinge 1832. In some embodiments, the external shaft 1836 is a tube located along and around the exterior surface of the handle 1810 of the distraction wedge and/or impactor or holder (see, e.g., FIGS. 14A and 14B). The external shaft 1836 is substantially cylindrical in shape, hollow and, in some embodiments, has a distal end portion configured to operatively engage at least a portion of the rotating hinge 1836 in such a way so as to lock the rotating hinge 1832 in place at a desired angle. The external shaft 1836 may optionally include a means for grasping 1824 the external shaft 1836 located on its proximal terminus, wherein the means for grasping 1824 is configured so that the user can readily grasp the exterior shaft 1836 and move it either forward or backward along the longitudinal axis of the handle. In some embodiments, the means for grasping is an annular lip 1824 (see, e.g., FIGS. 14A and 14B). The external shaft has a length ranging from about 100 cm to about 170 cm, an outer diameter ranging from about 4 mm to about 8 mm, and an inner diameter ranging from about 2 mm to about 7 mm. The external shaft 1836 of the present disclosure may be made of any kind of material suitable for surgical use, such as aluminum, iron, titanium, steel, medical grade plastic, surgical stainless steel of the general alloy type of iron, carbon, chromium (12-20%), molybdenum (0.2-3%), and nickel (8-12%); martensitic steel; 316L or 316LVM austenitic steel; and/or 316 surgical steel.

The rotating hinge 1832 is integrated into the handle portion 1810 of the distraction wedge and/or the impactor or holder, thus providing a point of separation between the handle portion 1810 and the head portion of the distraction wedge and/or the distal end 1816 portion of the impactor or holder. In some embodiments, the rotating hinge 1832 operates in a manner substantially identical to a door hinge, wherein the rotating hinge allows the head portion of the distraction wedge and/or the distal end 1816 portion of the impactor or holder to rotate freely in at least one plane and/or at least one direction, in a back-and-forth manner. In other embodiments, the rotating hinge 1832 operates in a manner substantially identical to a wave platform shaker, wherein the head portion of the distraction wedge and/or the distal end portion 1816 of the impactor or holder are attached to the rotating hinge 1832 at a single point and wherein the rotating hinge is configured to allow the head portion and/or the distal end 1816 portion to rotate freely in three dimensions.

The rotating hinge 1832 allows the head portion of the distraction wedge and/or the distal end 1816 portion of the impactor or holder to be offset from the handle 1810 and from the exterior shaft 1836 by an angle so that they may be utilized as described herein without the need for the handle of the distraction wedge and/or an impactor or holder or for the exterior shaft to be aligned with the surgical site at a right angle. In some embodiments, the angle of the head portion of the distraction wedge and/or the distal end 1816 portion of the impactor or holder is determined by securing or locking means located at the distal terminus of the external shaft, which are configured to lock the rotating hinge in place, and thereby set a desired angle of use for the head portion of the distraction wedge and/or the distal end 1816 portion of the impactor or holder (see, e.g., FIGS. 14A and 14B).

In some embodiments, the locking means comprises at least one locking pin 1834, which may be an extension of the external shaft 1836 itself or which may be a separate component secured to the distal terminus of the exterior shaft (see, e.g., FIGS. 14A & 14B). In the embodiment depicted in FIGS. 14A & 14B, the locking means is a pair of locking pins 1834, located on opposing sides of the exterior shaft 1836. In other embodiments, the locking means can include, for example, a single locking pin 1834, a series of interlocking teeth, threading, a clamp, a snap-fit assembly, a bolted or screwed connection, a push-on/turn-on self-locking fastener, a press fit, or other, similar means of locking two objects together. One having ordinary skill in the art will appreciate the different methods and device that may be used to lock the rotating hinge 1832. In operation, the distal terminus of the exterior shaft 1832 is configured so that, when the exterior shaft 1832 is moved along the longitudinal axis of the handle 1810, the locking means (e.g., a locking pin 1834) becomes engaged, or disengaged, with the rotating hinge 1832. When the locking means is engaged with the rotating hinge 1832, the head portion of the distraction wedge and/or the distal end 1816 portion of the impactor or holder is secured in place and prevented from motion. Conversely, when the locking means is disengaged from the rotating hinge 1832, the head portion of the distraction wedge and/or the distal end 1816 portion of the impactor or holder is free to move to a desired angle. The exterior shaft 1810 is therefore configured so that it can repeatedly retract the locking means from the rotating hinge and reengage the locking means with the rotating hinge and can thus repeatedly secure the head portion of the distraction wedge and/or the distal end 1816 portion of the impactor or holder in place in any means desired including, without limitation, in plane with the external shaft or out of plane by any desired angle. The rotating hinge 1832 is used to change the angle of the head portion of the distraction wedge and/or the distal end 1816 portion of the impactor or holder relative to the angle of the handle. The rotating hinge 1832 also has at least one receiving means that are capable of receiving the locking means and thus securing the head portion of the distraction wedge and/or the distal end 1816 portion of the impactor or holder in place at a desired angle. The receiving means may be a hole or recess that is capable of accommodating the locking means or may be of any configuration that will serve to lock the head portion of the distraction wedge and/or the distal end 1816 portion of the impactor or holder in place by the locking means described above.

In some embodiments, the rotating hinge 1832 is configured to rotate at least backward and forward in at least one plane along an axis that is substantially perpendicular to the longitudinal axis of the handle of the distraction wedge and/or the impactor or holder and that is substantially perpendicular to the longitudinal axis of the exterior shaft 1836. When the locking means is disengaged from the receiving means, the rotating hinge 1832 swings freely such that it may rotate freely around this axis in at least one plane. Conversely, when the locking means is engaged with the receiving means, the head portion of the distraction wedge and/or the distal end 1816 portion of the impactor or holder will be secured in place and no longer mobile such that the rotating hinge will be locked at a desired angle relative to the longitudinal axis of the handle. The rotating hinge 1832 is configured so that it can freely rotate through all angles that are unimpeded by the handle and may be secured or locked in place at any angle within this range. In some embodiments, the rotating hinge may have at least one, and preferably a series, of preset angles; the presetting may be accomplished by setting the receiving means at one or more desired locations 1840 along the axis of the rotating hinge 1832 so that the locking means will only engage the rotating hinge 1832 at a desired angle. By way of example, and without wishing to be limited to any one embodiment, the rotating hinge may have present angles corresponding to −90 degrees, −60 degrees, −45 degrees, −30 degrees, 0 degrees, +30 degrees, +45 degrees, +60 degrees or +90 degrees in a single plane of motion. However, the rotating hinge is capable of being locked by the locking and receiving means at any desired angle, such as −90 degrees, −89 degrees, −88 degrees, −87 degrees, −86 degrees . . . and so on.

In some embodiments, the locking means may be engaged with the receiving means or disengaged from the receiving means during use. In these embodiments, the exterior shaft may be utilized as described herein to engage and/or disengage the locking means from the receiving means during use so that the angle of the head portion of the distraction wedge and/or the distal end portion of the impactor or holder relative to the longitudinal axis of the handle may be adjusted during a surgical procedure. In some embodiments, the exterior shaft includes at least one structure 1812 located along its outer diameter (e.g., the handle 1810 or external shaft 1836) at some distance from the distal terminus that is configured to engage and selectively secure a portion of the projection or tab 508, 808 of a shim 404, 804. In these embodiments, the structure can be configured such that it secures a terminal end of the extended projection or tab 508, 808 of the shim that has been secured against the external face of a fusion cage of the present disclosure and holds the terminal end of the shim in place along the external length of at least a portion of the outer diameter while the fusion cage is secured at the securing site. In some embodiments, a plurality of such projections or tabs 508, 808 is present on the outer diameter. Preferably, the number of these projections or tabs 508, 808 will equal the number of shims in use with the fusion cage. These structures can serve to remove the shim from the fusion cage simultaneously with the removal of the exterior shaft holder from the surgical site, as the terminal ends of the shim(s) will be secured in place at the structures 1812 so that, when the fusion cage has been delivered and the exterior shaft is removed from the surgical site, the terminal end of the shims will remain held in place by the structures 1812. The motion of removing the fusion cage from the surgical site thus also serves to remove the shims from contact with the external surface of the fusion cage. In some embodiments, these structures 1812 are C-clamp like structures that are capable of securely holding the terminal end of a projection or tab during surgical implantation of the fusion cage. In other embodiments, the shim is removed after the impactor or holder is removed from the surgical opening.

In yet another embodiment, the shim may be removed before the impactor or holder is removed from the surgical opening. This may be effected by the structures 1812 having, for example, retracting capability, a ratcheting mechanism, or a spring-loaded mechanism. Information relevant to the current state of the art as it applies to the foregoing devices or capabilities, including useful written, enabling descriptions of how to make and use various components, can be found in the following U.S. Patents and U.S. Patent Publications, the entire contents of which are incorporated herein by this reference: U.S. Pat. No. 7,478,577 to Wheeler, U.S. Pat. No. 7,455,157 to Kimes et al., U.S. Pat. No. 7,430,945 to Gauthier et al., U.S. Pat. No. 7,421,772 to Gao et al., U.S. Pat. No. 7,413,065 to Guathier, U.S. Pat. No. 7,410,478 to Yang, U.S. Pat. No. 7,410,334 to McGrew, U.S. Pat. No. 7,399,041 to Prentner et al., U.S. Pat. No. 7,357,284 to Jauvin, and U.S. Pat. No. 7,316,070 to Green.

Figure 15:
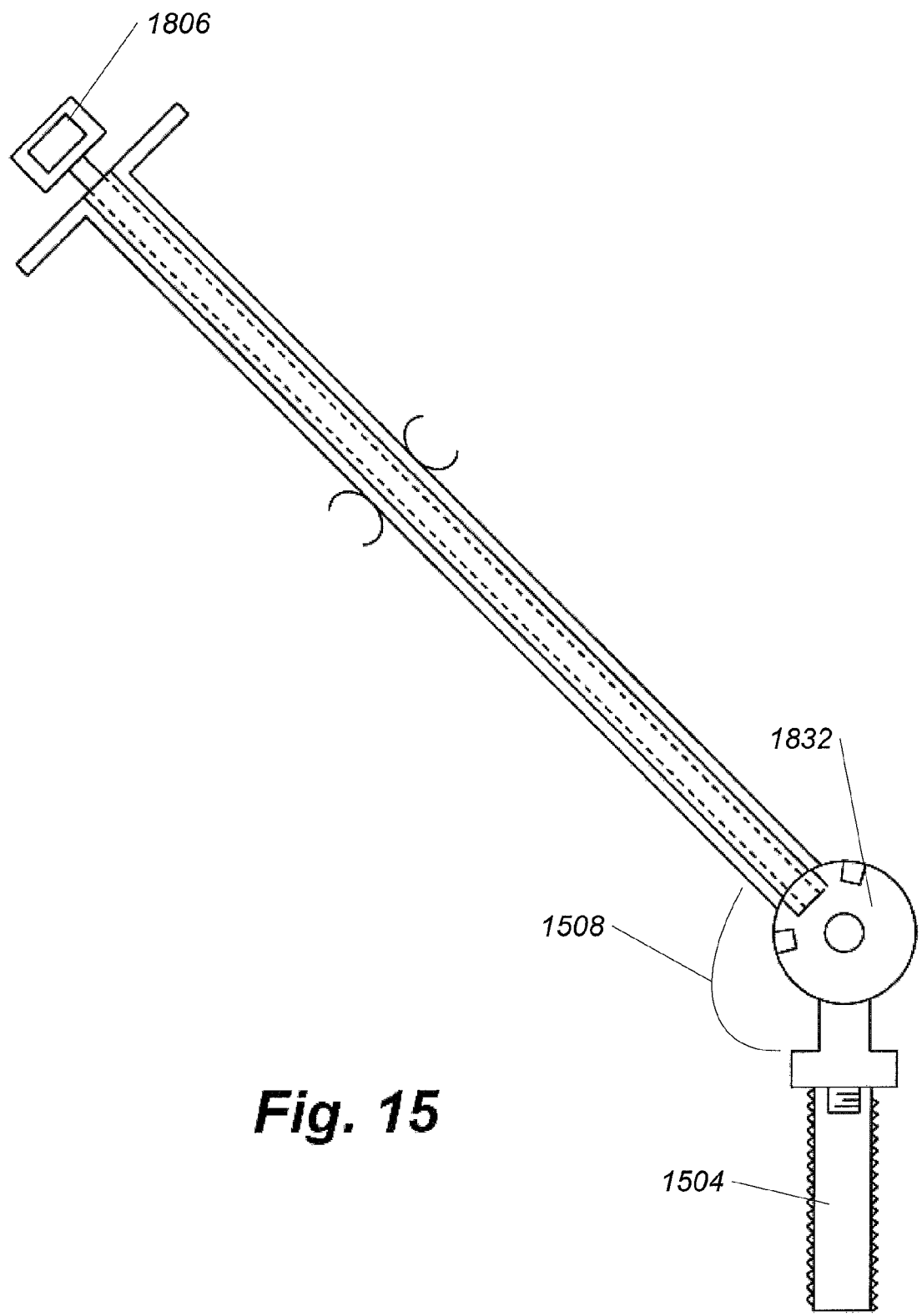
FIG. 15 shows a view of an impactor or holder having an exterior shaft and a distally located rotating hinge according to at least some embodiments of the present disclosure, and a fusion cage, graft or other device secured to the distal end of the impactor or holder.

Referring specifically now to FIG. 15, an impactor or holder is shown that exemplifies a preferred use of embodiments of the present disclosure. The impactor or holder of FIGS. 14A and 14B has a device 1504 secured at the distal end; the impactor or holder is angled at the hinge or rotating hinge 1832 or rotating member; and as described in the foregoing, the thumbscrew 1806 can communicate with the distal tip 1818 of the impactor or holder to selectively engage or disengage the device 1504. As illustrated and described in the foregoing, the annular lip 1824 may be used to engage the external shaft 1836 and thereby lock or unlock the rotating hinge 1832 to set the handle of the impactor or holder at an angle 1508 relative to the device 1504.

Figure 16A:
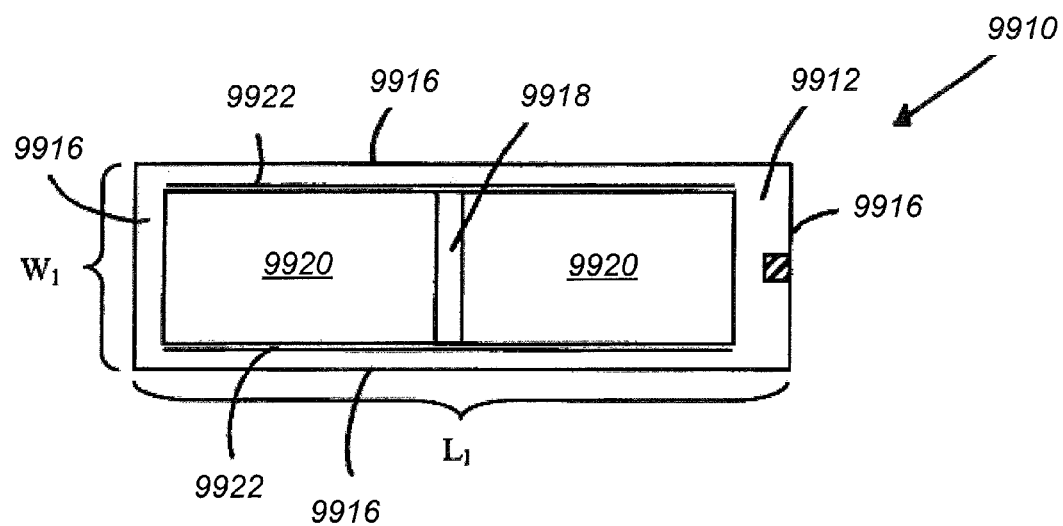
FIGS. 16A and 16B show two views of a cage according to at least some embodiments of the present disclosure.
Figure 16B:
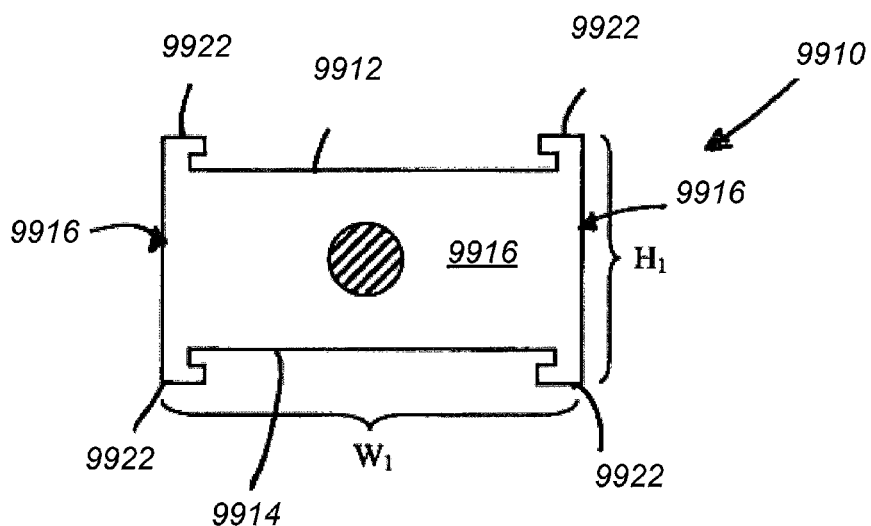

FIGS. 16A and 16B illustrate an example of an intervertebral fusion cage 9910 according to one broad aspect of the present invention. The fusion cage 9910 has a basic rectangular construction and, for the sake of simplicity, will be referred to herein as having a top wall 9912, a bottom wall 9914 and four lateral walls 9916, which collectively form the shape of a rectangle in that each lateral wall 9916 is connected to a single edge of the top wall 9912 at a top edge of the lateral wall 9916 and the bottom edge of the lateral wall 9916 is connected to a single edge of the bottom wall 9914 in such a way that the top wall 9912, bottom wall 9914 and four lateral walls 9916, when fully interconnected, create a shape that is substantially rectangular or square-shaped and also define a hollow interior to the cage. In some embodiments, additional walls 9918 may be present, for example within the interior chamber of the cage in order to create at least two separate hollow interior chambers within the cage and the ridges and veneers 9924 of the present disclosure will operate identically with these embodiments with no loss of function whatsoever.

The intervertebral fusion cage 9910 has a height H1 ranging from about 8 mm to about 18 mm, a width W1 ranging from about 10 mm to about 12 mm, and a length L1 ranging from about 18 mm to about 40 mm. Thus, both the top and bottom walls 9912, 9914 preferably have a length that ranges from about 18 mm to about 40 mm and a width ranging from about 10 mm to about 12 mm, and each of the lateral walls 9916 have a length that ranges from about 18 mm to about 40 mm and a height ranging from about 8 mm to about 18 mm. When fully constructed, the substantially rectangular or square shaped cages have a flat profile such that they are longer and wider than they are tall, making the largest points of contact of the cage with the target vertebrae the exterior surface of the top wall 9912 and the exterior surface of the bottom wall 9914. The lateral walls 9916 may also make contact with the target vertebrae, though it is preferable that the major points of contact with the target vertebrae will occur via the exterior surface of the top wall 9912 and the exterior surface of the bottom wall 9914.

Both the top wall 9912 and the bottom wall 9914 have at least one opening or fenestration 9920, and preferably a plurality of openings or fenestrations 9920, that provide a location, or locations, where fusion-promoting material that is placed or stored inside of the hollow interior may freely move from the hollow interior to the exterior of the cage 9910. The at least one opening or fenestration 9920, thus allows for fluid communication between the hollow interior of the cage 9910 and the outside of the cage 9910. The purpose of these openings or fenestrations 9920 is to provide a means by which a portion of a material (e.g. FPM or bone grafting material) that is placed inside of the hollow interior of the cage 9910 prior to implantation may escape from the hollow interior and make contact with the target vertebrae at the top of the cage 9912 and at the bottom of the cage 9914, while retaining a portion of the material inside of the hollow interior. In this way, the material makes contact with one of the target vertebrae at the exterior surface of the top wall 9912 of the cage and makes contact with another of the target vertebrae at the exterior surface of the bottom wall of the cage 9914, while at the same time there is sufficient material remaining inside of the hollow interior so as to promote the fusion of the target vertebrae by the generation of bony or osseous tissue through and around the fusion cage 9910.

Additionally, at least one of the exterior surface of the top wall or the exterior surface of the bottom wall has at least one ridge 9922 located on it, which is configured to hold a shield or veneer 9924 in place along the exterior surface of the particular wall. Preferably, the ridge is present on at least two of the edges of the exterior surface such that the shield or veneer 9924 is held in place by the ridge 9922 along at least two, and in some embodiments, three sides of the exterior surface of the wall in question. As shown in FIGS. 16A and 16B, for example, the external surface of the cage 9910 has a plurality of ridges 9922 located on thereon and there are two ridges 9922 along two opposing edges of the external surface of the top wall 9912 such that the veneer 9924 is held in place.

In some embodiments, as illustrated in FIGS. 16A and 16B, it is preferable for at least one ridge 9922 to be located along the exterior surfaces of both the top wall 9912 and the bottom wall 9914 so that a first veneer 9924 may be held in place by at least one ridge 9922 along the external surface of the top wall 9912 and a second veneer 9924 may be held in place by at least one ridge 9922 along the external surface of the bottom wall 9914. As mentioned above, the top and bottom walls 9912, 9914 have the at least one, and preferably a plurality of, openings or fenestrations 9920 through them that allow for the movement of material out of the hollow interior of the fusion cage 9910 and toward the target vertebrae. Therefore, when a first veneer 9924 is held in place by at least one ridge 9922 along the exterior surface of the top wall 9912 and a second veneer 9924 is held in place by at least one ridge 9922 along the exterior surface of the bottom wall 9914, the first veneer 9924 and the second veneer 9924 at least partially block or cover, and preferably completely block or cover, the at least one opening or fenestration 9920 located along and through the top and bottom walls 9912, 9914. When the at least one opening or fenestration 9920 is covered or blocked in this manner, the veneers 9924 serve to prevent the movement of material, such as FPM or bone grafting material, from the hollow interior to the exterior of the cage 9910. The veneers 9924 thus serve to prevent or block the fluid communication that would otherwise exist between the hollow interior and the exterior of the cage 9910. Therefore, when either the first and/or second veneer 9924 is removed from contact with the ridges 9922 located along the external surfaces of the top wall 9912 and the bottom wall 9914, fluid communication is restored between the hollow interior and the exterior of the cage 9910 and the material may move from the hollow interior through the at least one opening or fenestration 9920 to the outside of the cage 9910.

It is also preferable for the at least one ridge 9922 to be configured to hold or retain the veneer(s) 9924 in place along the external surface in question sufficiently tightly so as to prevent the movement of material from the hollow interior to the outside of the cage 9910. It is thus another aspect of the present disclosure for the at least one ridge 9922 to hold the veneer(s) 9924 in place along, and in direct contact with, the external surface of the top and/or bottom wall 9912, 9914 so that the veneer(s) 9924 lies flat, without any wrinkles or gaps, and such that the veneer(s) 9924 is held in contact with the external surface so as to prevent the movement of a substantial amount of a free flowing fluid, such as water, from the hollow interior to the outside of the cage 9910, and to completely prevent the movement of a more viscous material, such as a FPM or bone grafting material, from the hollow interior to the outside of the cage 9910. It is also an aspect of the present disclosure for the at least one ridge 9922 to be configured to allow the veneer(s) 9924 to be freely removable from the external surface of the top and/or bottom wall 9912, 9914 and replaceable onto the external surface of the top and/or bottom wall 9912, 9914 numerous times with no loss of function whatsoever. It is therefore preferable for the at least one ridge 9922 to be configured so as to allow the veneer(s) 9924 to move into and out of place along the external surface a plurality of times and to still hold the veneer(s) 9924 in place sufficiently snugly to at least substantially prevent the movement of a viscous material from the hollow interior to the outside of the cage 9910. By way of example only, the veneer(s) 9924 are configured to slideably engage the cage 9910 by way of the at least one ridge 9922.

Figure 17A:
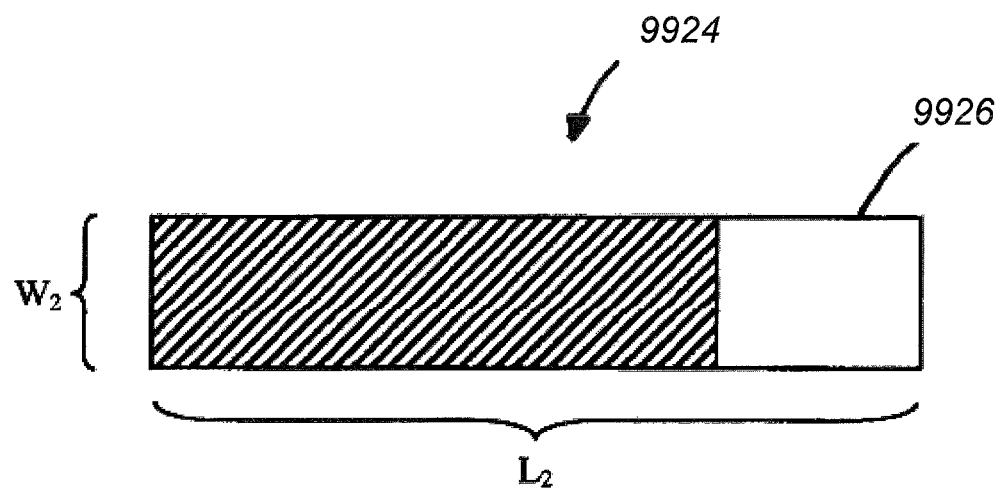
FIGS. 17A and 17B show two views of a veneer according to at least some embodiments of the present disclosure.
Figure 17B:
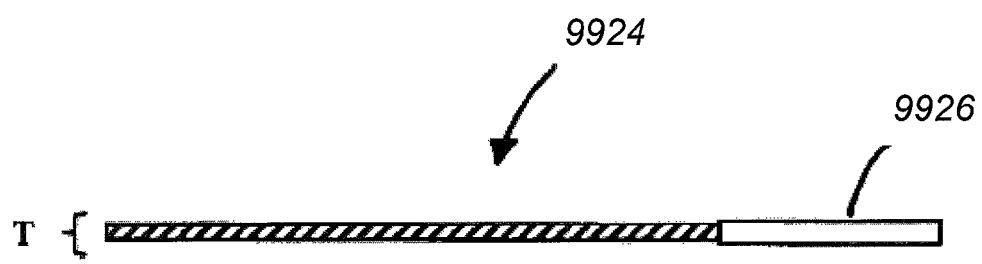

The veneer 9924 may be configured to be used with any number of cage configurations, shapes and sizes. For example, the veneer 9924 may be of a generally rectangular or square configuration and thus operable with the rectangular or square embodiments of the cage 9910 of the present disclosure described above. Additionally, the veneer 9924 may be shaped in a cylindrical, tubular, conical, circular, arced or rounded manner so as to be operable with the cylindrical or rounded embodiments of the cage 9940 of the present disclosure described below. For purposes of the present disclosure, the veneer 9924 may be of any shape and/or size desired including, without limitation, square, rectangular, triangular, round, circular, tubular, cylindrical, polygonal, conical, and any other shape that may be of use with an implantable intervertebral fusion cage 9910 of the present disclosure. With specific reference now to FIGS. 3 and 4, an example of a veneer 9924 is shown with a tab 9926 according to one embodiment of the present disclosure. The veneer 9924 preferably includes a projection or tab 9926 located at one end that projects beyond the outer perimeter of the cage 9910 and which serves to facilitate removal of the veneer 9924 after implantation of the cage 9910. For example, a user may grasp the projection or tab 9926 at the desired time of removal and pull it in order to remove the veneer 9924 from being in contact with the ridge(s) 9922. Optionally, the veneer 9924 may also include an opening or hole (not shown) through which a line or thread may be tied, or a surgical instrument may be inserted, in order to facilitate removal of the veneer 9924 from the cage 9910. FIG. 17A shows a top aspect view of the veneer 9924 with the associated tab 9926. A person having skill in the art will appreciate that the tab 9926 may be of a material and dimensions (thickness, width, and length) different than that of the veneer 9924. The veneer 9924 is shown to have a width W2 and a length L2. FIG. 17B shows a side aspect view of the veneer 9924 with the associated tab 9926. The veneer 9924 is shown to have a thickness T. In one embodiment of the present disclosure, the thickness T of the veneer 9924 is preferably between 0.4 mm and 0.75 mm inclusive.

Figure 18A:
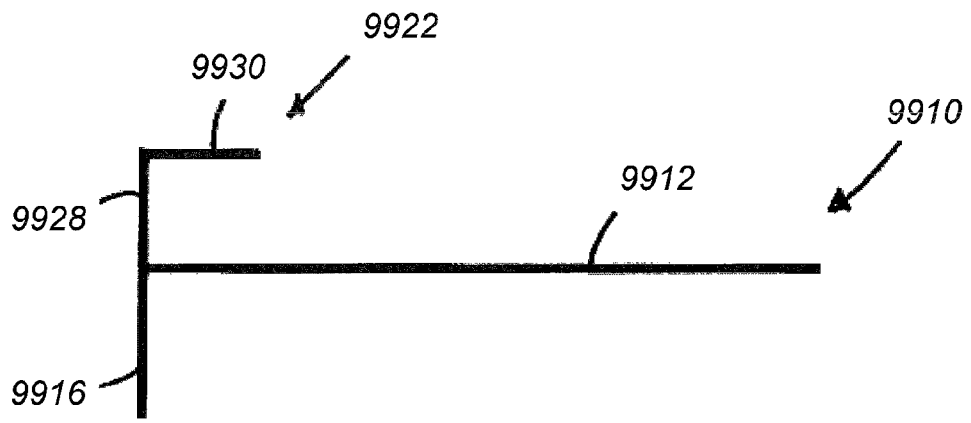
FIGS. 18A and 18B show two views of a portion of a cage and a portion of a veneer according to at least some embodiments of the present disclosure.
Figure 18B:
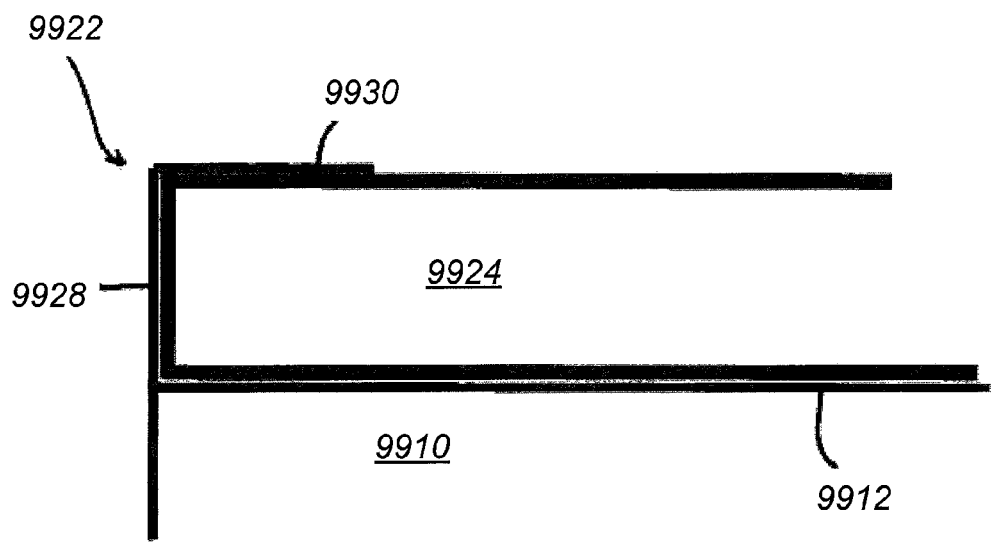

The at least one ridge 9922 may be configured in any number of manners that will allow the ridge 9922 to hold the veneer 9924 snugly to the external surface and to allow for the free removal and replacement of the veneer 9924 numerous times with no loss in function. In the embodiment described above and referring specifically to FIGS. 18A and 18B, the ridge 9922 is comprised of a projection of the following general L-shaped configuration:

In these embodiments, the bottom portion 9928 of the ridge 9922 projects generally perpendicularly from the top wall 9912 of the cage 9910, at or near the intersection between the top wall 9912 and side wall 9916. The upper (or overhang) portion 9930 of the ridge 9922 extends perpendicularly from the bottom portion 9928 and projects over the top wall 9912 of the fusion cage 9910 in such a way so that the veneer 9924 slides under the overhang 9930 of the ridge 9922 and is held in place by making contact with the overhang 9930. The overhang portion 9930 of this embodiment may vary in angle, though it is preferable that the overhang portion be at a 90 degree angle relative to the bottom portion 9928.

Figure 19A:
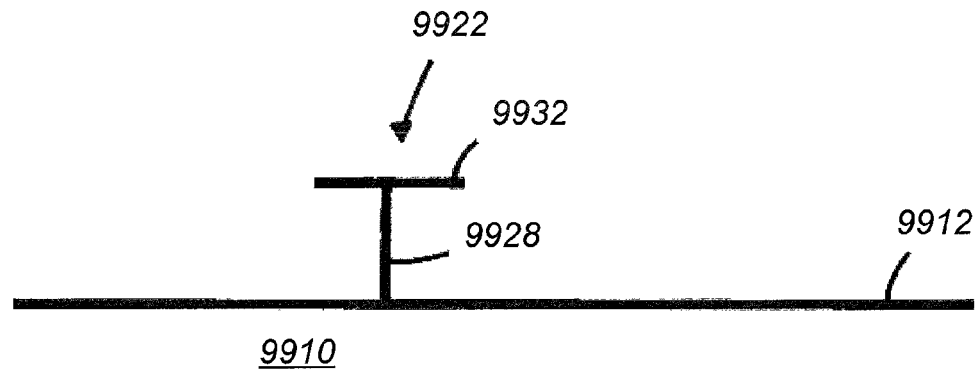
FIGS. 19A and 19B show two views of a ridge portion of a cage according to at least some embodiments of the present disclosure.

In still other embodiments and referring specifically to FIG. 19A, the ridge 9922 may be configured to secure a veneer 9924 on two sides. The ridge 9922 of these embodiments has the following general T-shaped configuration:

In these embodiments, the bottom portion 9928 of the ridge 9922 projects generally perpendicularly from the top wall 9912 of the cage 9910 and the upper portion (crossbar) 9932, projects generally perpendicularly and outward from the bottom portion 9928 in two directions, so that a veneer 9924 can slide under either side of the crossbar 9932 of the ridge 9922 and be held in place by the crossbar 9932. It is preferable for the crossbar portion 9932 of these embodiments to be at a 90 degree angle relative to the bottom portion 9928. This embodiment of the ridge 9922 is particularly useful with cages of a round or cylindrical configuration, as described below, though they may also be used in any of the embodiments of the present disclosure.

Figure 19B:
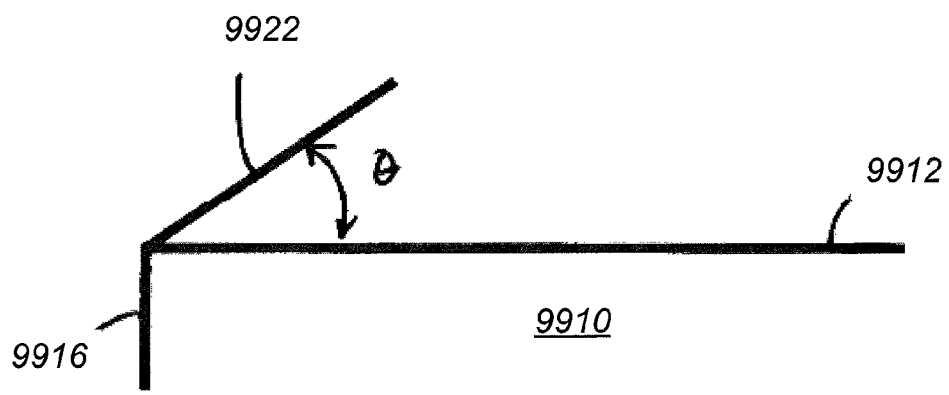

Referring to FIG. 19B, in some embodiments the ridge 9922 is a single projection that extends outward from the external surface of the top wall 9912 (forming an acute angle θ with the top wall 9912) such that the veneer 9924 slides under the ridge 9922 and is held in place until such time as the veneer 9924 is removed from under the ridge 9922. In these embodiments, the angle θ may be configured to fit a specific veneer 9924. By way of example only, the angle θ is an acute angle ranging from about zero degrees to about 45 degrees, or more preferably from about 15 degrees to about 35 degrees. In these embodiments, the veneer 9924 is held in place under the ridge 9922 strictly by the angle θ of the ridge 9922, which makes contact with the veneer 9924 along the underside of the ridge 9922 and holds the veneer 9924 snugly to the external surface of the top wall 9912.

Figure 20A:
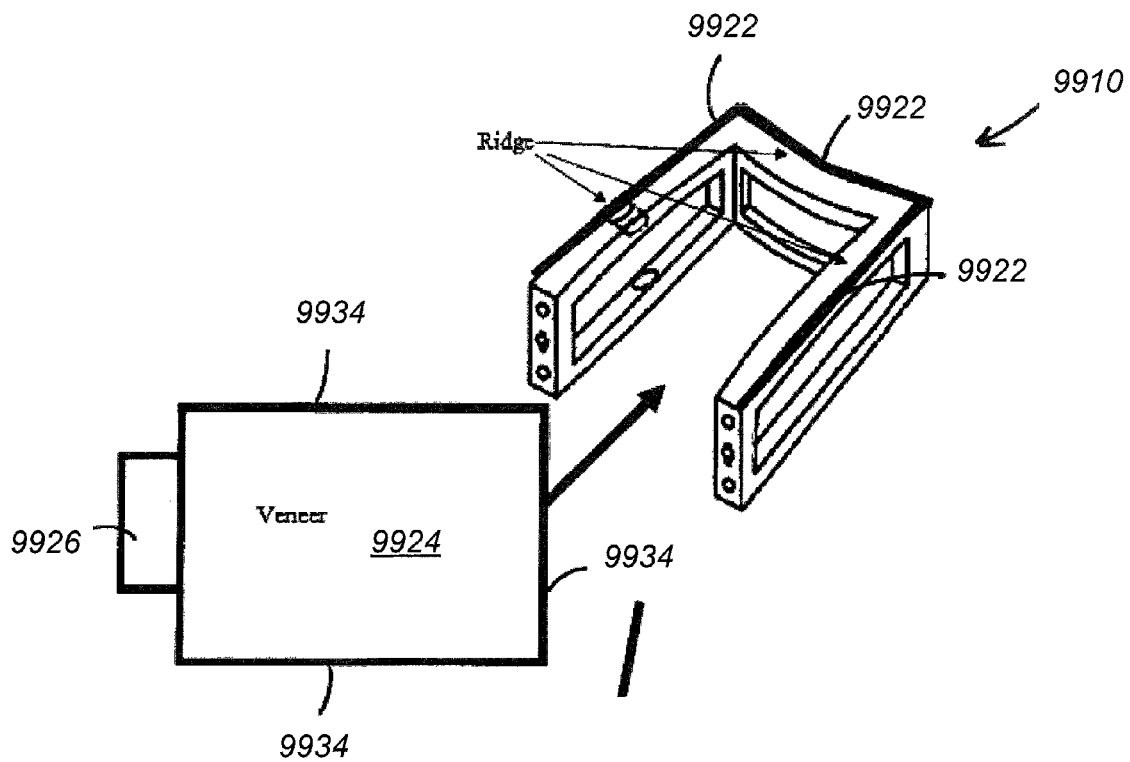
FIGS. 20A and 20B show two views of a cage according to at least some embodiments of the present disclosure.
Figure 20B:
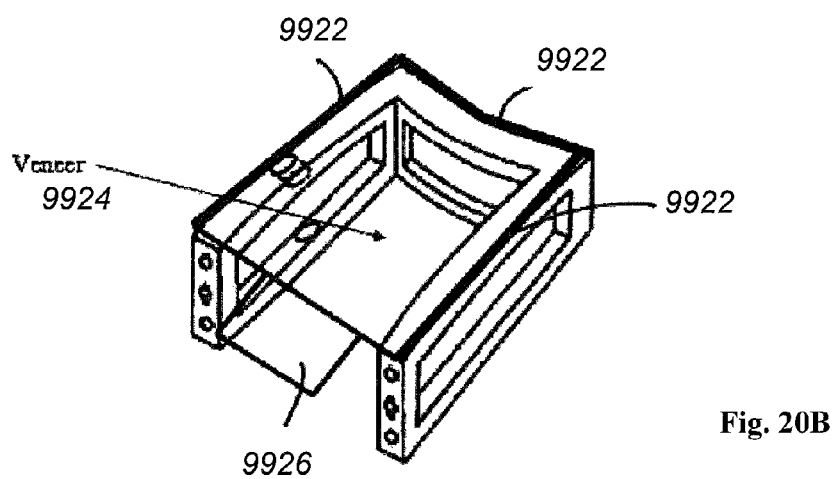

Although shown and described above as having a configuration in which a pair of ridges 9922 is provided on either or both of the top and bottom walls 9912, 9914 in order to secure the veneer 9924 in place, other configurations are possible. For example, FIGS. 20A and 20B illustrate an example of a fusion cage 9910 in which three ridges 9922 are provide on at least the top wall 9912. The three ridges 9922 are provided at or near the intersection of the top wall 9912 with three of the side walls 9916 such that the veneer 9924, when inserted, is secured along three edges 9934 of the veneer 9924. The only edge of the generally rectangular veneer 9924 (shown by way of example only) that is not secured by a ridge 9922 is the trailing edge 9936 containing the tab member 9926. This configuration may be advantageous in that it provides security of the veneer 9924 along three edges 9934, including the leading edge 9934, helping to ensure that the veneer 9924 does not inadvertently "catch" on any anatomical structures as it is being advanced into the intervertebral space.

Figure 21A:
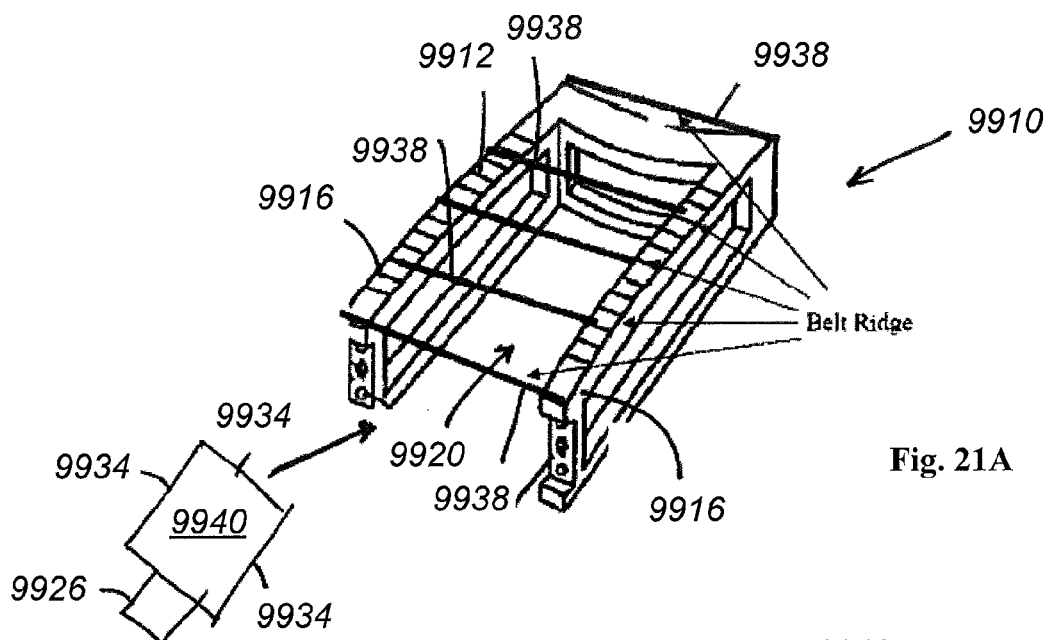
FIGS. 21A, 21B and 21C show three views of a cage and a veneer according to various embodiments of the present disclosure.
Figure 21B:
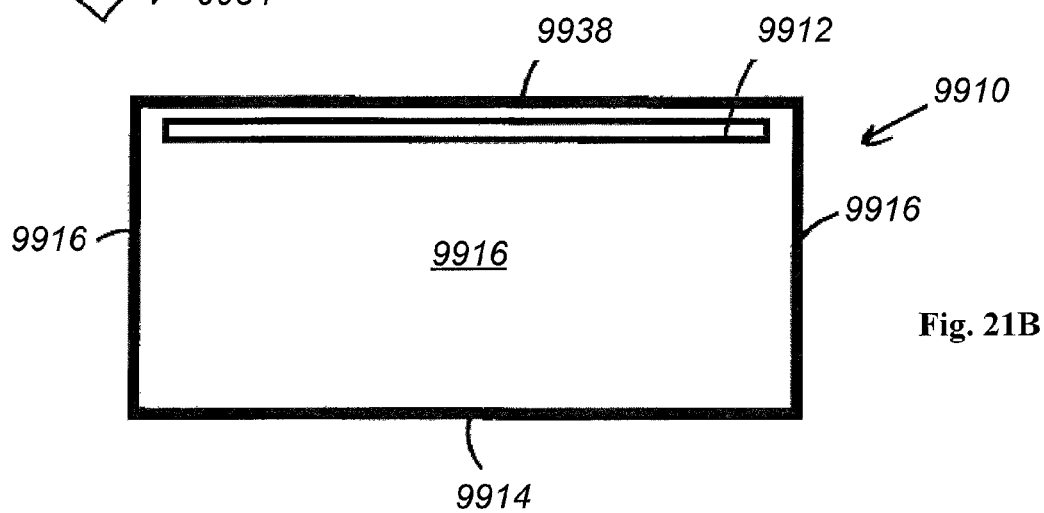
Figure 21C:

Referring to FIGS. 21A, 21B and 21C, a further alternative example of a fusion cage 9910 is a provided, with one or more belt ridges 9938 extending across the top wall 9912 from one of the side walls 9916 to another of the side walls 9916. The one or more belt ridges 9938 are shown by way of example extending across the opening or fenestration 9920. However, other configurations are possible. For example, one belt ridge 9938 may be provided across the top wall 9912 proximate to the trailing wall 9916, while at least one ridge 9922 is provided on the top wall 9912 proximate at least one of the other side walls 9916. In such a fashion, the veneer 9924 would be secured along at least two edges 9934, or along one edge 9934 and the top surface 9940 of the veneer 9924. As illustrated in FIG. 21C, an alternative embodiment of the fusion cage 9910 may be provided having at least one belt ridge 9938 extending over each of the top and bottom walls 9912, 9914.

Figure 22A:
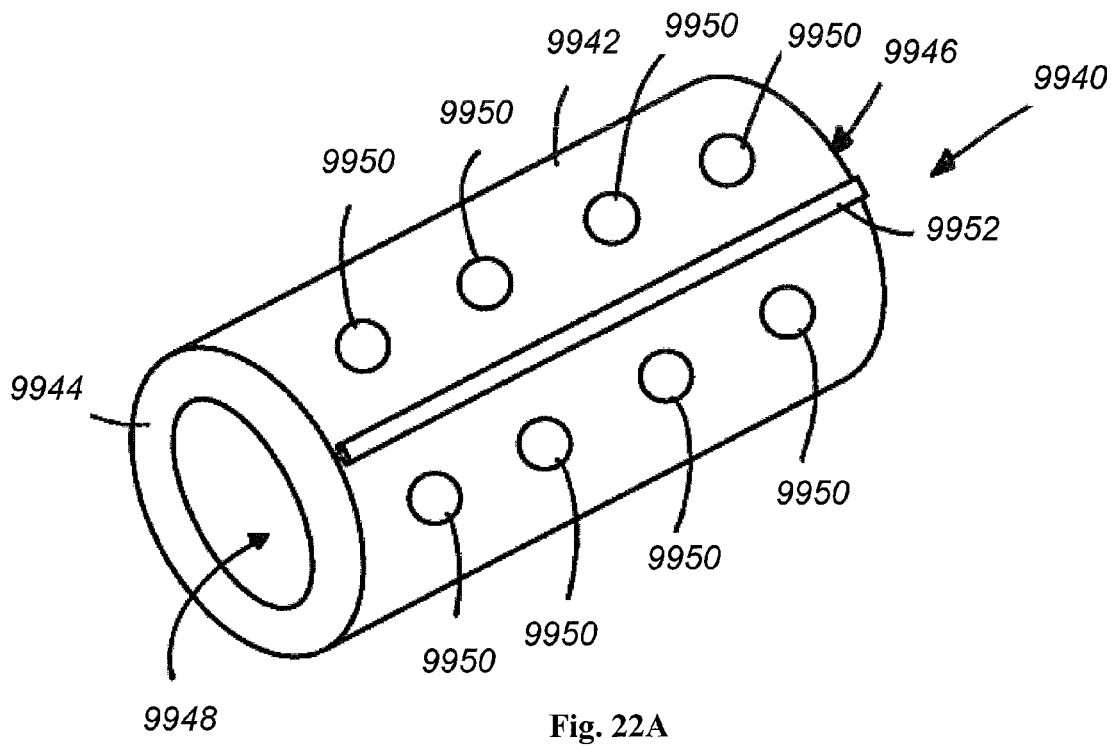
FIGS. 22A and 22B show two views of an implantable cage according to various embodiments of the present disclosure.
Figure 22B:
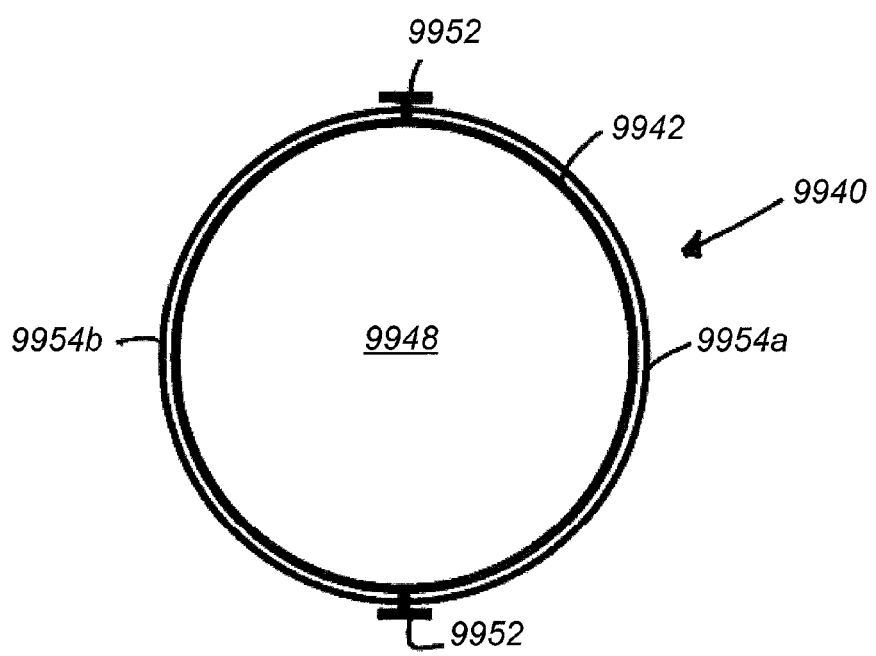

Referring to FIGS. 22A and 22B, an example of a surgically implantable intervertebral fusion cage 9940 having a hollow frame that is substantially tubular, cylindrical or conical in shape is provided according to one embodiment of the present invention. For the sake of simplicity, the cylindrical cage will be referred to herein as having a main wall 9942 that is tubular, cylindrical, or conical in shape and/or configuration, a first end wall 9944 and a second end wall 9946, each end wall 9944, 9946 being interconnected with the main wall 9942 so as to form a closed tube, cylinder, or cone in that the main wall 9942 is connected to the first end wall 9944 and to the second end wall 9946 in such a way that the main wall 9942, first end wall 9944 and second end wall 9946, when fully interconnected, define a hollow interior 9948 to the cage 9940 that is tubular, cylindrical or conical in shape and/or configuration. Preferably, the intervertebral fusion cage 9940 of the present embodiment has a diameter ranging from about 8 mm to about 18 mm and a length ranging from about 18 mm to about 40 mm. Thus, both the first end wall 9944 and the second end wall 9946 preferably have a diameter that ranges from about 8 mm to about 18 mm and the main wall has a length that ranges from about 18 mm to about 40 mm. When fully constructed, the tubular, cylindrical or conical shaped cages have an elongated appearance such that they are longer than they are tall, making the largest points of contact of the cage with the target vertebrae two arcs along the external surface of the main wall 9942, one at the top of the surgical site that makes contact with one of the target vertebrae and one at the bottom of the surgical site that makes contact with a second target vertebra. The first end wall 9944 and the second end wall 9946 may also make contact with the target vertebrae, though it is preferable that the major points of contact with the target vertebrae will occur via the exterior surface of the main wall 9942.

The main wall 9942 has at least one opening or fenestration 9950, and preferably a plurality of openings or fenestrations 9950, located along its length that provide a location, or locations, where material that is placed or stored inside of the hollow interior 9948 may freely move from the hollow interior 9948 to the exterior of the cage 9940. The at least one opening or fenestration 9950 thus allows for fluid communication between the hollow interior 9948 of the cage 9940 and the outside of the cage 9940 in a similar manner as described above.

Additionally, the exterior surface of the main wall 9942 has at least one ridge 9952 located on it, which is configured to hold at least one shield or veneer 9954 in place along the exterior surface of the main wall 9942. In some embodiments, as illustrated by way of example only in FIG. 22A, a single, T-shaped ridge 9952 runs the entire length of the exterior surface of the main wall 9942 such that a single shield or veneer 9954 can be wrapped around the full exterior circumference of the main wall 9942 and be held in place by making contact with both sides of the T-shaped ridge 9952. As stated above, all embodiments of the ridge 9952 may be used to secure one or more veneers 9954 to the external surface of a cage 9940 of these embodiments, though the embodiment of the ridge 9954 that is particularly useful for a cage 9940 of this shape and/or configuration is the T-shaped ridge 9954 shown and described above. In other embodiments and with specific reference now to FIG. 22B, the external surface has at least one ridge 9952, and may also have a plurality of ridges 9952, located thereon and there may be two ridges 9952 running the length of two opposing sides of the external surface of the main wall 9942 such that two veneers 9954, a first veneer 9954*a* and a second veneer 9954*b*, are held in place along two opposing sides of the external surface of the main wall 9942. In one embodiment, there are a plurality of ridges 9952 holding the veneer(s) 9954 in place, at least one ridge 9952 running the length of the external surface of the main wall 9942 as previously described and at least one ridge (not shown) located in a belt-like fashion around the entire perimeter of the external surface of the main wall 9942 such that the veneer 9954 slides under the at least one belt-like ridge, makes contact with the other at least one ridge 9954, and is held in place accordingly.

As mentioned above, the main wall 9942 has at least one, and preferably a plurality of, openings or fenestrations 9950 formed therein that allow for the movement of material out of the hollow interior 9948 and toward the target vertebrae. Therefore, when a veneer 9954 is held in place by a ridge 9952 along the exterior surface of the main wall 9942, the veneer 9954 at least partially blocks or covers, and preferably completely blocks or covers, the at least one opening or fenestration 9950 located along and through the main wall 9942. When the at least one opening or fenestration 9950, and preferably the plurality of openings or fenestrations 9950, are covered or blocked in this manner, the veneer 9954 serves to prevent the movement of material as previously described. Additionally, when the veneer 9954 is removed from contact with the ridge(s) 9952 located along the external surface of the main wall 9942, fluid communication is restored as previously described.

Further description of the features disclosed herein will continue in reference to the example of the interbody fusion cage 9910 having ridges 9922 disclosed above in relation to FIGS. 16A and 16B, however the discussion that follows applies equally to the fusion cage 9940 having ridges 9952 disclosed above in relation to FIGS. 22A and 22B. The ridges 9922 of the present disclosure may be present along the external surface of the cage 9910 in any number of manners. For example, in some embodiments the ridges 9922 are cast with the cage 9910 as an extension of the external surface of the top and/or bottom walls 9912, 9914 of the cage 9910 itself, thereby making the ridge 9922 a continuous physical extension of the cage 9910. In other embodiments, the ridge 9922 is ground out of or machined out of the exterior surface of the cage wall. In these embodiments, the ridge 9922 may be ground out or machined out at the time the cage 9910 is ground out or machined out of a portion of a larger material, or the ridge 9922 may be ground out or machined out in advance of implantation in order to provide a customized ridge 9922. In still other embodiments, the ridge 9922 may be a separate piece that is attached to, or secured onto, the external surface of the cage 9910 prior to implantation. The ridge 9922 of these embodiments may be secured onto the external surface by any one or more of many standard means by which two structures may be operably connected together, such as with the use of adhesives, welding, bands, straps, threading, a clamp, a snap-fit assembly, a bolted or screwed connection, a push-on/turn-on self-locking fastener, a press fit, rivets, and/or other, similar means. In other embodiments of the present disclosure, the ridge 9922 may be present on an internal surface of the cage 9910.

The surgically implantable intervertebral fusion cage 9910 of the present invention, inclusive of the ridges 9922 disclosed herein, may be made of any kind of material suitable for surgical implantation that is also sufficiently rigid so as to provide the required support between the target vertebrae, such as steel or medical grade plastic. In some embodiments, the ridge 9922 is an integral part of the cage 9910 and the two structures are cast as a single, continuous unit. The cages 9910 and the ridges 9922 may be made of: surgical stainless steel of the general alloy type of iron, carbon, chromium (12-20%), molybdenum (0.2-3%), and nickel (8-12%); martensitic steel; 316L or 316LVM austenitic steel; and/or 316 surgical steel. It is desirable for the cages 9910 and ridges 9922 of the present invention to be quite rigid and strong in construction so as to prevent any deforming during use and/or after surgical implantation, which can cause a loss of function.

The veneers 9924 of the present invention may be made of any kind of material suitable for surgical implantation that is rigid enough to completely prevent the movement of viscous materials from the hollow interior when the veneer 9924 is in place along the exterior surface, but that is also sufficiently flexible so as to be readily removable and replaceable without being damaged or deformed in any way. Suitable materials include plastic, poly(tetrafluoroethene) or poly(tetrafluoroethylene), or plastic, though the veneers 9924 may also be made of polyamide, polyethylene, polypropylene, polyphenylene sulfide, polyurethane, poly(tetrafluoroethylene), polyvinyl chloride, polyvinylidene fluoride or polyetheretherketone (PEEK).

In accordance with at least some aspects of at least one embodiment of the present invention, a method of surgically implanting an intervertebral fusion cage 9910 into a patient is provided. The method comprises first obtaining a surgically implantable intervertebral fusion cage 9910 having at least one wall (for example top wall 9912), at least one ridge 9922 located on an exterior surface of the at least one wall 9912, and at least one removable shield or veneer 9924. The at least one wall 9912 defines a hollow interior to the cage 9910 and has at least one opening or fenestration 9920 in it that allows for fluid communication between the hollow interior and an exterior of the cage 9910. The ridge 9922 is operable to hold the at least one veneer 9924 in contact with the exterior surface and is configured to allow the at least one veneer 9924 to be freely removed from, and replaced onto, the exterior surface of the wall 9912.

The next step of the method is to prepare the cage 9910 for surgical implantation by filling the hollow interior with a material capable of fusing two bony structures, preferably two vertebrae, and more preferably two adjacent vertebrae, together. For example this material may be an orthopedic matrix containing additional fusion-promoting material (FPM), for example including but not limited to calcium hydroxyapatite, bone morphogenic protein (BMP), demineralized bone matrix, collagen bone graft matrix (e.g. Formagraft®) and stem cell material (e.g. Osteocel®) or other fusion-promoting substance placed within the spaces of the implant. The next step is contacting the at least one veneer 9924 with the exterior surface of the cage 9910 by positioning the veneer 9924 under at least a portion of the at least one ridge 9922 such that the at least one veneer 9924 is contacted with and held in place along the exterior surface of the top wall 9912 by the at least one ridge 9922 by way of such contact. Preferably, when the at least one veneer 9924 is contacted with the at least one ridge 9922, the veneer 9924 at least partially covers or blocks the at least one opening or fenestration 9920, preventing fluid communication between the hollow interior and the exterior of the cage 9910, and preventing the material from leaving the hollow interior.

After the cage 9910 has been prepared for implantation, the next step of the method is to locate an appropriate surgical site in a patient for implantation of the cage 9910. The surgical site may be an intervertebral location, including the space typically filled by an intervertebral disc, but may also be any location in a patient where two bony structures are to be fused together. The next step in the method is to create a surgical opening and operative corridor in the patient that will accommodate the cage 9910. This opening may be made dorsally, ventrally, laterally or at any other location along the patient that is medically efficacious to grant the user access to the surgical site. Once the opening is created, the next step in the method is to surgically implant the cage 9910 into the patient and then position it in the surgical site between the desired bony structures, and preferably between the two adjacent vertebrae of interest, in such a way that will serve to utilize the material in connection with the patient's own systems to promote the fusion of the two bony structures by way of, and though, the cage 9910. Thereafter, the at least one veneer 9924 is removed from contact with the ridge and the exterior surface of the cage 9910, thereby restoring fluid communication between the hollow interior and the exterior of the cage 9910 and allowing the material to move from the hollow interior to the exterior of the cage 9910. Once these tasks are completed, the method is concluded by closing the surgical opening in the patient.

Embodiments of the present invention may comprise any one or more of the novel features described herein, included in the Detailed Description, included in the Brief Summary of the Invention and/or shown in the drawings. The claims may include one or more features of any one or more of the embodiments described herein. For example, one or more features of one embodiment may be claimed in combination with one or more features of another embodiment, and no portion of this specification limits such claims.

The present inventions, in various embodiments, include components, methods, processes, systems and/or apparatuses substantially as depicted and described herein, including various embodiments, subcombinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the inventions has been presented for purposes of illustration and description. The foregoing is not intended to limit the inventions to the form or forms disclosed herein. In the foregoing Detailed Description for example, various features of the inventions are grouped together in one or more embodiments for the purpose of streamlining the disclosure. This method of disclosure is not to be interpreted as reflecting an intention that the claimed inventions require more features than are expressly recited in each claim. Rather, as the following claims reflect, inventive aspects lie in less than all features of a single foregoing disclosed embodiment. Thus, the following claims are hereby incorporated into this Detailed Description by this reference, with each claim standing on its own as a separate preferred embodiment of the inventions.

Moreover though the description of the inventions has included descriptions of one or more embodiments and certain variations and modifications, other variations and modifications are within the scope of the inventions, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for performing spinal fusion, comprising:
    an intervertebral fusion cage having a frame that comprises a top wall, a bottom wall, a leading end, a trailing end, and a pair of lateral walls, the intervertebral fusion cage having a hollow interior and an exterior, and the top wall and the bottom wall each have at least one opening allowing for fluid communication between the hollow interior and an exterior, said cage configured for receiving in its interior a fusion promoting material comprising bone graft material, for placement within the hollow interior of the fusion cage;
    said cage adapted to receive generally planar elements disposed on at least one of the top wall, bottom wall, and pair of lateral walls of the cage, said generally planar elements configured to reversibly cover the at least one opening in one of the top wall and the bottom wall, said generally planar elements preventing leakage of the fusion promoting material out of the at least one opening, said generally planar elements providing a barrier to the undesired translocation of the fusion-promoting material and substantially precluding fluid communication between the hollow interior and the exterior of the cage, such that said fusion promoting material is maintained within the hollow interior of the intervertebral fusion cage during insertion of the intervertebral fusion cage into the intervertebral space, and wherein said generally planar elements are configured to be removable from the intervertebral fusion cage when the intervertebral fusion cage is placed in the intervertebral space, wherein fluid communication is permitted between the hollow interior and the exterior of the cage and allows the fusion promoting material to move from the hollow interior to the exterior of the cage.

2. The system of claim 1, wherein said intervertebral fusion cage includes a first aperture formed in said trailing end, said first aperture configured to mate with an inserter.

3. The system of claim 1, wherein said intervertebral fusion cage includes a first aperture formed in said trailing end and wherein said first aperture is threaded.

4. The system as set forth in claim 1, wherein the generally planar elements comprise veneers that are disposed on either side of a fusion implant having more than one aperture adapted for receiving fusion-promoting material.

5. The system as set forth in claim 4, wherein the veneers are held in place so as to prevent unintended movement of the veneers during surgical implantation of the cage.

6. The system as set forth in claim 4, wherein the veneers are removed from the cage upon surgical implantation of the cage.

7. The system as set forth in claim 4, wherein fusion promoting material flows from the interior of the cage out of the openings and into contact with target vertebrae on the top of the cage and at the bottom of the cage, and the veneers retain a portion of the material inside the hollow interior sufficient to promote fusion of the target vertebrae by the generation of osseous tissue through and around the fusion cage.

8. The system as set forth in claim 1, wherein the bottom wall has a plurality of openings that provide access to the hollow interior of the cage and that allow for fluid communication between the hollow interior and the exterior of the cage, said plurality of openings permitting a fusion-promoting material that is inserted into the hollow interior prior to surgical implantation, to leave the hollow interior of the cage, make contact with desired vertebrae and promote the fusion of the desired vertebrae.

9. A system for performing spinal fusion, comprising:
an intervertebral fusion cage having a frame comprised of a top wall, a bottom wall, a leading end, a trailing end, and a pair of lateral walls, the intervertebral fusion cage having a hollow interior and an exterior, and the top wall and the bottom wall each have at least one opening adapted to receive fusion promoting material, at least one recess located on an exterior surface of the top wall, and at least one recess located on an exterior surface of the bottom wall; a fusion promoting material configured for placement within the hollow interior of the fusion cage; at least two veneers, each having first and second elongated tangs, said first tang being configured to slidingly engage with the at least one recess located on an exterior surface of the top wall, and said second tang being configured to slidingly engage the at least one recess located on an exterior surface of the bottom wall, said at least two veneers configured to reversibly hold the intervertebral fusion cage in contact with the tangs so as to at least partially cover the at least one opening in the top wall and the at least one opening in the bottom wall, said at least two veneers being associated with said cage to substantially preclude fluid communication between the hollow interior and the exterior of the cage such that said fusion promoting material is maintained within the hollow interior of the intervertebral fusion cage during insertion of the intervertebral fusion cage into the intervertebral space, and wherein said at least two veneers are configured to be removable from the intervertebral fusion cage when the intervertebral fusion cage is placed in the intervertebral space.

10. The system of claim 9, wherein said at least two veneers cover said at least one opening to prevent the movement of fusion promoting material from the hollow interior to the exterior of the cage.

11. The system of claim 9, wherein the fusion-promoting material is at least one of calcium hydroxyapatite, bone morphogenic protein, demineralized bone matrix, collagen bone graft matrix, and stem cell material.

* * * * *